US 6,547,779 B2

(12) United States Patent
Levine et al.

(10) Patent No.: US 6,547,779 B2
(45) Date of Patent: *Apr. 15, 2003

(54) FLEXIBLE FLOW APPARATUS AND METHOD FOR THE DISRUPTION OF OCCLUSIONS

(75) Inventors: Marc-Alan Levine, San Francisco, CA (US); Eduardo U. Sucgang, South San Francisco, CA (US); Stephen J. Hebert, Berkeley, CA (US); Estela D. Gatchalian, San Jose, CA (US); Quang Q. Tran, Fremont, CA (US); Victor C. Esch, San Francisco, CA (US)

(73) Assignee: Endovasix, Inc., Belmont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/328,514

(22) Filed: Jun. 9, 1999

(65) Prior Publication Data

US 2003/0009157 A1 Jan. 9, 2003

Related U.S. Application Data

(63) Continuation-in-part of application No. 09/165,435, filed on Oct. 2, 1998, now Pat. No. 6,210,400, which is a continuation-in-part of application No. 09/120,598, filed on Jul. 22, 1998, now Pat. No. 6,139,543.

(51) Int. Cl.[7] .............................................. A61B 18/18
(52) U.S. Cl. ................. 606/7; 606/13; 606/15; 606/128; 128/898; 607/89
(58) Field of Search .................. 606/7–9, 3, 13–16, 606/127, 728; 607/89; 128/898

(56) References Cited

U.S. PATENT DOCUMENTS

| 4,739,768 A | * | 4/1988 | Engelson ..................... 128/658 |
| 4,747,405 A | * | 5/1988 | Leckrone ................. 128/303.1 |
| 5,041,108 A | * | 8/1991 | Fox et al. ....................... 606/7 |
| 5,059,200 A | | 10/1991 | Tulip .......................... 606/128 |

(List continued on next page.)

FOREIGN PATENT DOCUMENTS

| DE | 3840126 A | 5/1990 |
| EP | 0571306 A | 11/1993 |
| WO | WO9110403 A | 7/1991 |
| WO | W9920189 | 4/1999 |
| WO | W0003292 | 1/2000 |

OTHER PUBLICATIONS

Yuan, H. and Prosperetti, A. (1997) "Gas–liquid Heat Transfer in a Bubble Collapsing Near a Wall," *Phys. Fluids* 9(1):127–142.

(List continued on next page.)

*Primary Examiner*—Linda C. M. Dvorak
*Assistant Examiner*—Ahmed Farah
(74) *Attorney, Agent, or Firm*—Skjerven Morrill LLP; K. Alison De Runtz

(57) ABSTRACT

Methods and apparatus for creating fluid flow from one location to another are disclosed. The fluid flow is created via the absorption of repetitive pulses of radiation in a fluid to generate bubbles that expand and collapse repetitively. This fluid mechanism, or pumping phenomenon, can be used to aid removal of a total or partial occlusion in a body passage by disrupting a surface of the occlusion with acoustic shock and pressure waves and/or by causing mechanical disruption of the occlusive material. Appropriate selection of materials and particular constructions improve apparatus flexibility.

244 Claims, 20 Drawing Sheets

U.S. PATENT DOCUMENTS

| | | | |
|---|---|---|---|
| 5,085,659 A | * | 2/1992 | Rydell .......................... 606/47 |
| 5,095,915 A | | 3/1992 | Engelson |
| 5,207,988 A | | 5/1993 | Lucas |
| 5,304,171 A | | 4/1994 | Gregory et al. |
| 5,312,356 A | | 5/1994 | Engelson et al. |
| 5,370,617 A | | 12/1994 | Sahota |
| 5,437,659 A | * | 8/1995 | Leckrone ........................ 606/7 |
| 4,739,768 A | | 10/1995 | Engelson |
| 5,472,406 A | | 12/1995 | de la Torre et al. |
| 5,599,492 A | | 2/1997 | Engelson |
| 5,649,923 A | | 7/1997 | Gregory et al. |
| 5,662,590 A | | 9/1997 | de la Torre et al. |
| 5,746,709 A | | 5/1998 | Rom et al. |
| 5,944,687 A | | 8/1999 | Benett et al. |
| 5,964,751 A | * | 10/1999 | Amplatz et al. ............... 606/15 |
| 6,022,309 A | | 2/2000 | Celliers et al. |
| 6,024,738 A | * | 2/2000 | Daikuzono et al. ............ 606/7 |
| 6,033,371 A | | 3/2000 | de la Torre et al. |
| 6,056,743 A | * | 5/2000 | Eelis et al. .................... 606/15 |
| 6,066,130 A | | 5/2000 | Gregory et al. |
| 6,102,905 A | * | 8/2000 | Baxter et al. .................. 606/15 |
| 6,106,546 A | | 8/2000 | Gregory |
| 6,139,543 A | * | 10/2000 | Esch et al. ...................... 606/7 |
| 6,156,029 A | * | 12/2000 | Mueller .......................... 606/7 |
| 6,200,307 B1 | * | 3/2001 | Kasinkas et al. ............... 606/7 |
| 6,210,400 B1 | * | 4/2001 | Hebert et al. ................... 606/7 |

OTHER PUBLICATIONS

International Search Report for PCT Application No. CPT/US99/16371, mailed Nov. 12, 1999.

Brujan, E.A. et al. (1996) "Dynamics of Laser–Induced Cavitation Bubbles in Polymer Solutions," *ACUSTICA acta acustica* 82:423–430.

Hao, Y. and Prosperetti, A. (1999) "The Dynamics of Vapor Bubbles in Acoustic Pressure Fields," *Physics of Fluids* 11(8):2008–2019.

Jun, Thomas K. and Kim, Chang–Jin (1996) "Microscale Pumping with traversing Bubbles in Microchannels," *Solid–State Sensor and Actuator Workshop*, Hilton Head, South Carolina pp. 144–147.

Oguz, H.N. and Prosperetti, A. (1998) "The Natural Frequency of Oscillation of gas Bubbles in Tubes," *J. Acoust. Soc. Am.* 103:3301–3308.

Yuan, H. et al. (1990) "Growth and Collapse of a Vapor Bubble in a Small Tube," *International Journal of Heat and Mass Transfer* 42:3643–3657.

Written Opinion of International Application No. PCT/US99/16371.

* cited by examiner

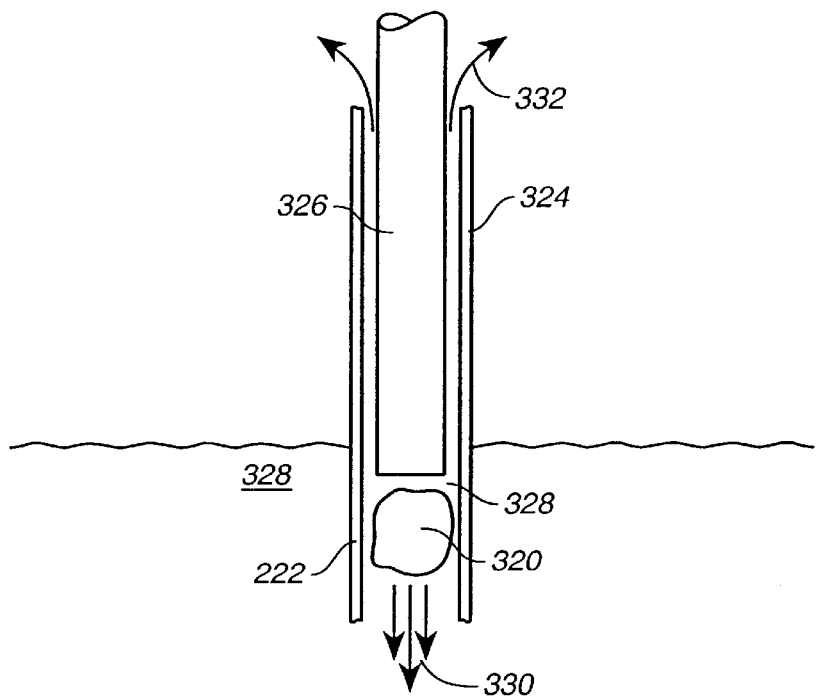
FIG._1 EXPANSION DIRECTION OF BUBBLE
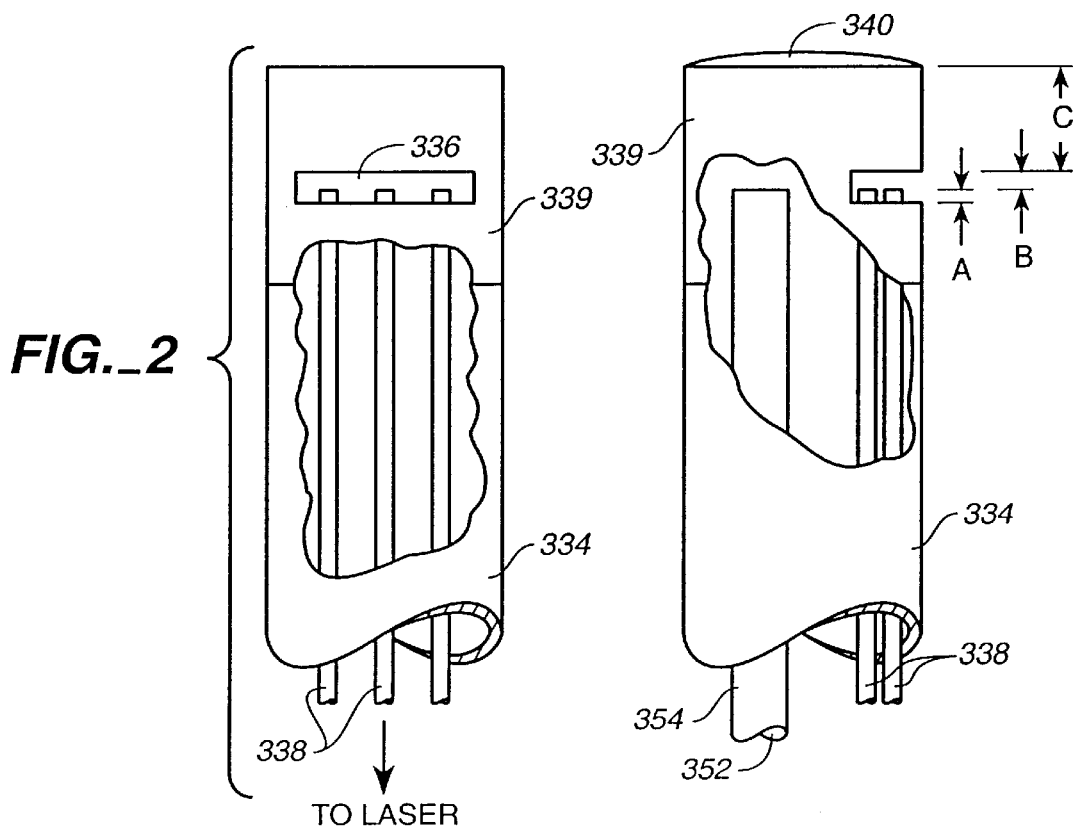
FIG._2

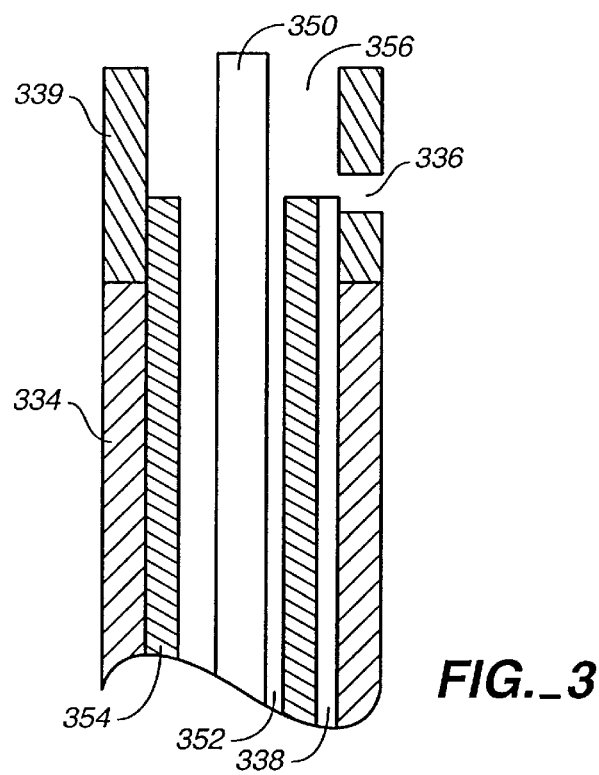
FIG._3
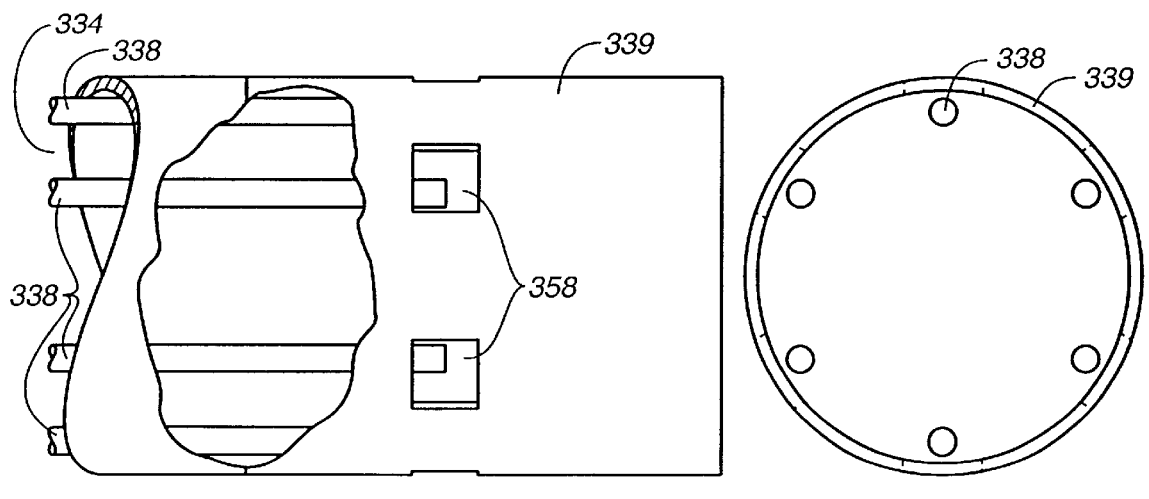
FIG._4

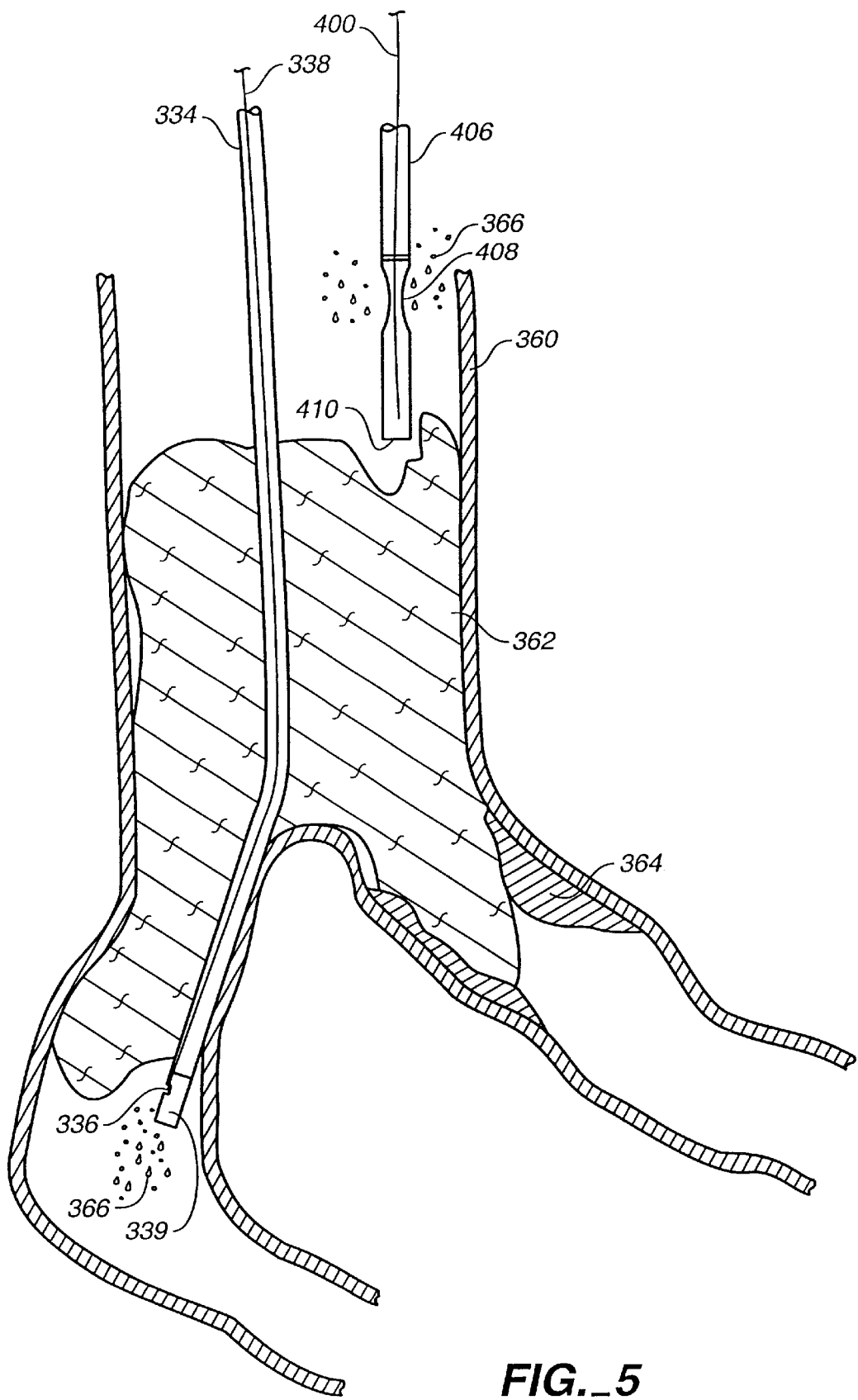
FIG._5

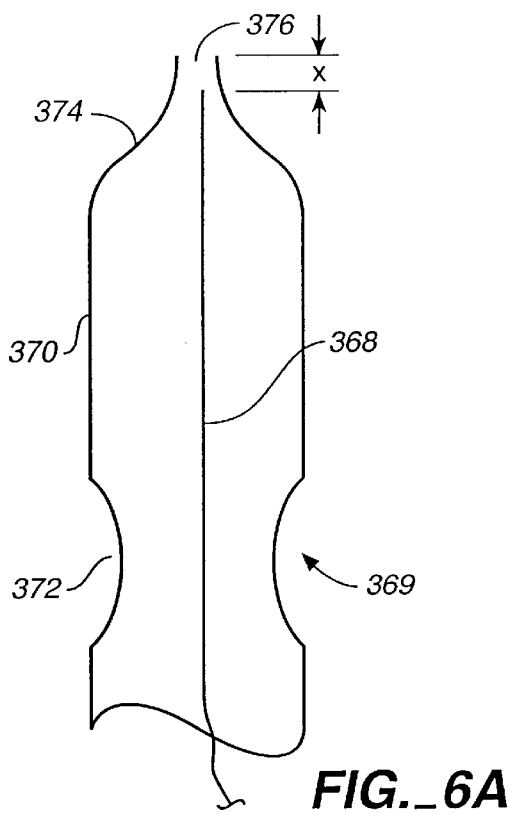
FIG._6A
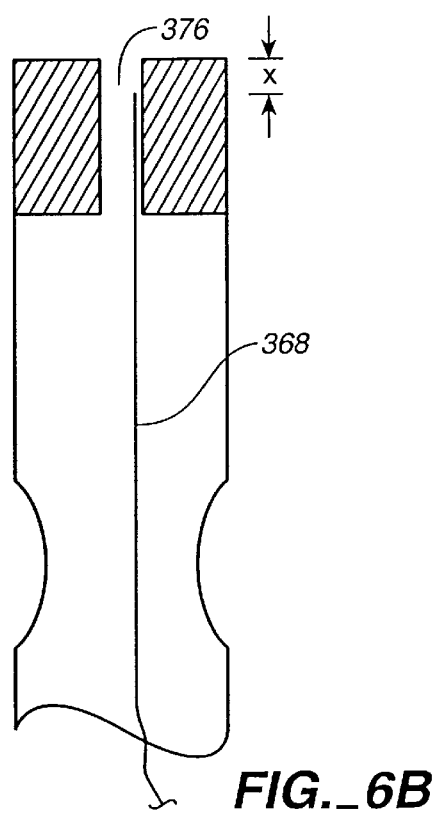
FIG._6B
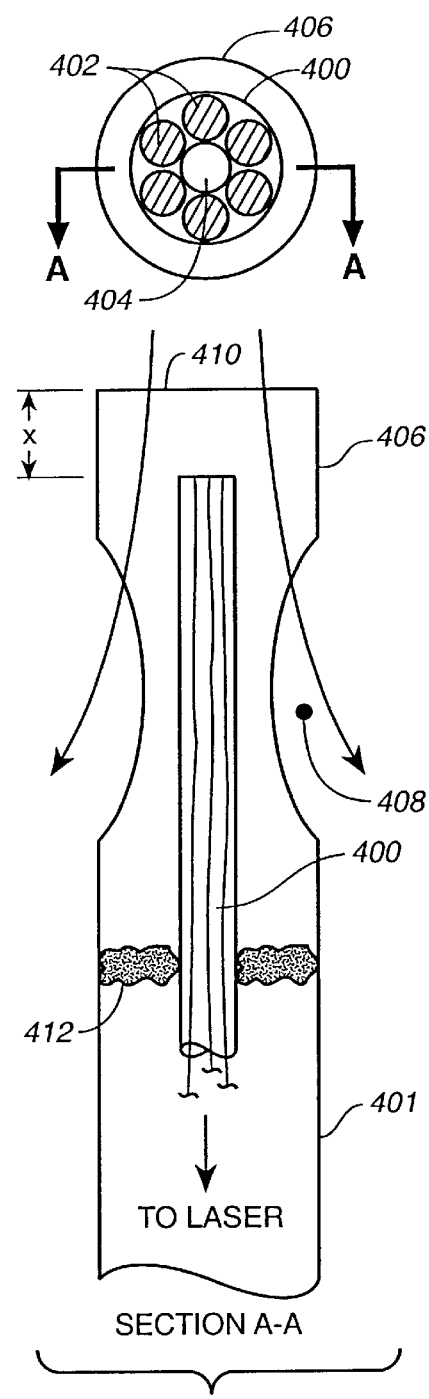
FIG._7

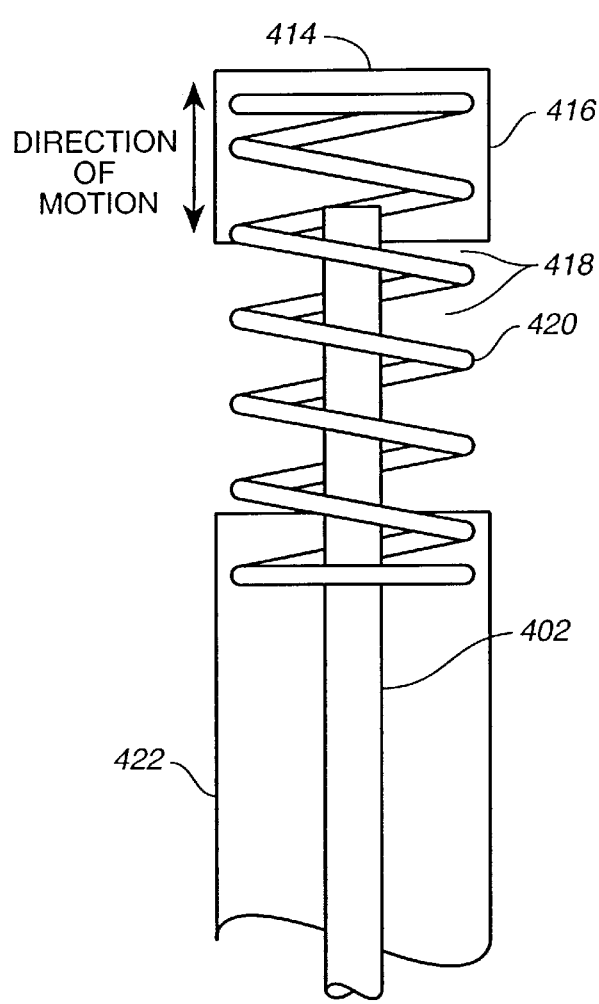
FIG._8
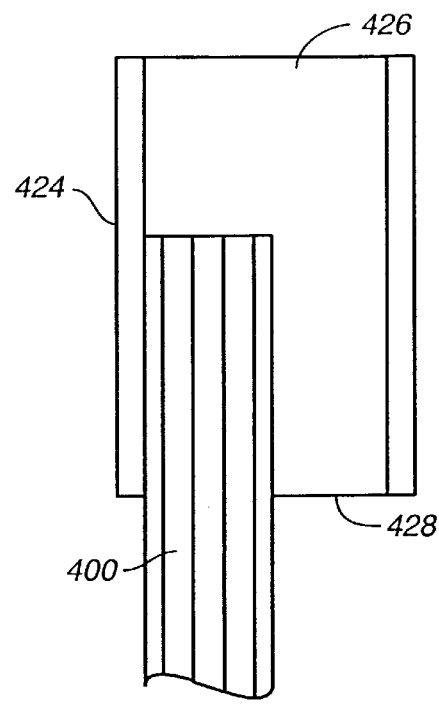
FIG._9
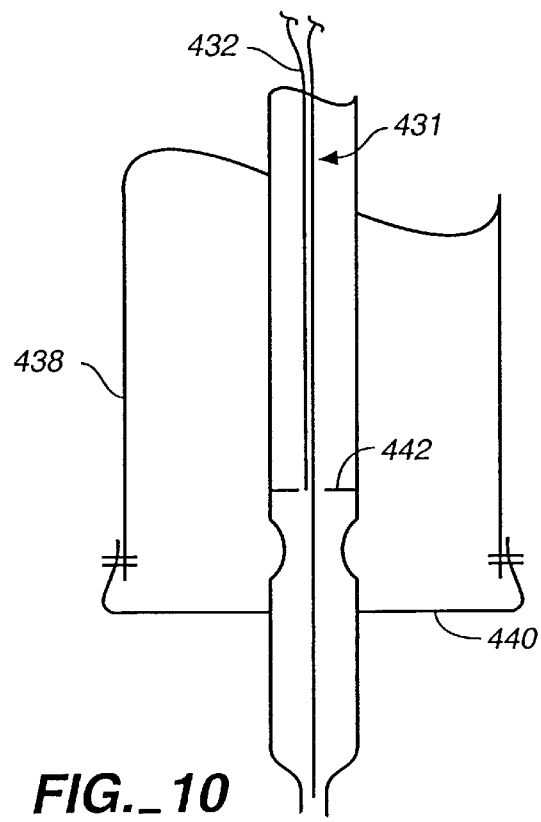
FIG._10

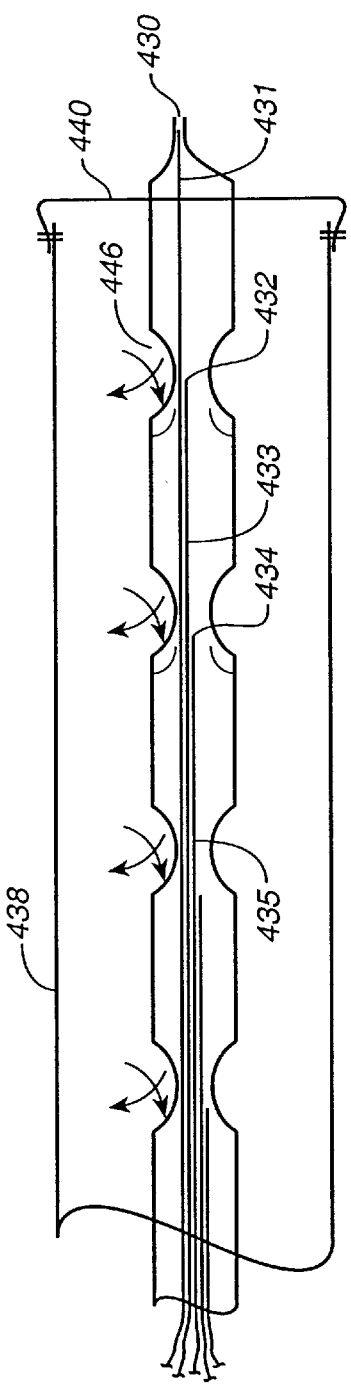
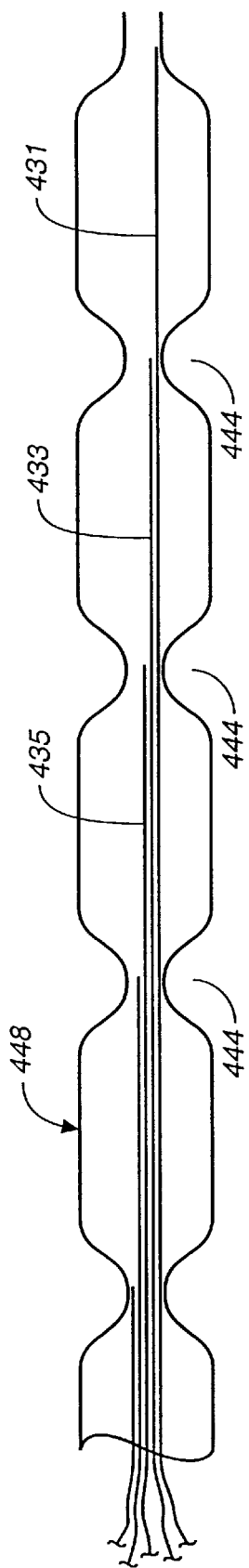
FIG._11A
FIG._11B

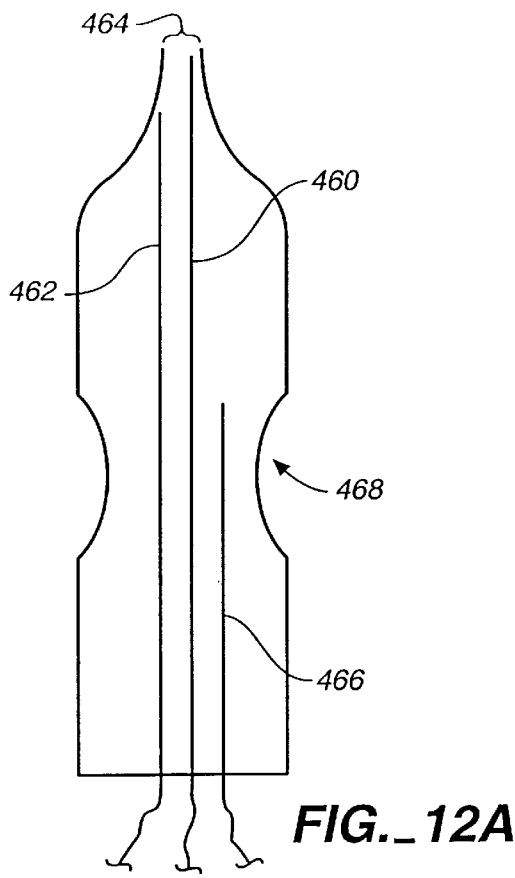
FIG._12A
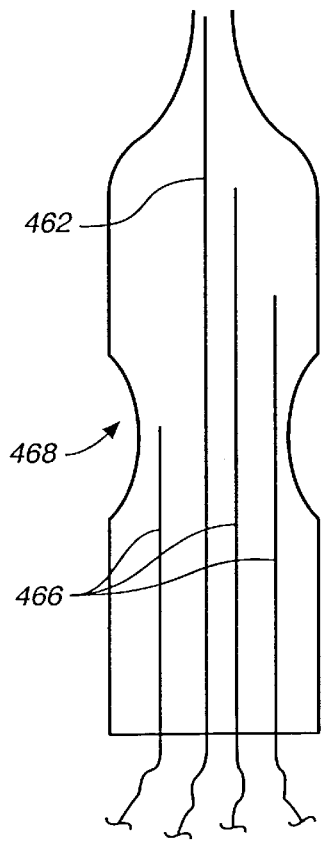
FIG._12B
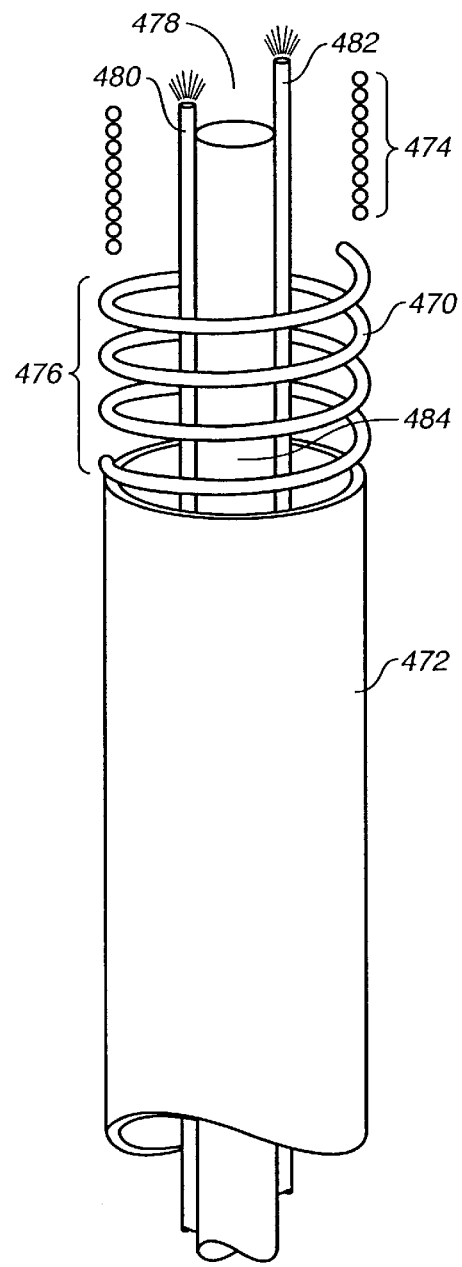
FIG._13

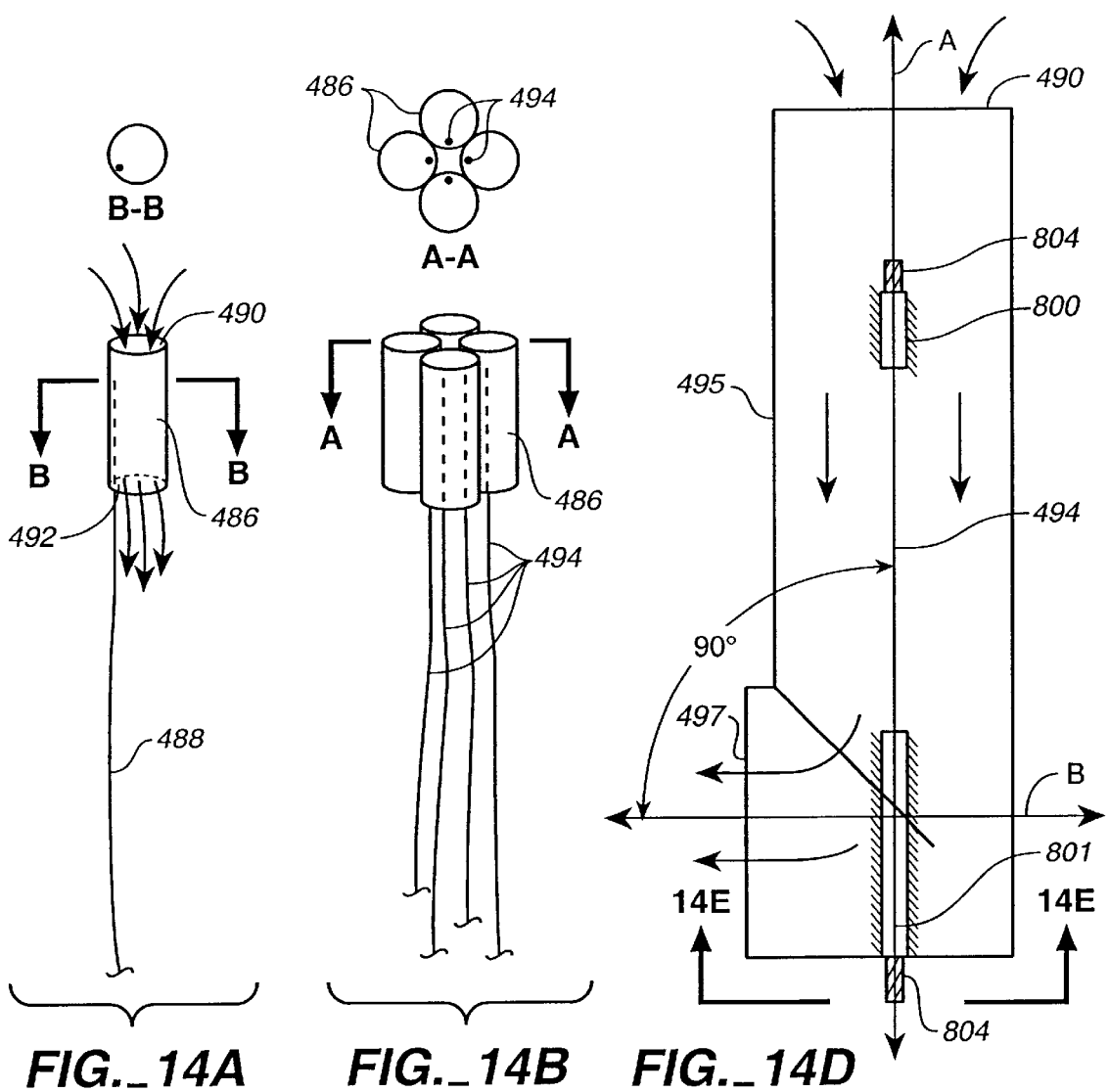
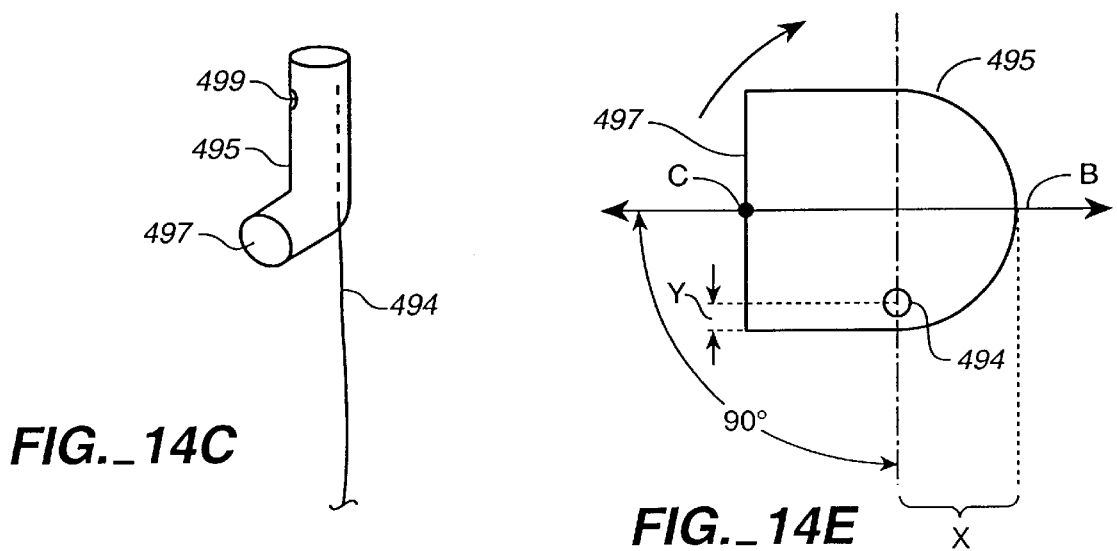
FIG._14A  FIG._14B  FIG._14D
FIG._14C  FIG._14E

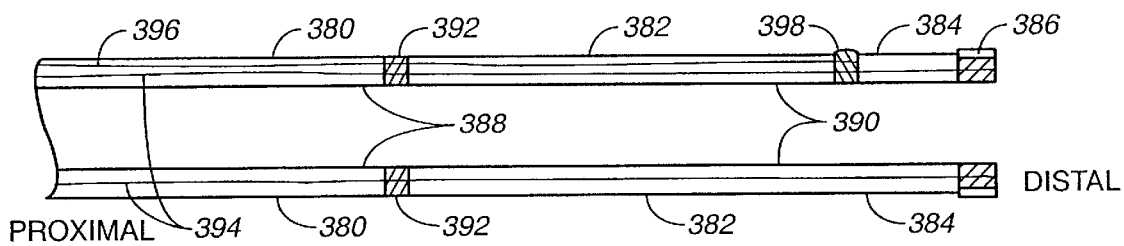
FIG._15A
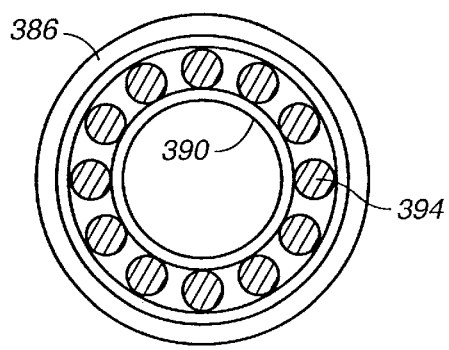
FIG._15B
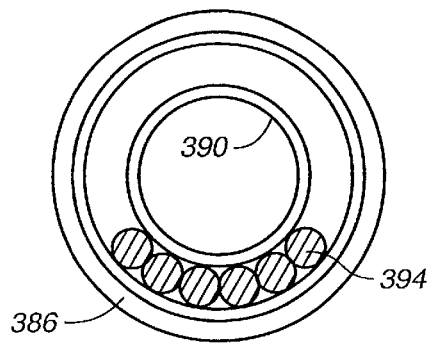
FIG._15C
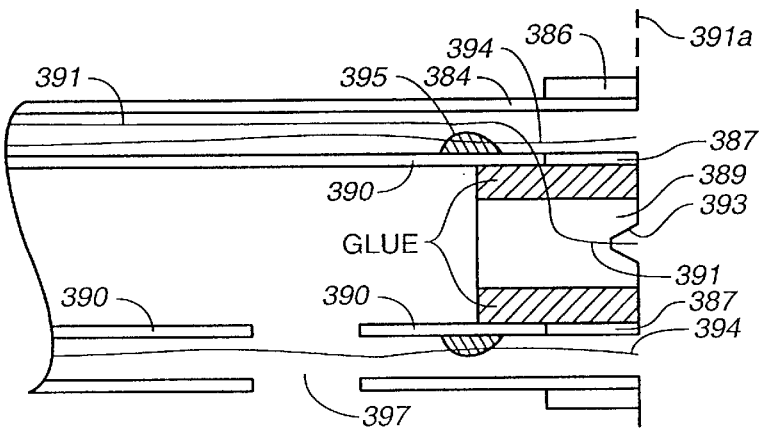
FIG._15D

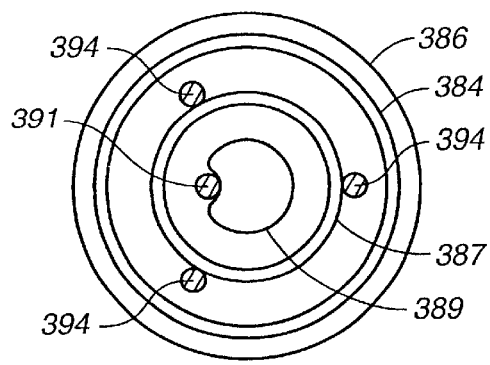
FIG._15E
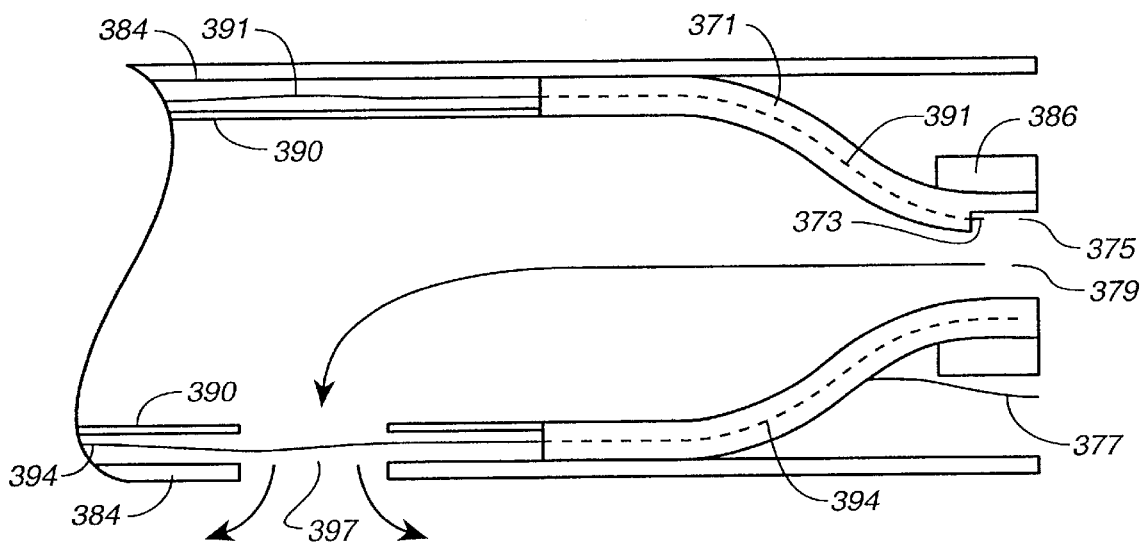
FIG._16A
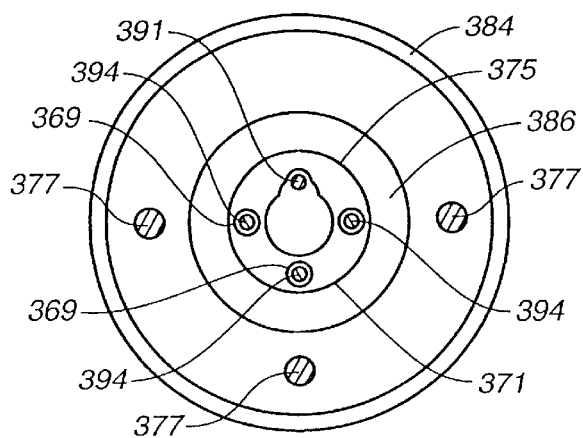
FIG._16B

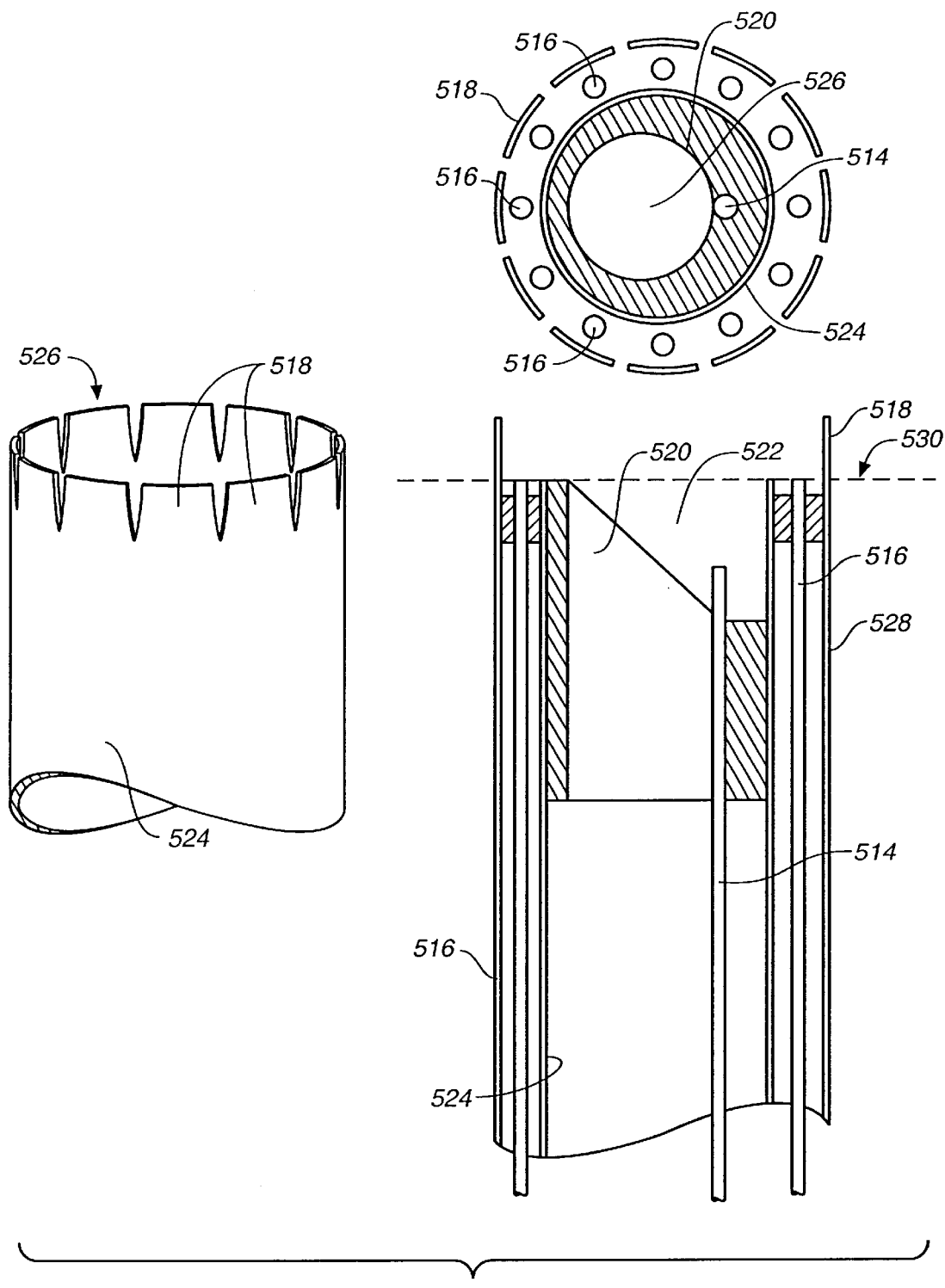
FIG._17

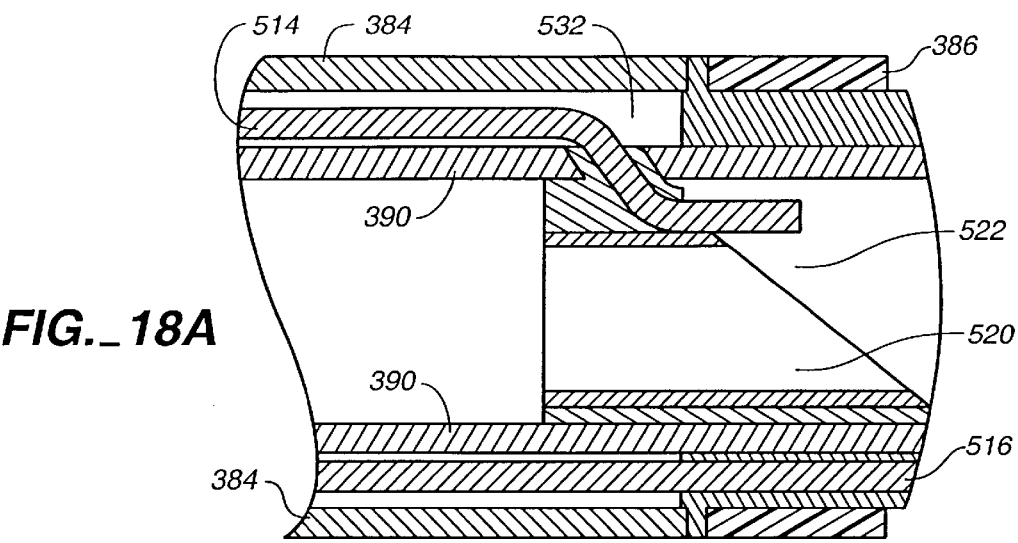
FIG._18A
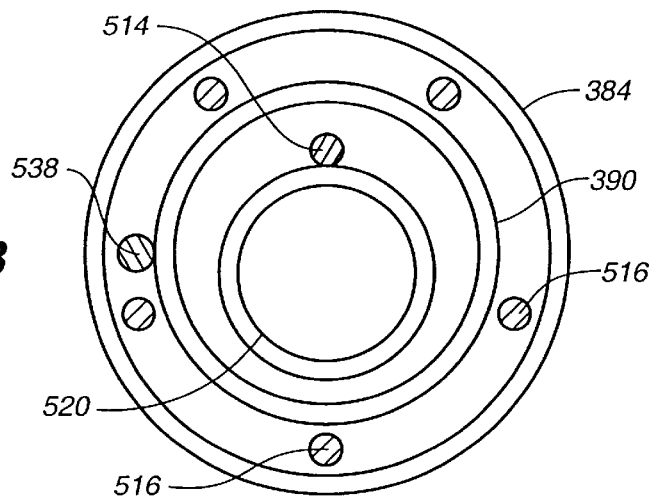
FIG._18B
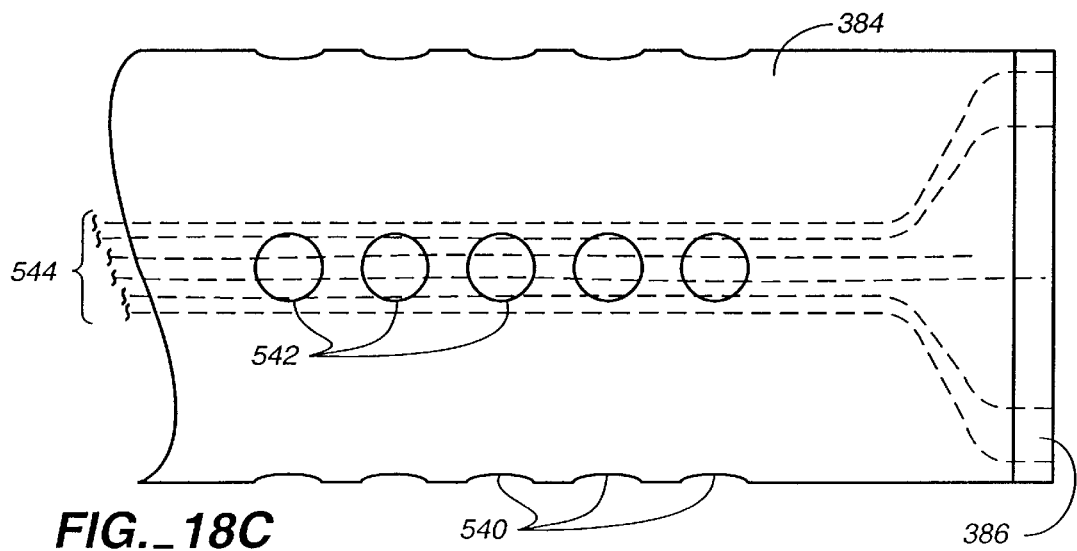
FIG._18C

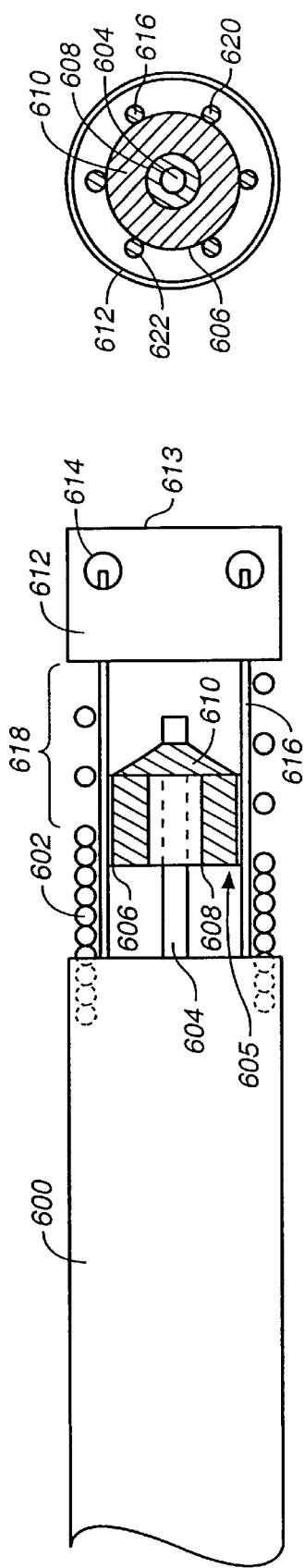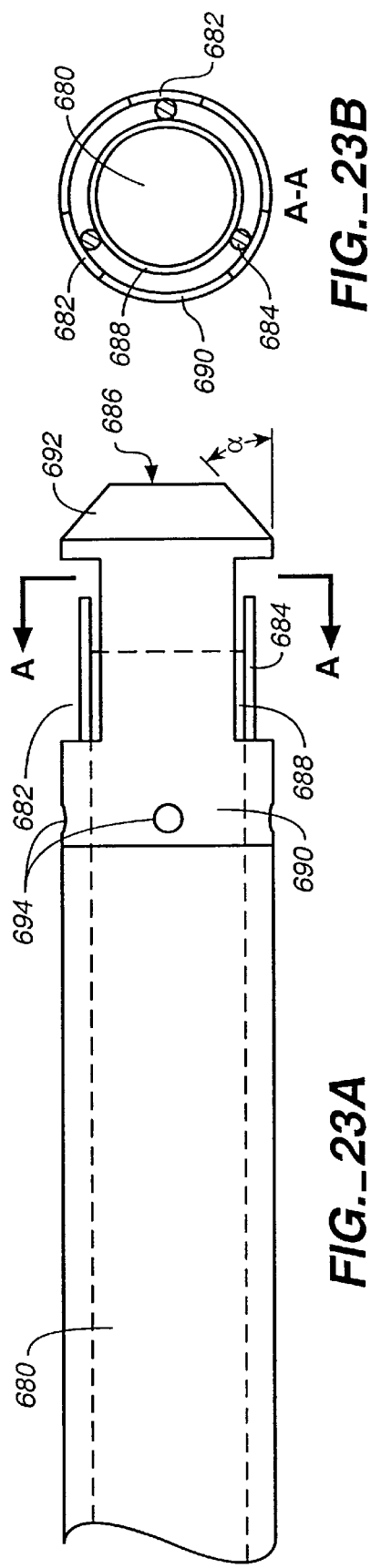

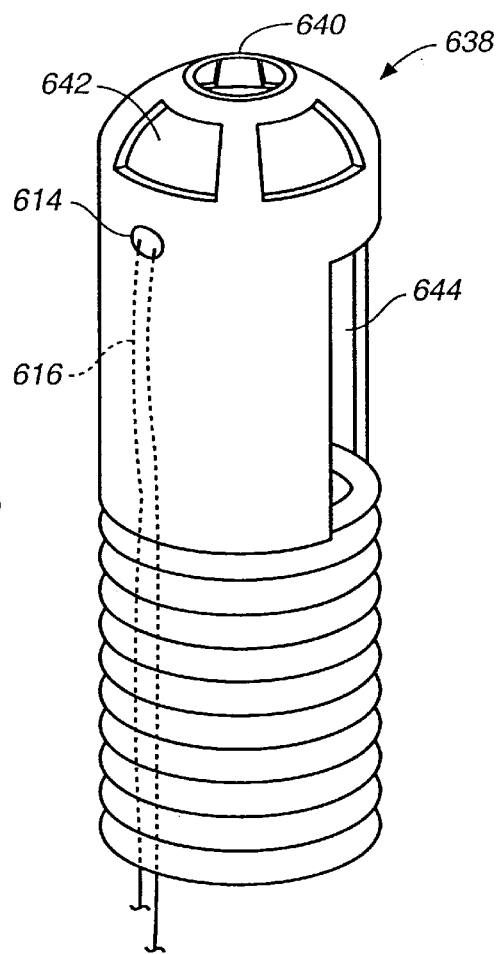
FIG._20
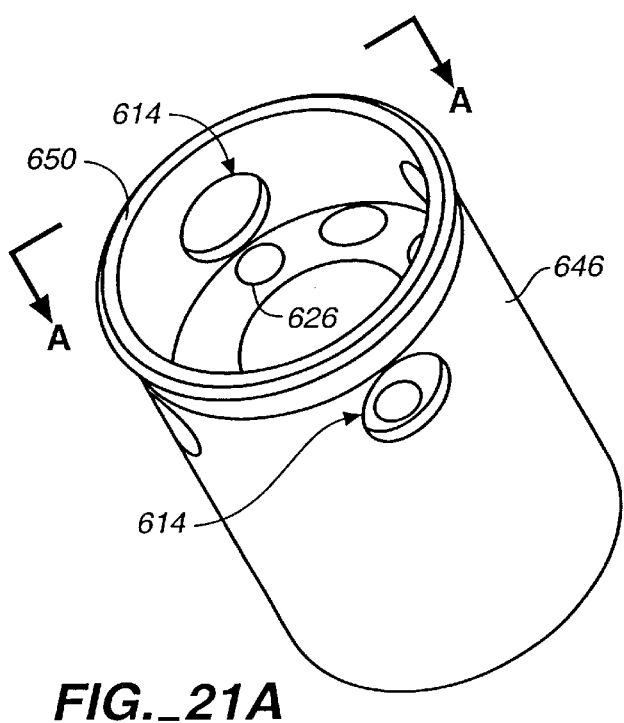
FIG._21A
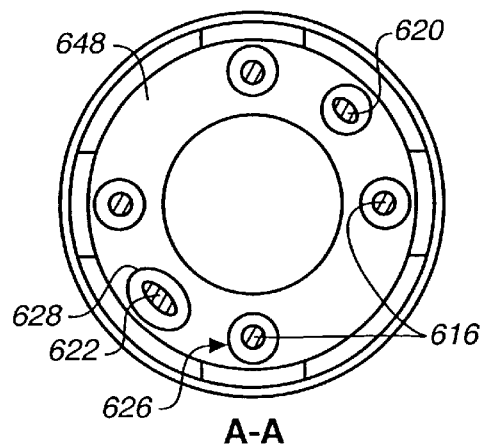
A-A
FIG._21B

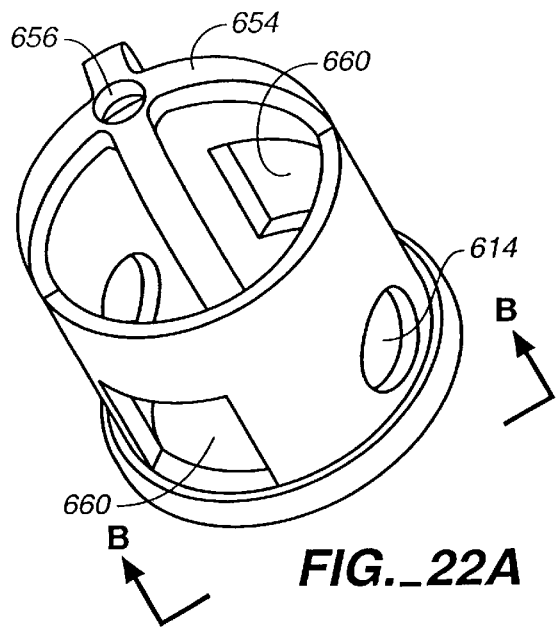
FIG._22A
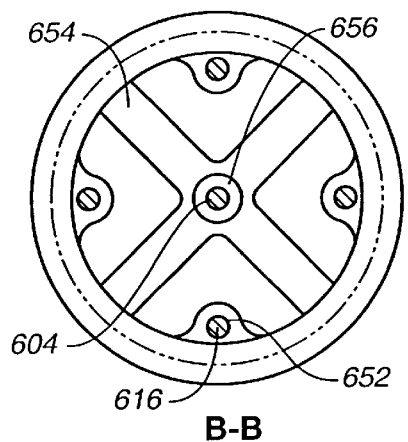
FIG._22B
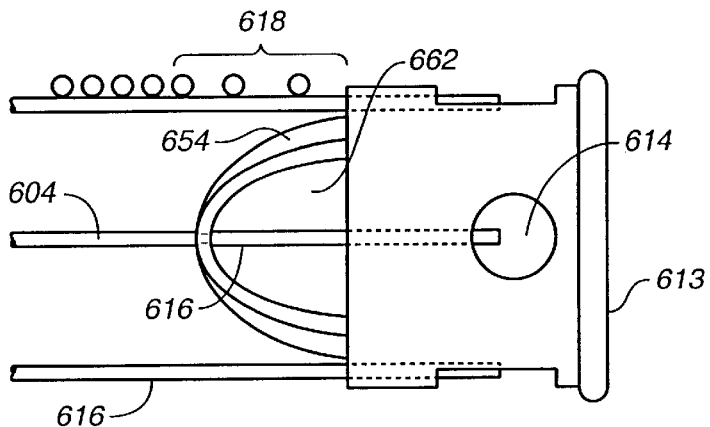
FIG._22C
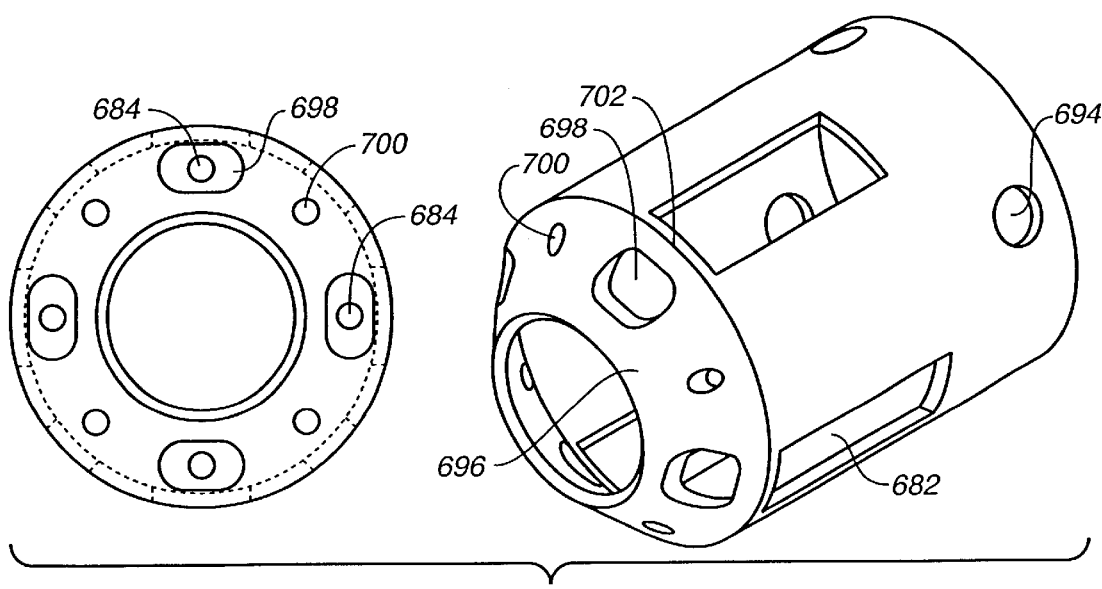
FIG._24

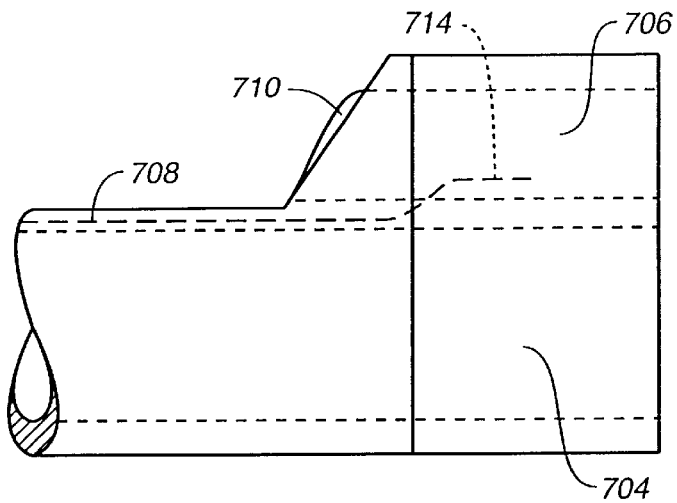
FIG._25A
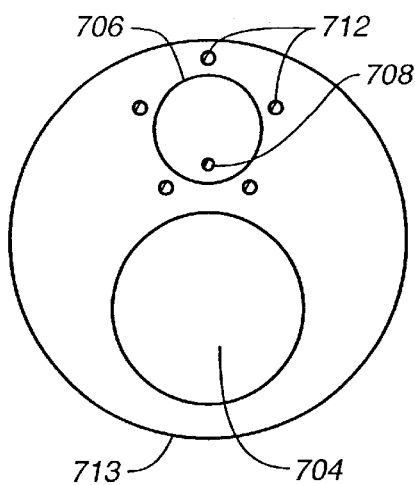
FIG._25B
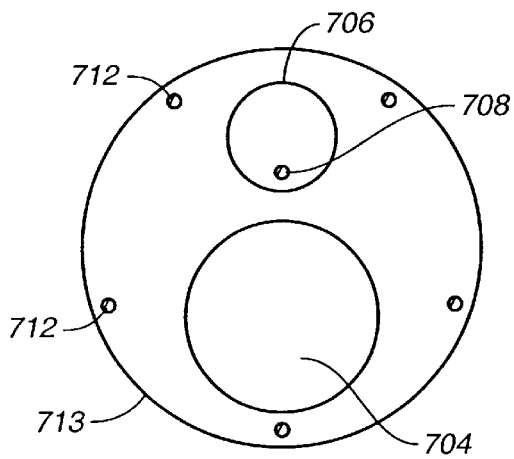
FIG._25C
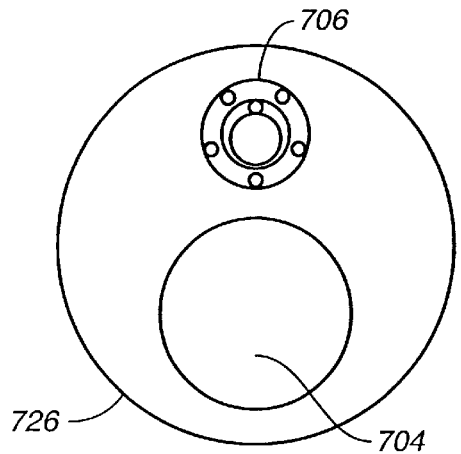
FIG._25D
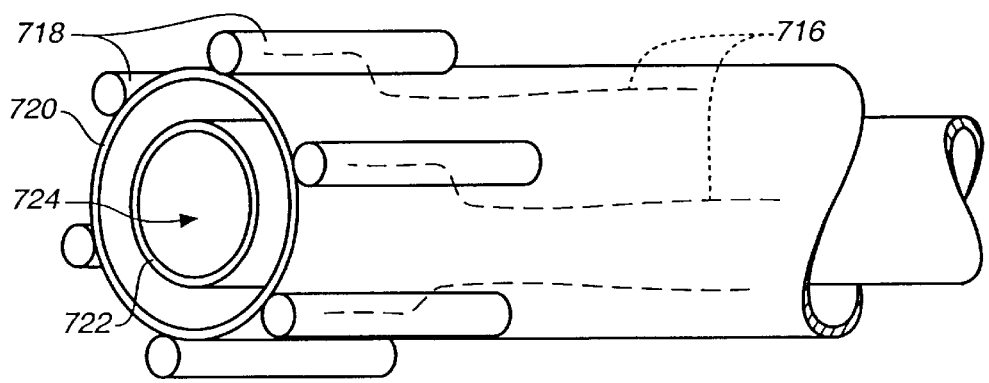
FIG._26

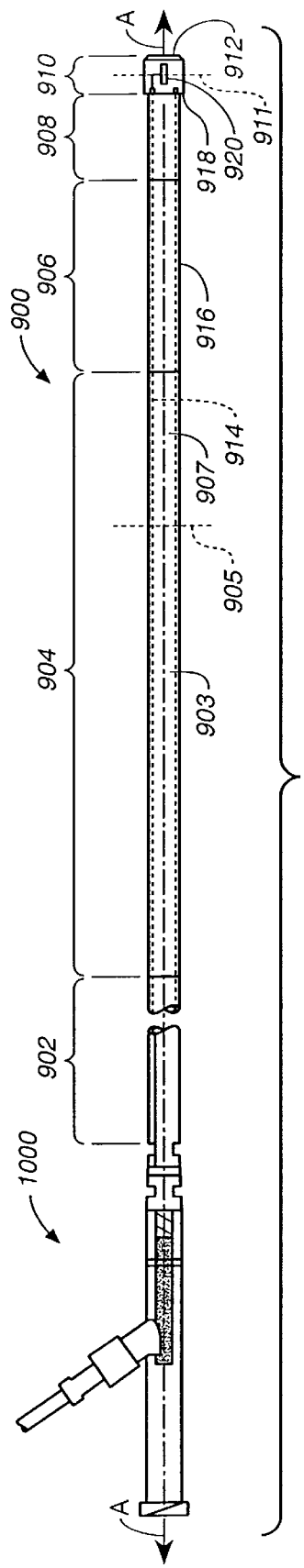
FIG._27A
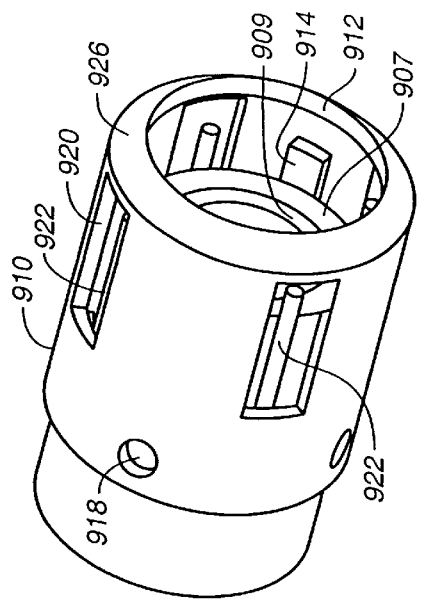
FIG._27C
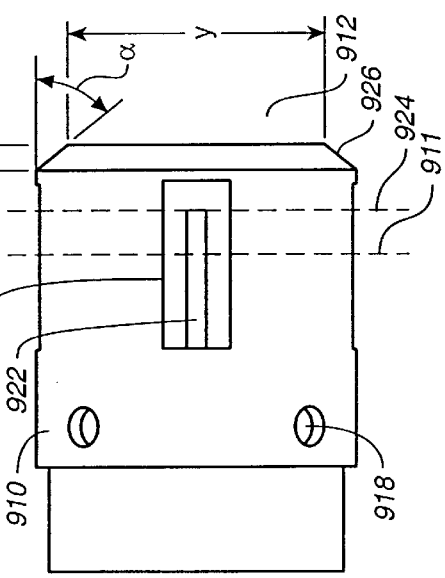
FIG._27B

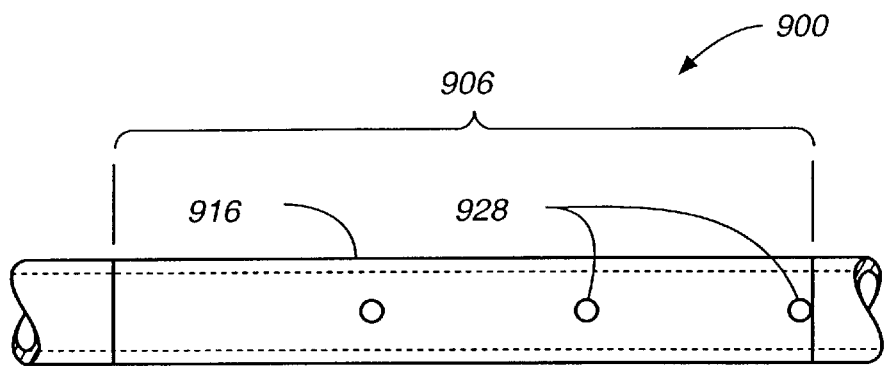
FIG._27D
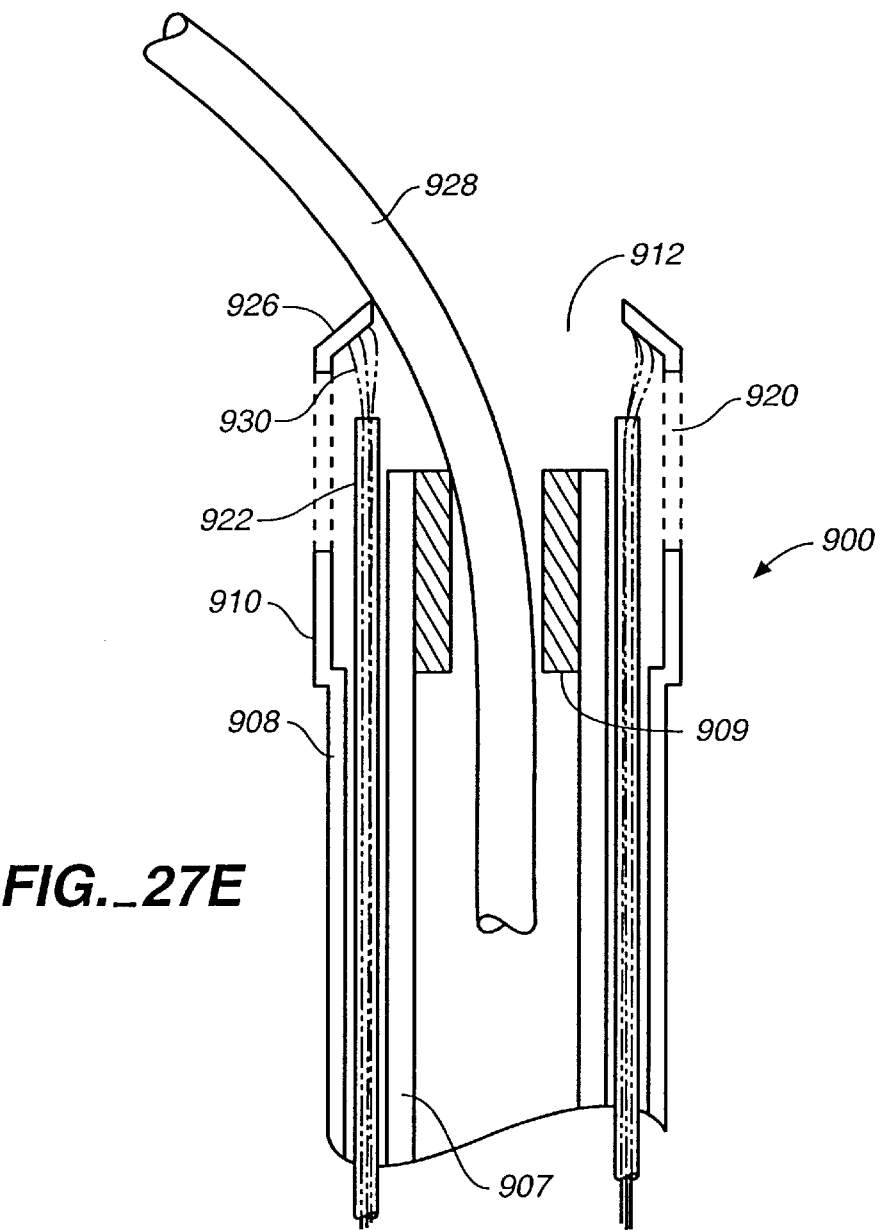
FIG._27E

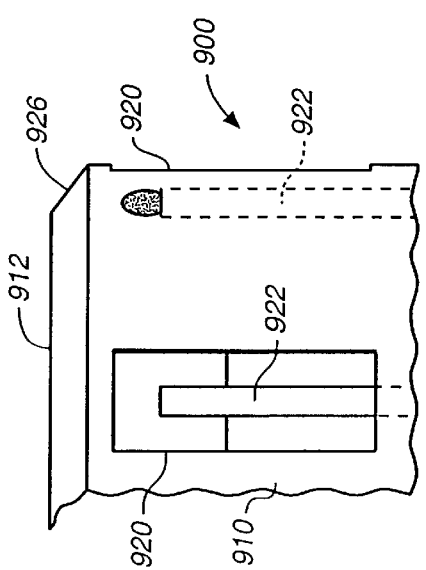
FIG._28A
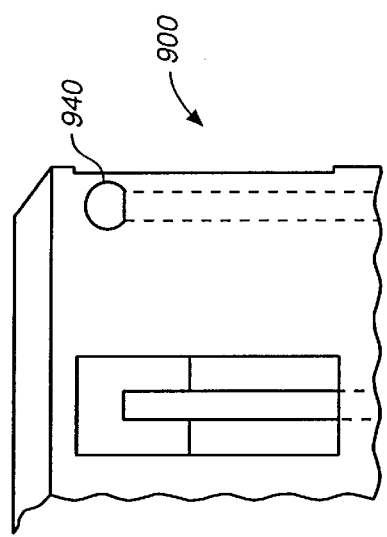
FIG._28B
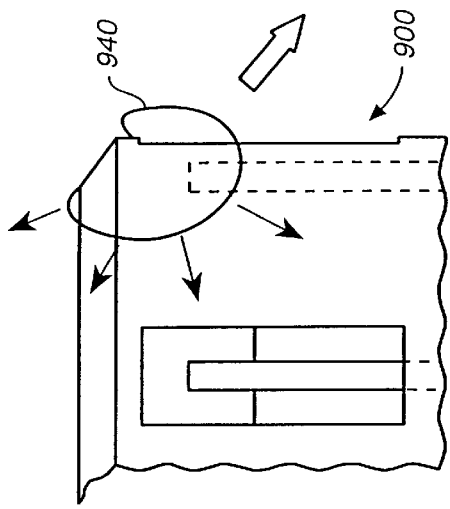
FIG._28C
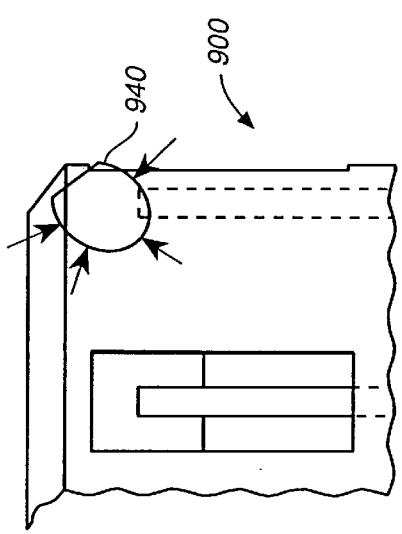
FIG._28D
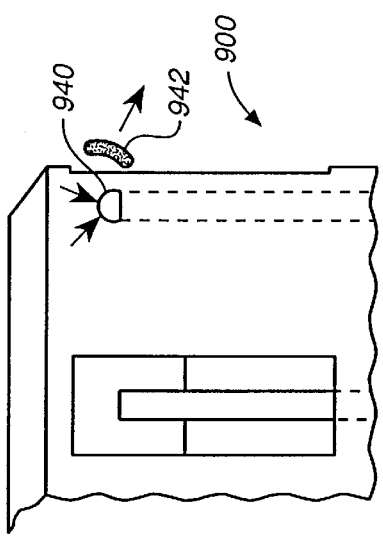
FIG._28E
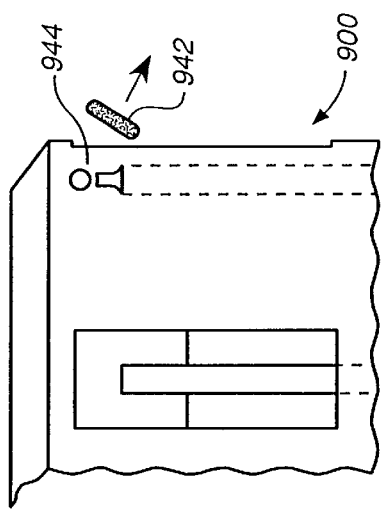
FIG._28F

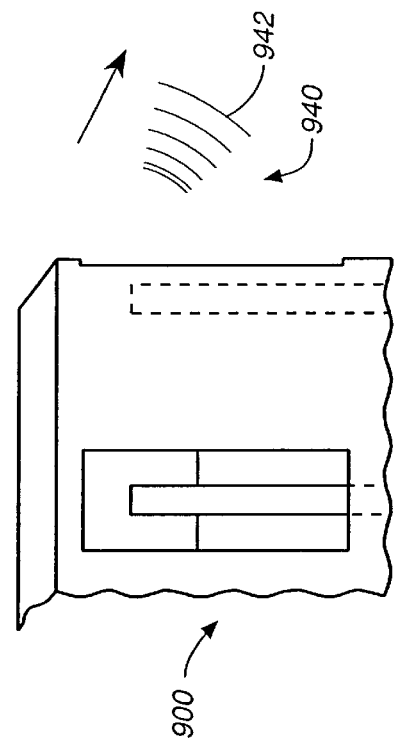
FIG._29B
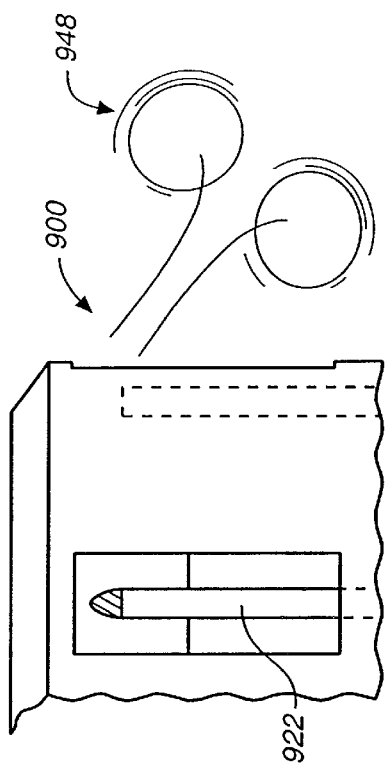
FIG._29D
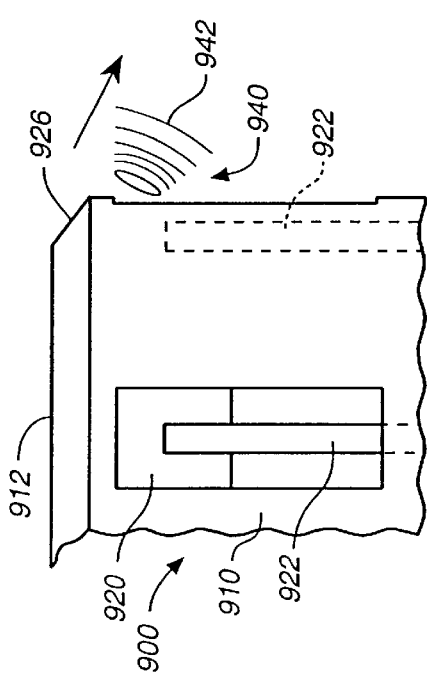
FIG._29A
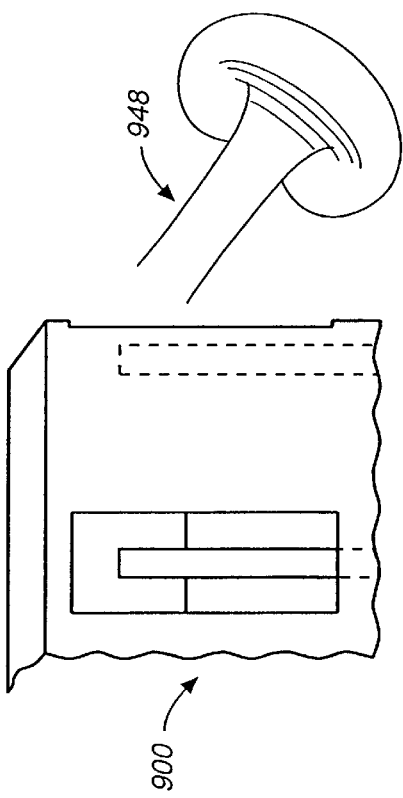
FIG._29C

FLEXIBLE FLOW APPARATUS AND METHOD FOR THE DISRUPTION OF OCCLUSIONS

CROSS-REFERENCE TO RELATED APPLICATIONS

This patent application is a continuation-in-part ("CIP") of U.S. patent application Ser. No. 09/165,435, now U.S. Pat. No. 6,210,400 entitled "Flexible Flow Apparatus and Method for the Disruption of Occlusions," filed Oct. 2, 1998, which is a CIP of U.S. patent application Ser. No. 09/120,598, now U.S. Pat. No. 6,139,543 entitled "Flow Apparatus for the Disruption of Occlusions," filed on Jul. 22, 1998. This patent application is related to U.S. patent application Ser. No. 08/955,858, entitled "PhotoAcoustic Removal of Occlusions From Blood Vessels," filed on Oct. 21, 1997, now abandoned and to U.S. patent application Ser. No. 09/113,700, entitled "Apparatus for Delivering Radiation Energy," filed on Jul. 10, 1998, now abandoned the entireties of both of which are herein incorporated by reference.

BACKGROUND OF THE INVENTION

This invention relates generally to at least partial removal of occlusive material from a body vessel with acoustic phenomena resulting from radiation energy pulses delivered through optical fiber media to the vessel, and, more specifically, to methods and apparatus for generating flow within a body lumen to facilitate disruption of occlusive material and recanalization of the occluded vessel. The term "clot" is used herein to refer to a thrombus, embolus or some other total or partial occlusion of a vessel. The term "emulsify" means to break apart or disrupt by photoacoustic or mechanical or other phenomena into particle(s) smaller than the original occlusive material.

Various embodiments for delivering radiation energy to body lumens for ablative and photoacoustic recanalization have been previously disclosed. However, none of these embodiments is capable of generating fluid flow within the vessel that can be used to improve the degree of emulsification of an occlusion.

Therefore, it is an object of the present invention to provide techniques and apparatus that use pulsed radiation energy to generate fluid flow and/or to perform mechanical work within body lumens.

It is another object of the present invention to recanalize body vessels by disrupting total or partial occlusions using the disclosed flow techniques and apparatus.

It is a further object of the present invention to provide improved techniques for removing obstructions or occlusions from vessels or lumens within the human body, particularly clots from cerebral blood vessels, where that clot has caused ischemia or an ischemic stroke, and more particularly for use in the timely removal of such a clot without causing collateral damage to the vessel.

It is an object of the present invention to provide a method (and apparatus) for attracting occlusive material to the photoacoustic source of disruption so as to potentially enhance the amount and/or degree of emulsification.

It is another object of the present invention to improve flexibility of the distal tip to improve the ability of the apparatus to access remote, tortuous vessel pathways.

Some or all of these objects are achievable with the various embodiments disclosed herein.

SUMMARY OF THE INVENTION

These and other objects are accomplished by the various aspects of the present invention, wherein, briefly and generally, a device having at least one inlet port, at least one outlet port (which may be distal from or proximal to the external environment), and at least one optical fiber having a distal end positioned relative to the ports such that when pulsed radiation energy is delivered to a body vessel via the optical fiber, fluid is caused to pass through the inlet port and to travel towards the outlet port, preferably past the optical fiber distal end. The repetitive formation and collapse of bubbles in the ambient fluid creates this flow phenomenon, which in turn results from the repetitive absorption of radiation pulses by the fluid. This flow phenomenon can be used to enhance the total or partial mechanical disruption or emulsification of occlusions with photoacoustic phenomena (as described in the '858 application) by causing ambient fluid and occlusive material to be drawn towards the recanalization apparatus. The invention can also result in localized emulsification of occlusive material or partial or complete removal of that material from the body. The capability of radiation energy to cause mechanical work to be performed is demonstrated by the present invention.

Multiple fibers can be arranged in such a manner that one or more fibers generate the pumping phenomenon and/or one or more fibers contribute to the clot emulsification by generating the acoustic phenomena described in the '858 application, and/or one or more fibers contribute to mechanical disruption of the clot as disclosed herein, for example. Multiple outlet ports are arranged in various tubing materials in such a way as to maintain a flexible distal tip portion of the apparatus while also maintaining column strength of the distal portion.

The use of very small diameter optical fibers allows the desired pumping to be achieved and acoustic waves to be generated with a relatively low amount of radiation pulse energy, thereby keeping the amount of heat input to the vessel at a low level. Proper thermal management according to the present invention reduces the likelihood of damaging the walls of the blood vessel adjacent the occlusion, which is especially important for the relatively thin walled vessels of the brain in which the present invention has application. Further, it is desirable that radiation pulses not causing the desired fluid flow or not being efficiently converted into the desired acoustic waves be terminated in order to prevent inputting energy that heats the region without doing useful work, as has been described in the related applications.

Additional objects, features and advantages of the various aspects of the present invention will be better understood from the following description of its preferred embodiments, which description should be taken in conjunction with the accompanying drawings.

BRIEF DESCRIPTION OF THE DRAWINGS

FIG. 1 is a longitudinal cross-section of a device for demonstrating the capability of the invention to pump fluid.

FIG. 2 includes front and side partial cut-away views of an apparatus for circulating fluid through the distal end of a catheter.

FIG. 3 is a longitudinal cross-sectional view of the apparatus shown in FIG. 2.

FIG. 4 shows end and partial cut-away views of an apparatus for pumping fluid having multiple corresponding side slots and optical fibers.

FIG. 5 shows the devices of FIGS. 2 and 7 disrupting an occlusion blocking a blood vessel, in cross-sectional view.

FIGS. 6A and 6B show simplified cross-sectional depictions of other embodiments for circulating fluid through a catheter tip.

FIG. 7 consists of cross-sectional views of an apparatus for circulating fluid through a catheter tip having a bundle of optical fibers.

FIG. 8 depicts a cross-section of a variable tip catheter for regulating the amount of emulsification of an occlusion, shown in cross-section.

FIG. 9 depicts a cross-section of an embodiment for circulating fluid past a bundle of optical fibers.

FIGS. 10, 11A and 11B are simplified cross-sectional drawings of multiple-stage pumps used to pump fluid from one location to another.

FIGS. 12A and 12B depict simplified embodiments having multiple fibers for performing the pumping and chewing functions of the present invention.

FIG. 13 discloses a partial cut-away of a multiple fiber arrangement with a spring having a variable coil separation forming the distal portion of the catheter.

FIGS. 14A and 14B illustrate side-views of devices that create sufficient jetting/pumping force to pull the fiber along the lumen of a vessel. FIG. 14C illustrates a variation of FIGS. 14A and 14B, with an angled exhaust port. FIG. 14D illustrates a variation of FIG. 14C. FIG. 14E is a horizontal cross-sectional view of the variation of FIG. 14D, taken along lines 14E.

FIG. 15A depicts a typical construction, in longitudinal cross-section, for a delivery catheter within the scope of the present invention. FIG. 15B shows an end-view of a flush fiber arrangement of an embodiment of the invention disclosed in the '858 application. FIG. 15C depicts an end-view of a distal fiber arrangement of the present invention. FIGS. 15D and 15E detail in longitudinal and radial cross-sections the distal portion of a catheter having a fiber arrangement similar to that shown in FIGS. 12A and 13 within the scope of the present invention.

FIGS. 16A and 16B illustrate in longitudinal and radial cross sections another embodiment of the distal portion of a catheter having a fiber arrangement similar to that shown in FIGS. 15D and 15E.

FIG. 17 depicts a side view and longitudinal and radial cross-sectional views of an embodiment that relies on mechanical action of the distal portions of the catheter to disrupt an occlusion.

FIGS. 18A and 18B illustrate in longitudinal and radial cross sections, respectively, another embodiment of the distal portion of a catheter within the scope of the present invention. FIG. 18C depicts a simplified overview of an alternate embodiment incorporating multiple outlet ports, each port having multiple holes.

FIG. 19A and 19B depict, respectively, longitudinal partial- and radial cross-sections of an "active wire-sized" embodiment.

FIGS. 20, 21A and 21B, and 22A, 22B and 22C depict various marker bands for use with the embodiment shown in FIGS. 19A and 19B.

FIG. 23A and 23B illustrate, respectively, longitudinal partial- and radial cross-sectional views of another embodiment of the invention having multiple side-ports and a beveled tip.

FIG. 24 depicts a marker band for use with the embodiment shown in FIGS. 23A and 23B.

FIG. 25A illustrates in cross-section a "dual lumen" embodiment of the invention in which an "over-the-wire" lumen is separate from the lumen used in generating flow phenomena through the device. FIGS. 25B, 25C and 25D show variations, in radial cross-section, of the structure shown in FIG. 25A.

FIG. 26 illustrates an embodiment in which each optical fiber has a dedicated outer tube in which to generate the flow phenomena associated with the present invention.

FIG. 27A is a side view of a device, in partial cut-away, according to a particularly preferred embodiment of the present invention. FIGS. 27B and 27C are enlarged side and perspective views, respectively, of the distal end of the device of FIG. 27A. FIG. 27D is a side view of a section the device similar to that of FIG. 27A, according to a most preferred embodiment of the present invention. FIG. 27E is a schematic illustration of an "over the wire" use of the device shown in FIGS. 27A–D, according to an embodiment of the present invention.

FIGS. 28 and 29 are schematic illustrations of the operation of a device such as that of FIG. 27A or 27D, according to the present invention. FIGS. 28A–F and 29A–D schematically illustrate such operation over time.

Note that like reference letters and numerals are sometimes used in the drawings and in the following description to refer to like features shown or described elsewhere herein. Also, multiple parts of numbered Figures are sometimes collectively referred to as the numbered Figure (for example, FIGS. 6A and 6B may be collectively referred to as FIG. 6). These conventions are adopted merely by way of convenience, and not by way of limitation.

DESCRIPTION OF THE PREFERRED EMBODIMENTS

The present invention may, in general, be applied to the disruption of material forming a partial or total occlusion of any human vessel but is particularly directed to opening a blood vessel that is totally or substantially blocked to the flow of blood. The related patent applications that have been incorporated by reference (above) disclose these general applications of the present invention, as well as the associated preferred configurations and operating parameters of the associated technology, including, for example, the methods and apparatus for delivering radiation energy from the laser to the optical fibers. Those disclosures apply equally to the present invention. However, it should be understood that the present invention is not limited solely to addressing the disruption of occlusions from blood vessels but may have additional applications in which flow is required or desired to be generated, as will be understood upon reading this disclosure.

The present invention encompasses devices, including catheters, having the ability to "chew" through an occlusion by generating flow through an active distal portion to help draw the occlusion towards the optical fibers (and thus towards the source of the acoustic pressure and shock waves and other forces). These catheters promise to be able to create a hole in an occlusion relatively larger than the outside diameter ("OD") of the catheter or device being used.

Illustrating the types of flow generated by the current invention is the apparatus shown in FIG. 1 comprising an optical fiber positioned inside a capillary tube. Mounting a fiber inside a capillary and firing short duration, low energy, high frequency pulses of absorbable radiation energy creates several useful phenomena. First, generating a series of bubbles 320 inside the sheath portion 322 of the capillary 324 through short-duration, high-frequency, low energy radiation pulses delivered via optical fiber 326 to a fluid medium 328 capable of absorbing said radiation results in a rather violent fluid jetting from the distal end of the capillary in the direction shown by arrows 330. This is believed to result from the expansion of the bubble out of the capillary and into the surrounding media, forcing outwards the slug of fluid that originally occupied the portion of the capillary between the fiber tip and the distal end.

Second, a rather vigorous pumping action was observed during the delivery of pulses of radiation to the fluid, in which fluid shot out of the top of the capillary as indicated by arrows 332. It is believed that this pumping action resulted from the repetitive collapse of bubbles. It is believed that bubble collapse created a zone of low-pressure inside and adjacent to the distal portion of the capillary, which in turn caused surrounding fluid from the vessel to rush back into the capillary to fill the void left by the collapsing bubble. It would appear easier for fluid in the vessel to fill the void rather than fluid already present between the capillary wall and the fiber, because the former would experience less resistance to flow. It is believed that this rapid fluid refilling of the void facilitated the observed flow out of the proximal end of capillary. Capillary action may also have played a role in this first embodiment, although capillary action is not necessary to generate fluid movement, as further explained below.

These pumping/sucking phenomena can.be utilized in a variety of apparatus within the scope of the present invention. One such apparatus is shown in FIG. 2. Outer sheath 334 surrounds one or more optical fibers 338 (three are shown for illustration) asymmetrically arranged in the sheath. The distal tips of the fibers 338 are positioned relative to sheath side slot 336 in such a way that fluid present in the vessel is sucked through side slot 336 and forced out the distal end of the sheath 340. The dimensions of the side slot relative to the fiber size and position are important, since if the fibers are located incorrectly, the pumping/sucking phenomenon is not observed. Satisfactory results are achieved with 12 fibers, having a 50-micron core diameter, a 55-micron clad diameter and a 65-micron polyimide buffer diameter (sometimes referred to as "50/55/65" fibers), aligned side-by-side, with their distal tips even and extending about ⅓ mm (A) into a ⅔ mm-deep slot (A+B), which was ⅓ mm (C) from the distal tip of the 3 French catheter of 0.022 inch inside diameter ("ID"). Note that FIG. 2 (including lengths A, B and C) is not drawn to scale. The slot was horizontally sized to match the width of the 12-fiber bundle.

More particularly, 25 ns pulses (separated by about 200 microsecond delays) of 532 nm wavelength radiation (selected for.its absorption characteristics in blood) at a frequency of about 1 to 10 kHz (with 5 kHz preferred) were introduced through each of the twelve fibers in bursts of 1–3 pulses per fiber with an energy/pulse of about 100 to 300 microJ and an average power of about 300 milliW. A frequency-doubled Nd:YAG laser was used to produce the desired wavelength light. Clot adjacent slot 336 was sucked into the catheter and emulsified via a combination of shock and acoustic waves and turbulence caused by the expansion and collapse of bubbles in the fluid. The emulsified material was then directed out of distal tip 340 and back into the fluid. It is believed that the edge of slot 336 also contributed to the emulsification by tearing the clot as it entered the turbulent region adjacent the optical fiber tips. This mechanical disruption by the edge also resulted from the bubbles hammering the clot against the edge during emulsification. As with all embodiments of the invention, however, the laser parameters, such as for example the pulse duration (for example between 5 and 30 ns), the wavelength, and the pulse energy, may be varied while still producing the desired phenomena.

The sucking motion at slot 336 creates a small vortex which circulates the emulsified material exiting end 340 back towards slot 336 as distance C approaches less than 0.25 mm. This vortex action appears to help keep the clot in contact with the slot once the clot is first sucked in, and thus aids further emulsification.

FIG. 3 is a sectional view of a side-sucking apparatus similar to that shown in FIG. 2. Distal tip 339 containing slot 336 is shown attached to outer catheter wall 334, typically with glue such as cyanoacrylate. The distal end of optional inner lumen walls 354 can terminate evenly with the tip of optical fiber(s) 338, which makes polishing of the fiber and catheter tips during catheter construction easier. As shown in FIG. 3, the volume of the outlet port 340 can be decreased to form annular space 356 by inserting mandrel 350 through inner lumen 352 formed by inner lumen walls 354. Decreasing this volume increases the velocity with which the emulsified clot is expelled from the outlet port 340. Typical materials of construction for the distal tip 339 include HDPE, LDPE, PET, polyimide, or even a metal. Typical distal dimensions are those of a 3 French catheter, although proportionately larger or smaller devices may be constructed depending upon the size of the vessel to be accessed.

An example of a catheter that may be used to deliver the embodiment shown in FIG. 3 as well as other embodiments of the invention to the occlusion site is shown in FIG. 15A. The delivery catheter may comprise two concentric tubes. The outer and inner tubes may comprise multiple sections of decreasing flexibility. As an illustration, FIG. 15A shows three outer sections and two inner, although other combinations may be used. In a 150 cm catheter, for example, outer sections 380, 382, and 384 may be anywhere from about 50–120 cm, about 25–95 cm, and about 3–20 cm, respectively. Sections measuring 95 cm, 50 cm, and 5 cm, for example, produce satisfactory results. A satisfactory proximal outer section 380 comprises a composite of polyimide/spiral stainless steel tubing, with an inner diameter, for example, of 0.030 to 0.040 inch, such as that made by Phelps-Dodge High-Performance Conductor. Section 380 is glued with, for example, cyanoacrylate glue 392, to mid outer section 382 comprising high-density polyethylene (HDPE). The HDPE facilitates joining the more rigid composite proximal outer sheath to the soft distal outer section 384, to which section 382 is glued. Section 384 comprises plasticized polyvinylchloride (PVC) of 60–65 Shore A hardness. The inner tube comprises glued sections 388 and 390 having lengths of anywhere from about 120–140 cm and about 10–30 cm, respectively. Proximal inner section 388 has a material selected to provide the desired rigidity and high burst pressure, such as polypropylene tubing with flex modulus (psi) of between about 200,000 and about 250,000, with about 220,000 being typical. Distal inner section 390 may comprise a LD polyethylene/ EVA blend. A 9% EVA/LD polyethylene blend is satisfactory. To facilitate fluoroscopy, a radiopaque band marker 386, of gold or platinum, may be added to the distal tip of the catheter. The marker band is glued to the distal outer tubing, either outside of the distal outer portion or abutted against the distal edge to be flush with the outer wall. In general, the inner tube materials are chosen for their burst properties, lubricious characteristics and the outer for their rigidity or softness. Similar materials having similar relative properties of flexibility, softness, and lubricity, maybe substituted for those disclosed for the inner and outer tubes. Fibers 394 lie freely between the inner and outer concentric tubes, anchored in place only by the various glue points shown to facilitate increased flexibility. A more rigid catheter may be achieved by injecting more glue at various points between the two tubes of the constructed apparatus. One or more stainless steel or nitinol mandrels 396 may also be inserted between the inner and outer tubes to create more rigidity. The mandrel may be anchored in place by glue points 392 and 398. A mandrel of 0.004 inch diameter may be used, although other diameters or a tapered mandrel would be acceptable, depending on the desired degree of rigidity/flexibility of the construction.

Although not shown in FIG. 15, the body of the catheter may have other constructions. One variation would include a braided inner shaft having a variable stiffness, increasing in flexibility from the proximal to distal ends. Such a variable stiffness braid is available, e.g., from HV Technologies of Trenton, Ga. Another variation includes the addition of a fourth distal section to the outer wall of the catheter to further improve the flexibility of the distal portion of the device, and to help to prevent possible kinking under certain circumstances at the junction of sections 382 and 384, which typically are of HDPE and PVC, respectively. This fourth section may comprise a soft polymer, such as low-density polyethylene (LDPE), which may be connected to the high-density polyethylene section (HDPE) 382 by gluing or melting, and to the distal outer PVC section by gluing. Melting is preferable, if practical, to lower the outside diameter of the combination of the two materials. Satisfactory constructions that minimize or avoid kinking at the section 382–384 junction have been made by replacing the distal 5 cm of the HDPE section 382 with about the same length of LDPE. For such a construction, the 0.004-inch-diameter mandrel, typically of nitinol, preferably would extend to the junction of the HDPE/LDPE section.

An alternate construction of the distal portion of the body sheath would be to strengthen the transition between the HDPE/PVC or LDPE/PVC junction on the outer wall, by, e.g., adding shrink-wrap over the joint and 1–2 cm on either side of the joint, or adding shrink-wrap to the entire length of the device, the shrink-wrap terminating 1–2 cm distal of the joint to be supported. Other modifications will be understood, and thus will not be further addressed herein.

Although dimensions for the materials for the inner and outer walls of the catheter can be chosen based on availability, desired flexibility, strength and resiliency, for example, acceptable dimensions for a 3-French device are about 0.022/0.026 inch inner/outer diameter for the inner lumens and about 0.031/0.035 inch inner/outer diameter for the outer lumen, with a typical marker band having about 0.034/0.037 inch inner/outer diameter and a length of about 1 mm.

A lubricious polymer coating, such as a hydrophilic coating or silicone may be used to increase the ease of navigating the catheter through the guiding catheter and desired body lumens, and if introduced on the interior catheter walls, may enhance the ability to track over an associated guidewire.

In general, catheter construction is well known and thus will not be described in great detail. Within the scope of this inventions are catheters that possess an appropriate balance of flexibility, stiffness, and longitudinal strength, among other factors, to be useful in reaching occlusive material with a vessel, particularly a cerebral blood vessel, and treating the obstructed vessel in the manner previously described. In brief, after inserting the desired number of optical fibers and the inner tubular member into the outer tubular member, the distal location of each fiber is adjusted so that the fiber distal ends occupy the desired distal geometry. For example, the fibers can be sequentially arranged in the same order as in the planar array of the connector (not shown) to the energy source, so that they occupy the geometry shown in FIG. 15B (as an example of a configuration that could be used for the embodiments disclosed in the '858 patent application) or in FIG. 15C (that would correspond to the embodiment shown in FIGS. 2 and 3). Arranging the fibers in this manner ensures that the energy source, such as a laser, which supplies energy to the fibers via the connector, supplies energy to the desired fiber(s) in the desired order or pattern. To accomplish this fiber arrangement, a light source, such as a marker laser, is used to identify which fiber distal end corresponds to which fiber end positioned in the connector. As each fiber is sequentially identified, its distal end is temporarily held in position until all fibers have been identified and located. The fibers are then glued into position. Fibers can be held temporarily in position by inserting each distal end into an alignment block having a series of holes, each hole corresponding to a particular fiber. The block holds the fibers in position until they are glued.

Fluid such as biocompatible coolant (e.g., saline), radiographic agent or thrombolytic agent may be introduced through inner lumen 352 during emulsification. Or, alternatively, fluid may be aspirated through the lumen to remove emulsified material from the body.

FIG. 4 depicts a catheter in which multiple fibers are mounted approximately equidistant around the circumference of the catheter, each fiber having its own inlet port in the side of the catheter tip. When the fibers are fired individually with pulsed radiation, as described herein, each fiber creates its own pumping action through its corresponding side hole 358. As the position of the distal tip of an optical fiber moves up its side hole towards the distal tip of the catheter, the pumping phenomenon tends to change from sucking through the side hole to blowing out of the side hole. When the tip of the catheter is located in fluid adjacent the occlusion, such an arrangement of fibers can cause the end of the catheter to gyrate around the clot, thereby increasing the degree of emulsification of the clot relative to a catheter that remains relatively stationary. Gyration can be improved by decreasing the number of fiber-and-slot combinations and increasing the number of consecutive pulses to each fiber, to permit the catheter tip to overcome inertia and to move through the fluid across the face of the clot. Gyration, however, is minimized if the catheter tip is located within an occlusion, due to high damping forces.

FIG. 5 shows how the device depicted in FIGS. 2 and 3 may be used in a blood vessel 360 having a thrombus 362 and stenotic plaque 364. For the device shown in FIG. 2, the catheter can be punched through the thrombus while the optical fibers are dormant until the catheter reaches the distal position shown. Pulsed radiation is then delivered down one or more optical fibers 338, causing the thrombus to be sucked into slot 336, emulsified, and then ejected 366 through the catheter distal tip. During the procedure, the catheter tip is slowly withdrawn through thrombus 362, thereby revealing new thrombus to the catheter tip for emulsification. The speed of withdrawal is dependent upon the character of the thrombus being emulsified and the geometry of the fibers and slot. The catheter should not be withdrawn so fast that the catheter's ability to chew through the thrombus is overwhelmed and the catheter tip becomes clogged, thereby adversely affecting the degree of emulsification. While FIG. 5 depicts thrusting the catheter tip of FIG. 2 entirely through the thrombus before emulsification begins, it may also be used to emulsify thrombus by simply causing the catheter tip to approach the proximal portion of the thrombus with the optical fibers already firing into the ambient fluid so as to create the desired acoustic phenomena and avoid direct ablation.

Another apparatus that exhibits the pumping/sucking phenomena is shown in FIG. 6A. Instead of a side-sucking apparatus, however, examples of which are shown in FIGS. 2 and 3, FIG. 6A depicts an apparatus that sucks through distal port 376 and discharges through rear ports 372. Optical fiber 368 is positioned within lumen 370 such that the distal tip of fiber 368 is located between distal opening 376 and rear openings 372, and within sufficient distance of distal opening 376 such that pulses of radiation delivered through optical fiber 368 cause fluid adjacent the distal port 376 to flow into the catheter and out of the exit ports 372.

The tapered portion of FIG. 6A has the advantages over a wider intake port, for example, up to about 400 microns and shown, for example, in FIG. 7, of increasing the ultimate velocity of fluid-intake through the distal opening 376 and of minimizing the possibility of permitting clot to by-pass the emulsification zone at the optical fiber tip(s). A typical necked portion of tubular member 370 can be formed, for example, by gently pulling heated PET tubing until it elongates and creates a portion of narrower diameter, and then cutting the narrower portion to form the distal opening 376. Distal openings of from about 0.008 to 0.012 inch or larger can be made from 0.029-inch-ID PET tubing. The necked portion typically extends over about 1 mm.

FIG. 6B depicts an alternative method of narrowing the distal inlet portion of a tubular member. Instead of necking the member, a simple doughnut-shaped object with desired inner diameter is glued to the distal end of the member. Such object may be of any suitable material, such as polyimide or polyethylene tubing or some other polymeric material.

For front-sucking devices such as shown in FIGS. 6A and 6B, the positioning of the distal tip of the optical fiber 368 relative to the distal opening 376 becomes more sensitive as the distal opening diameter increases. That is, the wider the opening, the smaller must be x. A typical dimension between the fiber tip and the plane of the distal port 376 (x) for a 0.008-inch-wide distal port and a 50-micron-diameter optical fiber and the operating parameters disclosed herein, including energy per pulse of about 200 microJ, is between about 100 and 350 microns. However, as the distal port diameter increases to about 0.015 inch in diameter, the tolerance range decreases to between about 100 to 150 microns, or 0.004 to 0.006 inch.

It is believed that this increase in positioning sensitivity for wider distal ports is related to the ability of a generated bubble to fill the space between the walls of the distal opening and thus to generate the pumping force. That is, for the same operating conditions and bubble volume, a bubble spanning the distal port would have a smaller depth (and thus a smaller range of x) for a tube of larger cross-sectional area than a bubble filling a tube of smaller cross-sectional area. Since the size of a bubble also depends upon the amount of energy delivered to the absorbing fluid, however, the sensitivity in relative positioning between the fiber tip and the distal port can be decreased by increasing the energy per pulse, and thus the size of the bubble generated per pulse.

FIG. 7 depicts another embodiment of the invention, in which a bundle of multiple fibers 400 (with six optical fibers 402, for example, together with a central lumen 404 for delivering fluid (for example, coolant) to, or aspirating fluid from, a blood vessel) is shown positioned within an outer sheath 406 between the one or more side slots 408 and the distal opening 410. If the fiber bundle 400 is positioned centrally within sheath 406, as shown, it may be secured in place with a glue plug 412. When pulses of radiation are delivered through the optical fibers in sequence to a fluid capable of absorbing the radiation, such that a series of transitory bubbles are first generated and then collapse, flow is created from the distal opening 410 past the distal end of the fiber bundle 400 and out of the oval side slots 408, as shown by the arrows in FIG. 7. Typical dimensions for this construction include 5 mm for the portion of the catheter between the distal opening 410 and the distal edge of the side slot 408; typical side slots 408 can be between 5 mm and 10 mm; for a fiber bundle of outside diameter of between 0.01 and 0.02 inch, a catheter tip diameter of about 1 mm (or 0.04 inch) was used. For the construction described herein to generate flow as described, the dimension labeled x between the distal tip and the tip of the optical fibers was between about 0.004 and 0.006 inch. Typical materials of construction for the sheath are HDPE or PET or polyimide. As shown, sheath 406 optionally may comprise part of catheter 401, which serves as the delivery vehicle for positioning the apparatus adjacent an occlusion. However, catheter 401 is not necessarily required, as long as some other sufficiently rigid and sufficiently flexible delivery means, such as the fiber bundle 400 itself, is available.

A typical construction for the fiber bundle comprises a proximal portion having a spiral-wrap stainless steel coil sandwiched between polyimide tubings, together with an outer layer of shrink-wrapped PET as desired, and mid and distal portions having successively fewer layers of polyimide. The desired distal portion of acceptable outside diameter of between 0.01 and 0.02 inch (0.018 inch being preferred) comprises optical fibers positioned with cyanoacrylate glue between either two concentric polyimide tubes or one inner polyimide tube and an outer platinum coil. Coolant or other fluid may be introduced through the inner polyimide tubing as desired or emulsified material can be aspirated.

The apparatus shown in FIGS. 6 and 7 may be used to emulsify an occlusion, by drawing the occlusion through the distal opening towards the optical fibers and emulsifying it in the manner described herein and as shown in FIG. 5. More specifically, the apparatus depicted in FIG. 7 is shown in FIG. 5 attacking the proximal surface of occlusion 362. Emulsified clot 366 is shown ejected from side slots 408 after being emulsified through a combination of shock wave and forces generated by the expansion and collapse of transitory bubbles, all as described in the earlier applications. A guidewire (not shown) extending beyond the distal end of the apparatus may be used when it is desired to push the apparatus forward through the occlusion. The user should take care not to push the apparatus of FIGS. 6 and 7 too quickly through the occlusion during emulsification, so as to avoid overwhelming the apparatus.

The apparatus depicted in FIG. 8 addresses this potential issue by regulating the amount of clot being emulsified in the apparatus and thus helping to prevent the optical fibers from being overwhelmed and the device from plugging. It comprises a variable size exit port (created by a loosely coiled spring) that permits the apparatus either to suck or repel the clot surface. A stainless steel or platinum spring 420 is glued to the distal end of the main catheter body 422. To the distal end of spring 420 is glued a sheath 416 of polyimide or HDPE. Single optical fiber 402 is positioned as shown such that the sheath 416 covers its tip. The tip of the optical fiber is positioned relative to the distal end of the sheath tip such that flow is generated through distal opening 414 when radiation pulses are delivered through the optical fiber 402 to the site of the occlusion. Lumen fluid and gelatinous clot are sucked through frontal inlet portion 414 of the distal catheter tip 416 toward the optical fibers and emulsified as described herein, and then are ejected through the open portion 418 of the spring 420. As the clot is pulled into the front portal 414, however, the clot presses against the outer surface of the distal sheath 416 of the apparatus, slightly compressing the spring 420. The resiliency of the spring then biases the distal sheath 414 away from the clot, thereby decreasing the amount of clot being pulled into the device to be emulsified. As the device is moved away from the clot, the suction caused by the absorption of radiation energy into the lumen fluid again draws the clot towards the device and so continues the emulsification. In this manner, the user is aided in controlling the rate of emulsification through these ongoing minor adjustments of the device. Although only a single fiber is illustrated in FIG. 8, multiple fibers or a fiber bundle would also work for this embodiment. Again, although this embodiment is shown mounted on a catheter 422, if no fluid needs to be delivered through a central lumen to the activity site, as in most of these embodiments, then a catheter is not required to deliver the apparatus to the occlusion. Instead, any appropriate, sufficiently flexible means such as a simple wire, may be used to deliver the active portion of the apparatus to the occlusion. A typical outer diameter of this apparatus would be between about 0.010 and 0.020 inch, with a preferred outer diameter of about 0.018 inch. Portion 416 can be constructed out of any appropriate material such as polyimide.

Spring 420 should have a spring constant k sufficient to prevent the tip of the fiber 402 or fiber bundle 400 (as in FIG. 7) from directly contacting the clot as the clot gently presses against the outer surface of the distal sheath 416, so that a distance is ideally maintained between the tip of the fiber or fiber bundle and the outer edge of the distal sheath. This distance may approximate 0.004–0.006 inch for a 1-mm-diameter sheath and optical fiber bundle of between 0.01 and 0.02 inch outside diameter. If the spring is so weak that the spring permits the optical fiber tips to travel beyond the spring/distal sheath arrangement, then this variable tip, spring-loaded apparatus can lose its advantage of controlling the rate of emulsification and its ability to pump. A satisfactory spring for this purpose may be made by winding about 140 kpsi Ultimate Tensile Strength stainless steel or platinum wire of about 0.002 to 0.003 inch diameter around a mandrel, and then stretching a section so that between about 5–10 windings occupied about a 5 mm length. Other materials and dimensions which would produce satisfactory springs to serve the purposes described may be used as well or alternatively.

The apparatus shown in FIG. 9 can establish either forward or reverse flow depending on the position of the tip of the fiber optic bundle 400 relative to the distal opening 426. When the fiber optic bundle 400 is positioned within about 0.004 to 0.006 inch from the distal opening 426 of the HDPE 1-mm diameter sheath 424, suction is developed through opening 426 and fluid is expelled through rear opening 428. Alternatively, if the distance between the distal tip of the fiber optic bundle 400 and the distal opening 426 is either increased or decreased outside of the 0.004 to 0.006 inch range, the flow mechanism reverses, and the device develops suction through opening 428 and expels fluid through distal opening 426. The same would be true for differently sized devices, as long as the bubble size produced by the fiber/energy/operating conditions combination were sufficiently large.

Preferred constructions of catheter tips for preferred single-stage pumping/sucking/emulsifying embodiments of the present invention have been described. FIGS. 10, 11A and 11B depict multi-stage embodiments within the scope of the present invention. Multiple single stages 369 of the type depicted in FIG. 6 are connected end-to-end to create a multiple-stage fluid pump of FIG. 11A. Fluid sucked through distal end 430 and into the first unit as a result of radiation delivered to optical fiber 431 is then sucked from the first unit through opening 432 and into the second unit by the action of optical fiber 433. Fluid in the second unit is then sucked through opening 434 and into the third unit by the action of optical fiber 435, and so on. In this way, fluid passes from distal opening 430 down the length of the multistage pump. FIG. 10 depicts each stage separated with a simple doughnut-shaped plate 442 rather than a nozzle 374 (as shown in FIG. 6A). Firing of the various fibers should be controlled so that radiation is delivered to each fiber tip only when the tip is immersed in fluid. This can be assured by priming the apparatus before use with fluid similar to the fluid in which the distal port is immersed, or firing the fibers only when the fluid pumped from the vessel reaches each fiber. FIG. 11A depicts the multistage pump with each stage having exit slots 446. FIG. 11B is depicted with no exit slots. Instead, elements 444 are necked portions of the outer tubing in which the fiber tips are positioned to generate the sucking/pumping force. Such necked portions can be formed by heating and collapsing the polymeric tube 448 around a central mandrel, and then, after cooling, removing the mandrel to leave the tube with multiple collapsed portions. The fibers are then positioned and secured inside each necked portion to form the multistage apparatus.

The apparatus of FIGS. 10 and 11A are depicted housed inside optional tubular vessel 438 sealed on its distal end with impervious webbing 440. Tube 438 would contain any fluid pumped from the vessel in which the apparatus is positioned and prevents the pumped fluid, including any emulsified clot, from passing back into the vessel. Further, while each stage depicted has side slot in fluid communication with tube 438, such slots are not required.

Optionally, each stage could be separated by a valve—e.g., a leaf valve or a ball valve (not shown)—to prevent backflow from stage to stage or to direct or rectify fluid flow in a particular path. Such valves could also be used on the single stage versions, for example to seal off the exit port as the fiber was firing to ensure that fluid was pumped into the device only through the inlet port.

The pump head developed by a device such as that shown in FIG. 6A can be determined by positioning that apparatus with its exit ports 372 inside the tube-and-webbing arrangement shown in FIG. 11A. Fluid pumped from a source will slowly fill the tube until the height of the fluid equals the pressure developed by the pumping mechanism. A single optical fiber has generated heights of water equivalent to between 0.25 to 0.5 psig. In addition, even for a non-optimized set-up, pumping rates in the order of about 0.2 cc/second were observed for an average power of about 300 milliW.

Traditionally, pumping or suction of fluid within the body has been achieved by having an external source of suction or pressure generate a corresponding negative or positive pressure inside the body cavity. The fluid jetting/suction phenomenon of the present invention, however, illustrates how fluid can be pumped inside the body cavity (or in any other remote source of fluid) using radiation energy from a radiation source remote from the point of fluid flow. Pumping fluid using the methods described is believed to result in relatively high, albeit fleeting, pumping pressures of perhaps several hundreds of psig, for example, from about 100 to about 200 psig. Such pressures were previously unattainable in the body without risk of injury.

FIGS. 12A and 12B show various fiber arrangements for minimizing the ability of non-emulsified clot sucked into the apparatus through the distal opening from escaping emulsification before being ejected through the side slots. Multiple fiber arrangements have the advantage of permitting the various functions of sucking and chewing/emulsifying to be performed by different fibers. For example, in FIG. 12A, fiber 462, positioned relative to the distal opening 464 as described above for FIG. 6A, creates the pumping/sucking force drawing fluid and clot towards the distal opening 464. Fiber 460, positioned flush with, or slightly past distal opening 464, performs the function of emulsifying the clot but is incapable of contributing to the pumping phenomenon because of its location. This initial emulsification at the distal opening by fiber 460 helps to increase fluid flow through the opening, which in turn helps to cool the distal end of the apparatus. Of course, fiber 462 may also contribute to the actual emulsification in addition to creating the fluid flow, because of the acoustic phenomena being generated by the repetitive pulses of radiation energy.

Fibers 466 perform further emulsification of clot particles as they travel through the apparatus towards the side slots 468. However, if the fiber tips are longitudinally spaced too closely together, then it may be possible that during the inactive period between pulses of treatment laser radiation, clot particles that could benefit from further emulsification might actually avoid further emulsification because of the fluid velocity created by the geometry and operating conditions of the apparatus. Thus, fiber tips ideally are positioned longitudinally relative to one another such that clot particles are incapable of bypassing all emulsification zones between consecutive pulses of radiation. For a construction of the type shown in FIGS. 6 and 12 having a 0.012-inch-diameter distal opening and a nominal 0.022-inch-diameter inner tube and a typical energy level as described herein, fluid velocities in the order of 200 cm/sec have been observed. For a period between pulses of, for example, 200 microseconds, typical fiber tip spacings are about 100–500 microns, depending on the duty cycle. That is, the longer between consecutive pulses, the farther apart the fiber distal tips need to be to minimize the chance of a particle avoiding all emulsification zones.

FIG. 13 discloses a variation of the embodiment shown in FIGS. 8 and 12A. Spring 470, shown in partial cutaway to reveal the distal portion of the apparatus, is attached to the distal end of a suitable catheter 472. The distal portion of spring 474 is tightly wound, and serves as a flexible tip to permit the device to navigate the tortuous path of small diameter vessels in order to approach an occlusion. The proximal portion of spring 476 has a larger coil separation than the distal portion 474, and thus provides exit ports between adjacent coils, through which fluid and particles that are sucked in through distal opening 478 and emulsified can be ejected.

As shown, the spring 470 has a tightly wound distal portion 474 and a more loosely wound portion 476. Fiber 480 lies within an annulus created by the windings or coils of spring 470, and is positioned therein such that pulsed radiation delivered through fiber 480 into the ambient fluid causes the fluid to be pumped through the distal opening 478 and out between the spaces between the spring windings in spring portion 476. Fiber 482 also lies within the annulus created by spring 470, and is positioned such that its distal end is substantially flush with the distal opening 478 of the spring 470. Fiber 482 thus does not contribute to the pumping action. However, as fluid and occlusive material approach the device due to the sucking/pumping action caused by fiber 480, both fibers help to emulsify portions of the occlusion. Furthermore, consistent with the discussion of FIGS. 12A and 12B, other longitudinally offset fibers can be positioned within the annulus created by spring 470 to ensure complete emulsification. The spring described in connection with FIG. 8 would also be satisfactory here. The desired coil separation could be achieved by inserting two razor blades into the spring between coils a certain desired distance apart, and stretching that portion of the spring until the desired linear coil density is reached.

Central lumen 484 is optional, and can be used to deliver fluids such as radiographic contrast agent or coolant to the site of the occlusion. Since all embodiments of the invention rely on the absorption of select wavelength radiation energy into colored fluid such as blood, however, delivering fluid to the area of emulsification that alters the color of the vessel fluid through dilution or dissipation, may interfere with the absorption characteristics of the environment of the occlusion. Small delays in the emulsification process thus may be necessary to permit the area surrounding the environment to reperfuse with fluid, such as blood, that is capable of absorbing the wavelength light being used, if fluid is introduced to the site of the occlusion through the central lumen. Alternatively, a tinted fluid compatible with the ambient conditions of the occlusion, may be introduced, so that absorption of the radiation energy will be minimally affected by the introduction of other fluid.

FIGS. 14A and 14B disclose another embodiment of the invention. As shown in FIG. 14A, cylindrical structure 486 is glued to the distal end of optical fiber 488. Examples of dimensions of tube 486 for a 50/55/65-micron diameter optical fiber (50-micron core diameter, 55-micron clad diameter and 65-micron polyimide buffer diameter) are about 2 mm in length and between about 0.008 to 0.020 inch in diameter, with the distal optical fiber tip anchored within about 250 microns of the distal opening of cylinder 486. Delivering short-duration, high-frequency, low-energy, pulsed radiation, as described herein, to fiber 488 causes fluid to be sucked through distal opening 490 and pumped out of proximal opening 492, creating a force that tends to pull on fiber 488. The pumping or jetting action at the distal end of fiber 488 causes the fiber to track upstream in a blood vessel, for example, as the fiber is paid out. Speeds estimated to be about 10 cm/sec were observed using a single fiber. If the device is placed downstream of an occlusion in a vessel, pulsed radiation delivered to the fiber causes the device to approach the occlusion and cause emulsification as the clot passes within the emulsification zone of the fiber.

A number of these devices can be bundled together, as shown for example in FIG. 14B. When pulsed radiation is delivered to different ones of fibers 494, directional pull on the apparatus is produced as a result of a non-central-axial force vector, created by the non-centralized longitudinal thrust of the apparatus. The direction of the pull depends on the geometry of the fibers and which fiber is fired. This force vector can be controlled to influence the direction of the path of the device or how the apparatus tracks across the face of an occlusion and causes emulsification of different areas of the occlusion.

FIG. 14C depicts a variation of the embodiments shown in FIGS. 14A and 14B, having an angled exhaust port 497 at the proximal end of the tubular construction 495. Such an angled exhaust port can be constructed by removing an angular portion of the tubing with a scalpel, without severing the tube, and then folding and gluing the two remaining connected sections. Several of these angled tubes can be connected together, in the manner similar to that shown in FIG. 14B. Such a device exhibits rapid angular movement due to the redirected flow through the angled exhaust port 497. Fiber 494 preferably is mounted along the side of tube 495 opposite from the exhaust port 497 (and, optionally, aligned with the center of optional port 499). Otherwise, if the fiber spans the internal portion of the exhaust port, it can contribute to clogging during the disruption of occlusive material. Such an embodiment may be useful in ensuring more thorough disruption of occlusive material across a substantial portion of the surface of the occlusion. It also provides substantial translational forces for motion control of the device.

FIGS. 14D and 14E show a useful variation of the embodiment of FIG. 14C, wherein the tube 495 is allowed to rotate about the fiber 494, as further described below. In this variation, the exhaust port 497 is positioned along a central, horizontal port axis B which is perpendicular to the central longitudinal axis A of tube 495. Preparation of this construction is much as described above in relation to FIG. 14C, although the angular portion cut out of the tube 495 will be larger to produce the desired right-angle construction. Fiber placement in this variation differs from that shown in FIG. 14C, as illustrated in FIG. 14E. That is, rather than being located along a side of the tube 495 opposite the exhaust port 497, as preferred in the embodiment of FIG. 14C, the fiber 494 is located along a side of the tube 495, rotationally offset from the center C of the exhaust port 497 by about 90 degrees.

Fiber 494 lies within two bearing devices 800 and 801, for example, tubular housings, which are fixed to the interior wall of the tube 495. Preferably, one bearing 800 is located near the distal end of the fiber 494 within the tube 495, while the other bearing 802 is located near the proximal end of the tube 495. These bearings house the fiber 494, while allowing tube 495 to rotate freely with respect to the longitudinal axis of the fiber. Nut-like devices 804 are fixed to the fiber and positioned at the distal-most end of bearing 800 and the most proximal end of bearing 802. By way of example, the nut-like devices may be small fixing tubes surrounding and glued to the fiber. These nut-like devices 804 maintain the fiber 494 within the bearings 800 and 802, and maintain the distance between the distal tip of the fiber and the distal opening 490 of the tube 495.

According to this embodiment, when the fiber 494 is energized as previously described, fluid is sucked through the distal opening 490 and pumped out through exhaust port 497, as schematically shown by the directional arrows in FIG. 14D. This fluid motion causes the tube 495 to rotate around the fiber, as described above and as schematically shown by the directional arrow in FIG. 14E. As the fiber 494 is located along the side of the tube 495, rather than along the central longitudinal axis A, an "off-axis" force is created by the fluid motion. This off-axis force causes rapid rotation of the tube section, which may enhance clot disruption.

Exemplary dimensions for the tube 495 include a length of about 0.040 inch and an inner diameter of about 0.0156 inch. The distance between the distal end of the optical fiber 494 and the distal end or opening 490 may be about 0.005 inch. The optical fiber 494 may be placed about midway between the exhaust port 497 and the opposite side of the tube 495 along the side of tube 495. For example, the fiber may be placed such that the distance x shown in FIG. 14E is about 0.00795 inch. Additionally, the fiber may be placed along the side of the tube 495 such that the distance y is about 0.002 inch.

FIGS. 15D and 15E are schematics of the distal end of the catheter shown in FIG. 15A (previously described) having a configuration with an active tip portion similar to that shown in FIG. 12A, but having a single "pumping" fiber 391 and three "chewing" fibers 394. Tube 389, having a length of approximately 1 mm and an inner diameter of from about 0.014–0.018 inch, is glued between the distal inner walls 390 of inner diameter of from about 0.020 to 0.029 inch. Tube 389 has a 0.35 to 0.5 mm-deep notch 393 cut out of one side. The major distal portion of "pumping" fiber 391 is located between inner catheter wall 390 and outer catheter wall 384. The minor distal portion of fiber 391 passes between the joint of inner walls 387 and 390 and is secured to the outer surface of tube 389 such that its distal tip is located about 0.25 mm from the distal-most edge of tube 389, which is substantially coplanar with the distal-most catheter plane 391 a. Tubular portion 387 (e.g., of low-density polyethylene) is glued on the distal ends of wall 390, so that its distal edge is flush with the distal edge of tube 389. Marker band 386 is added to facilitate visualization of the apparatus inside the body during use. The overall distal diameter of the construction is about 1 mm or 3 French.

Side slot 397 is formed by skiving both the inner and outer walls of the catheter, and serves to eject from the apparatus fluid and emulsified material pumped in through tube 389 as a result of the action of fiber 391. The slot, typically of 3 to 10 mm long, may begin anywhere from 1 to 10 mm from the distal tip of the catheter. As the distance between the distal tip of the catheter (and thus of the fiber 391) and the slot increases, however, less pump head exists to eject pumped fluid and emulsified material. More than one slot may be used, as desired. Minimizing the spacing between fiber 391, tube 389 and tube 387 can improve the pumping performance of fiber 391.

Fibers 394 can be positioned approximately flush with the distal tip of the catheter construction, and thus may not contribute to the pumping action. Instead of being secured with a glue plug as shown in FIG. 15A, however, fibers 394 are anchored to the side wall of either portion 387 or 390 using a small patch of glue 395. Thus, if fibers 394 are positioned such that they both emulsify and create a sucking force, particulates sucked into the apparatus by fibers 394 can travel between the inner and outer walls and be ejected through side slot 397. Alternatively, the emulsified particulates might potentially be trapped between the walls and withdrawn from the patient after recanalization.

Although only one pumping fiber and three chewing fibers are disclosed in this embodiment, other combinations of fibers are possible, including multiple pumping fibers. Radiation pulses are distributed between the various fibers as desired. Two examples would be to evenly distribute groups of three pulses of energy with a 0.33 duty cycle between the four fibers, so that each fiber receives 25% of the average energy delivered to the site of the occlusion. Alternatively, the average energy can be delivered evenly between the chewing and pumping fibers, so that each set of fibers receives about 50% of the energy delivered. In the fiber arrangement disclosed in FIGS. 15D and 15E, for example, a pulse train could be delivered to the single pumping fiber after every delivery to one of the three chewing fibers, so that for every pulse train received by a particular chewing fiber, the pumping fiber would receive three. Distributing radiation pulses in this manner will help to increase the continuity of the pumping and emulsification actions, and will reduce periods of inaction of the two. In addition, since the pumping fiber alone will tend to attract fluid/particles to the device, and the chewing fibers alone will tend to repel fluid/particles from the device, the pumping and chewing fibers can be controlled to address potential clogging. In other words, if the device starts to become overwhelmed with occlusive material, the pumping fiber could be turned off while leaving the chewing fibers on, so that the material would be emulsified and/or repelled to clear the unit for further pumping/disruption.

Alternatively, the device could be used to probe the vessel for the location of the clot with only the chewing fibers operating, and then based on the duration information provided by the bubble feedback system (bubble duration being less for clot than for blood), the pumping fiber could be turned on once the device reached the vicinity of the clot. In other words, as described in the related patent applications which have been incorporated by reference (above), the pumper and/or the chewer fibers could be controlled using bubble feedback information to avoid inefficiently introducing heat into the system.

FIGS. 16A and 16B depict an alternative construction to that shown in FIGS. 15D and 15E for a similar fiber arrangement. Nozzle 371 may be a solid piece of polyether block amide (such as PEBAX 7233, made by AtoChem) with Shore D hardness of about 70, or some other similar, suitable polymeric material. Nozzle 371 is extruded as a tube with inner diameter equal to the widest portion of the final nozzle construction, and with multiple lumens 369 created within the walls of the PEBAX construction. Because of this construction, the PEBAX cannot be too soft, otherwise the lumens cannot hold their form and collapse. These lumens ultimately will house optical fibers 391 and 394. The nozzle is created by gently heating the PEBAX material and collapsing it around a mandrel with an outside diameter equal to the desired inner diameter of the distal portion of the nozzle. Typically, a nozzle fitting a 3 French, 1-mm-OD catheter has a proximal inner diameter of 0.022 inch, a distal inner diameter of 0.018 inch, a length of about 2 mm, and a 1-mm-long necked portion. Nozzle 371 is secured to the inner wall of the catheter with cyanoacrylate glue. "Pumper" fiber 391, present between inner and outer catheter walls, as previously described, is positioned in one of the lumens 369 of nozzle 371 and terminates about 250 microns from the distal plane of the apparatus, such that it creates a pumping motion, as described herein, that results from pulsed radiation energy. The removed portion 375 of nozzle 371 permits the fiber tip 373 of "pumping" fiber 391 to extend slightly into the inlet port 379. Each of "chewing" fibers 394 is positioned in the pattern shown, for example, inside another lumen 369 in nozzle 371 flush with the distal plane of the apparatus. These fibers act to emulsify occlusive material before such is drawn in through distal port 379 and ejected through side slot 397.

Although side slot 397, as shown, consists of two skives, one in each of the inner and outer wall of the catheter about 1 cm back from the distal plane of the apparatus, the side slot may also comprise a series of smaller holes in either or both of the inner and outer walls. Replacing a skive in the inner wall, for example, with three smaller holes increases the strength of the apparatus and may prevent collapse of that portion of the device as it is pushed through a body lumen towards the site of an occlusion. In addition, a fiber (not shown) can be positioned in the vicinity of the skives or smaller exit port holes, so that acoustic phenomena generated by that fiber can help to force material out of the exit port(s) and to prevent clogging in the exit port region.

An alternate set of "chewing" fibers is also shown in FIGS. 16A and 16B. These fibers 377 could be used instead of, or in addition to, fibers 394. The last 1 mm or so of the distal tips of fibers 377 are free. It is believed that free tips contribute to better emulsification, such that fibers 377 may be able to emulsify occlusive material more effectively than fibers 394. Fibers 377 could be positioned by feeding the fiber from in between the inner and outer catheter walls into a lumen 369 of nozzle 371, and then out of a slit in the outer wall of nozzle 371 (at which point it is glued) so that the distal fiber tip is approximately flush with the distal plane of the apparatus.

Marker band 386 is shown in FIGS. 16A and 16B as mounted on the nozzle rather than on the outermost tubular material, another possible location. The inner location as shown provides the advantage of streamlining the distal outer diameter of the apparatus.

It may be desired to have more than one outlet port in the sidewall of the distal tip, especially if the central lumen of the catheter is to be used for aspiration, as described above. Aspiration causes vessel fluid to pass through one or both of the inlet and outlet ports into the catheter, through the central lumen and out of the patient's body, if desired. Having only one outlet port risks possibly having the outlet port suck against the vessel wall, thereby blocking the flow through that port. Blocked flow risks potentially shutting off the pumping action of the pumping fiber, having the tip heat up due to the lack of re-flow through the distal portion of the catheter tip, and possibly having the partial vacuum damage the vessel wall. Having multiple, circumferentially-spaced, outlet ports helps to equilibrate the forces generated by aspiration, and also helps to guarantee that even if one outlet port is blocked by the vessel wall, other outlet port(s) are available to eject material and/or to facilitate aspiration, thereby preventing the vessel wall from being damaged through the partial vacuum. If more than one skive-type outlet port is cut into the catheter tip, however, the column strength of that portion of the catheter may be compromised, such that the catheter cannot be as effectively navigated through tortuous vessel pathways. Column strength in a multiple outlet-port embodiment may be improved by having the multiple outlet ports comprise a series of small holes, as shown, for example, in FIG. 18C. Hole diameters are chosen to be as large as possible (to facilitate flow) without allowing a guidewire tip to pass through during manipulation during a procedure, and while maintaining the desired column strength of the distal portion of the catheter. Holes of 0.011 inch diameter, spaced about 1 mm apart, have produced satisfactory results. Holes can be punctured through the inner and outer walls using a coring tool made from a sharpened hypo-tube.

It is easier to create the outlet port holes—or skives, if desired—and to ensure that they align, by first melting the inner and outer walls together while positioned around a rod of desired diameter and wrapped with a discernable tube of shrink-wrap. The bonded walls are then punctured/cut with the rod still in place to form the outlet ports. Two or more sets of outlet holes may be cut, with three sets currently preferred. If three sets of outlet holes are used, they may be positioned opposite from (542) and roughly 90 degrees on either side (540) of the bundle of optical fibers 544, as shown in FIG. 18C. This bundle of fibers (comprising the pumping and chewing fibers), as shown, runs down one side of the length of the catheter to the distal section, at which point the bundle divides into the individual fiber tips that form the desired distal-most array shown, for example, in FIG. 18B. Although the sets of holes shown in FIG. 18C each are similarly and evenly positioned with respect to one another, the holes—either individually or in sets—can be longitudinally and/or radially staggered from one another, which can further improve the integrity of the sheath.

When the inner and outer walls are melted together, it is desirable that the melted portion have roughly the same outer diameter as the unmelted portions, to present a uniformly smooth outer surface to the vessel wall. Some wall materials, however, such as soft PVC and LDPE/EVA blend, if not reinforced in some way, may melt to provide a slight depression in which the outlet port(s) would have to be cut. To prevent this partial surface collapse, a length of reinforcing material, such as a soft PEBAX, capable of bonding to the inner and outer tubings when melted and long enough, for example, to span the entire outlet port, may be inserted between the inner and outer walls. This reinforcing material helps the melted inner and outer materials to retain their original dimensions, facilitates bonding between the two tubings, and also strengthens/prevents from tearing the multiple outlet holes.

Flexibility of the various distal tip constructions of the present invention can be improved in a number of different ways. First, the amount of glue used in constructing the apparatus should be limited. The more glue that is used, the stiffer is the final construction.

Second, softer, more flexible materials may be used for the distal portions of the inner and outer tubular portions of the catheter construction. For example, soft PVC has been successfully used for both inner and outer distal walls. Wall materials, such as PVC, desirably are soft enough to render the distal portion sufficiently flexible to navigate the desired tortuous path, but also stiff enough to permit successful navigation without buckling. If PVC is used, colorless PVC is preferred, so that positioning of the fibers can be visualized through the walls, although colored/opaque PVC could also be used. Positioning the outer PVC tubing over the inner PVC tubing is accomplished by using isopropyl alcohol as a lubricant, which later evaporates during the melting process.

Third, distal tip flexibility can be increased by moving the outlet port(s) further proximal from the distal-most portion of the apparatus. The melting of the inner and outer tubular portions 384 and 390, done as part of the creation of the outlet ports, can tend to melt the optical fibers into the tubular walls, creating a stiffer section of the catheter in which the ports are cut. While being slightly less flexible, this stiffer section aids in preventing immediate kinking at the site of a skived outlet port. Moving this melted portion further away from the distal-most portion of the apparatus permits a longer and more flexible section distal of the outlet port. Having the distal-most portion of the outlet port, or series of outlet holes positioned 3 cm or more from the distal-most end of the apparatus has improved flexibility over distal tips having the outlet port positioned about 1 cm from the distal-most portion.

Positioning the outlet ports further back from the distal-most portion, about 3 or more cm away, has been discovered to have the added advantage of creating more of a cooling effect at the distal tip of the apparatus than was previously observed. It is believed that this added cooling effect is due to there being more fluid circulating between the inlet and outlet ports—due to their being positioned further apart—which helps to absorb more of:the heat generated by the pumping and chewing fibers as they create the desirable photoacoustic phenomena to produce flow and/or disrupt occlusive material. These more proximal outlet ports, if skived, preferably have a minimum major dimension of about 4 mm.

FIG. 18A illustrates an alternative method of mounting the pumping fiber 514, as does FIG. 17. In FIG. 18A, tube 520 may comprise, for example, polyimide tubing with a nominal major length of about 1 mm, with portion 522 removed leaving a minor length of about 0.5 mm. Fiber 514 passes from the substantially annular space between inner tubular wall 390 and outer tubular wall 384, through a hole or slit 532 in the inner wall 390 of the catheter distal tip, and into the inner lumen. The distal tip of pumping fiber 514 is then secured to tube 520 with glue, such that its tip extends about 250 microns past the lowest point of tube 520 and is located about 250 microns from the distal plane of the catheter, for the catheter dimensions described herein, such that delivery of short duration, high frequency, low energy pulses of radiation create the pumping and acoustic phenomena described herein. Tube 520 is glued to the inside of the inner walls 390 of the distal tip of a catheter. Fibers 516 (five shown, as another example) are positioned between inner catheter wall 390 and outer wall 384. The apparatus tip can also be convex, as shown, to aid in navigating body vessels and to eliminate any potentially sharp edges.

In connection with the desire to avoid unnecessary heating at the distal tip of the catheter, described briefly herein and in the patent applications incorporated by reference, any of the preceding embodiments may include a thermocouple or other suitable temperature-sensing device, if desired, to monitor the temperature of the site of the occlusion during operation of the invention. Said thermocouple should be positioned to provide accurate temperature information about the distal tip of the apparatus. Positioning the thermocouple, for example, in the substantially annular space between the inner and outer catheter walls is satisfactory. The thermocouple tip preferably is longitudinally located between the distal tips of the pumping and chewing fibers, although it may also be, for example, substantially flush with the distal-most portion of the apparatus, and is preferably encapsulated (e.g., in glue), to isolate the thermocouple from ambient fluids for biocompatibility reasons. Avoiding flush placement of the thermocouple avoids the potential for damaging the thermocouple tip during final polishing of the distal tip of the apparatus. Shown in FIG. 18B is the preferred thermocouple tip 538 radial position, roughly midway between adjacent chewing fibers 516 on the inner tubular wall (close to the center of the device) and offset from the pumping fiber 514 by about 90 degrees. This positioning produces satisfactorily representative temperature readings for the apparatus without being skewed by the energy output of any one particular fiber. Other locations for the thermocouple tip are also possible. The temperature information produced by the thermocouple could be used to trigger an audio or a visual alarm or to control the laser to avoid further heating of the operation site once the temperature of the distal tip exceeds, for example, 50 degrees Centigrade.

FIG. 17 shows another embodiment of the present invention. This particular embodiment further illustrates that the current invention can be used to mechanically disrupt occlusive material wholly apart from any emulsification action. Fiber 514 creates the pumping action through distal port 526. Instead of being flush with the distal catheter plane, as in previous embodiments, outer catheter wall 528 extends beyond inner catheter wall 524 by about 100 to 250 microns, for example, and is sliced as shown to form flaps 518. Flaps 518 will be long enough so that the bubbles formed by the chewing fibers will be approximately centered on the flaps, to generate sufficiently levered force. For the dimensions of the present example, flaps 518 might be 500 microns or more in length, roughly centered on the distal tips of fibers 516, so that the distal edge of a flap extends about 250 microns past distal plane 530, with one or two flaps per fiber for a 200- to 400-micron-diameter catheter tip. When fibers 516 (nine shown for illustrative purposes) are fired in conjunction with the pumping action of fiber 514, flaps 518 vibrate. Holding this distal tip of the catheter gently against a mass of occlusive material can cause the vibrating flaps slowly to abrade and disrupt the surface of the occlusive material. The user should be careful not to overwhelm this capability by forcing the distal tip into the occlusion, which causes damping and thus renders less effective the vibrating flaps. Typical materials of construction and dimensions for this embodiment are as described herein.

FIG. 17 shows mounting the pumping fiber 514 in a manner similar to that shown in FIG. 18A. Although fiber 514 is shown passing down the inner lumen of the catheter shown in FIG. 17, fiber 514 can be positioned as shown in FIG. 15D and 18A, such that only the minor distal portion is positioned in the inner lumen secured to tube 520, with the remaining portion of the fiber located between the inner and outer walls of the catheter. This could be accomplished, for example, by creating a small slit in the inner wall 524, as described for FIG. 18A. If such a construction were used in the embodiment shown in FIGS. 15D and 15E, the distal tip of fiber 514 would still be positioned about 250 microns from the distal plane of the catheter, for the catheter dimensions described herein. In the embodiment shown in FIG. 17, the distal tip of fiber 514 is positioned about 250 microns from the distal plane 530.

FIG. 23 depicts another embodiment of the present invention, which is a variation on the "windowed" device depicted in FIG. 4. The distal end of the device shown in FIG. 23 comprises a number of side windows 682. Three windows are shown, although two or four (as shown in FIG. 24) or more, up to 12, may also be used. Windows 682 are preferably roughly evenly distributed around the surface of marker band 690, although other distributions are possible. In FIG. 23, for example, the three windows are offset by 120 degrees or so from one another, although 90-degree offsets have also been used with satisfactory results. Each window has a dedicated optical fiber 684 mounted therein, to create flow entering through distal port 686 and exhausting through the windows 682. Inner shaft 688 terminates about midway up each window, with each optical fiber, secured to the inner shaft 688 in the usual manner, positioned such that its tip is roughly midway between the terminus of the inner shaft and the distal-most portion of the window. For a 3-French device, typical dimensions for the windows in a 3-window device with a 1-mm-deep marker band are a width of about 200 microns and a length of about 500 microns, with the fiber tip mounted about 125 microns from the distal-most side of the window, and about 250 microns from the distal most edge of the marker band (and thus of the device).

As shown in FIG. 23, windows 682 preferably have angular (e.g., square) corners and ends. It is believed that windows with angular corners may better disrupt occlusive material, as material is pulled in through port 686 and expelled through the windows, as compared to windows having circular ends or rounded corners. Square corners can be created by cutting the marker band with a razor blade while the marker band is mounted on a mandrel. Rounded-end windows can be created by drilling two holes into the marker band material and then cutting out the intervening material with a razor blade. Alternatively, the features may be fabricated using standard laser machining or micro-machining techniques.

Returning to FIG. 23, marker band 690 preferably has a beveled distal-most section 692, to minimize or prevent inadvertent damage to the interior surfaces of the vessel walls through which the device must pass to reach and/or treat the occlusive material. Additionally, the bevel can constrain the path of a guide wire so as to prevent direct exposure with laser light from optical Beveled section may be created by rolling the marker band on a hard surface while the band is mounted on a mandrel so that the proximal portion of the marker band is protected from beveling. Alternatively, a simple beveling or chamfer tool may be used to reproducibly apply the desired bevel to a marker band. For a 1-mm deep marker band, typical bevel dimensions are about 0.0025 inch deep and about 40 degrees from vertical (angle $\alpha$) (measured using a protractor during beveling). A thicker marker band material may be used, for example, 0.003-inch wall thickness, so that a similar beveled surface may be constructed by chamfering the edges of the marker band.

Various methods of attaching the marker band to the body of the device can be used, including simple abutment, abutment with one or more holes (preferably, four holes of 0.005-inch diameter) in the proximal portion of the marker band for glue to seep through to better secure the marker band (shown as 694 in FIGS. 23 and 24), and/or use of a platinum ribbon or wire (e.g., 0.001 inch×0.003 inch×1–2 inches) looped back through one of the holes 694 located in the proximal portion of the marker band and glued to itself, with.the proximal ribbon end glued between the inner and outer walls of the distal portion of the body of the device, preferably approximately at the junction of walls 382 and 384 of FIG. 15 or at the HDPE/LDPE outer wall junction of the alternate embodiment described. Addition of the platinum ribbon also appears to improve the "pushability" of the distal end of the device, which is desirable during treatment.

It has been discovered that the pushability—and thus, in part, the efficacy—of the embodiments disclosed herein, including the device shown in FIG. 23, are improved by taking advantage of an "over-the-wire" design. In other words, a construction is preferable that is capable of (i) tracking a guide wire through various body lumens to the site of the occlusive material to be treated and (ii) tracking back and forth, as necessary, over the wire during treatment, rather than simply relying on its own inherent stiffness to move across or through the occlusive material. The device depicted in FIG. 23, for example, preferably is used substantially as described for the device shown in FIGS. 2 and 5. More specifically, after a guidewire has been delivered to, and then across, the occlusion to be treated, the device (with lumen 680 mounted on the guidewire) is advanced along the guidewire through the occlusion, so that the active tip of the device is distal of the occlusion. The beveled section 692 aids the device to cross the occlusion by minimizing the surface presented to the clot as the device passes over the wire. To further aid the device to cross the clot, the shaft of the device may be strengthened by adding a mandrel extending distally to the active tip of the device. The device may be activated with the guide wire extended beyond the distal tip, or with the wire withdrawn. Withdrawing the wire may enhance the efficiency of clot removal. After the fibers are activated with high-frequency, low-energy pulses of radiation, as previously described, the device is slowly withdrawn through the occlusion, disrupting occlusive material in the process.

Although not yet fully understood, it appears that the embodiment shown in FIG. 23 is better able to disrupt occlusive material if flow is allowed to develop over longer periods of time than for the embodiments having both pumping and chewing optical fibers. For example, maintaining a preferred duty cycle of 0.33, a first fiber in FIG. 23 preferably would fire consecutive pulses of radiation for about 100 pulses, and then "rest" for about 200 pulses, with the previously described frequency, energy per pulse, and wavelength, before the next fiber would fire. This compares to the embodiment shown in FIG. 18, for example, which might have its pumping fiber 514 fire, e.g., for about 20 consecutive pulses, with about 40 "rest" pulses, before firing would be shifted to each of the chewing fibers 516, the first of which might only fire for a few consecutive cycles of one or two active pulses and two or four "rest" pulses, before firing would be shifted to the next chewing fiber. By firing each fiber for an increased number of consecutive pulses, flow is able to develop, where flow might otherwise not develop with this embodiment.

FIG. 24 discloses a variation on the marker band shown in FIG. 23. In this embodiment, beveled section 696 includes bevel ports 698 and auxiliary ports 700. Each fiber and slot combination, as described for the marker band in FIG. 23, has a corresponding bevel port 698. Each bevel port may have any shape, from round to oval to elongated oval. The larger the port, the easier it is to align with the fiber 684. In any event, the combination of bevel port 698 and window 682 define a working edge 702 that causes disruption of the occlusive material during treatment as occlusive material is drawn into the apparatus through window 682 and/or bevel port 698. Since bevel 696 restricts flow somewhat when compared to flow generated through a marker band design lacking any bevel, optional auxiliary ports 700 help to provide additional flow through the distal tip of the device to provide better cooling of the beveled device.

FIG. 25 discloses another variation on the "over-the-wire", "dual lumen" design. Lumen 704, made from a resilient flexible material such as LDPE, e.g., is designed to travel over a guidewire, and so to deliver the device to the treatment site and permit movement of the device during treatment. Lumen 706, having pumping fiber 708 mounted therein as previously described, serves to generate flow through the distal tip and out of exhaust port 710. An additional optical fiber (not shown) may be mounted in the vicinity of exhaust port 710 to further disrupt occlusion particles as they are ejected from the device. Fiber 708 is introduced into lumen 706 through a small slit 714, and is glued so that its tip is positioned the appropriate distance from the distal-most portion of lumen 706 so as to generate flow through the device, all as previously described. Fibers 712 serve as chewing fibers to disrupt the occlusive material as the material is drawn towards the device through the flow action of fiber 708. Outer tube 713 may be PVC, e.g., flared using heat and a flaring tool to the desired diameter to accept the addition of lumen 706. FIGS. 25B and 25C depict two arrangements of five fibers 712 distributed around the device. Other arrangements or other quantities of fibers are possible. Materials of construction of these embodiments are not materially different from the embodiments earlier described in this application. The profile of the distal tip may be made more streamlined by downsizing the lumens and/or molding the pump tube 706 from adhesive, without an additional tubular material as shown in FIG. 25, by molding and setting the adhesive around a removable Teflon bead with the fiber 708 already in position inside the bead.

One advantage of these "dual lumen" designs is that the guide wire does not impinge the active area of the device, so that the clot disruption efficiency is not substantially affected by the position of the wire. Furthermore, since the "dual lumen" devices are asymmetrical, treatment coverage of the occlusive material can be achieved by rotating the device around the guide wire.

FIG. 25D shows a variation on the "dual lumen" embodiment shown in FIG. 25A. Instead of having a single pumping fiber positioned within lumen 706, an entire apparatus, such as the one shown in FIG. 18 and described previously, is positioned therein to provide the active treatment mechanism to disrupt occlusive material. Instead of having one or more proximal skives as exhaust ports, however, the device would use port 710 to exhaust material from the device. To create a simple version of this device, about 0.5 cm of the distal outer PVC tube 384 of the device shown in FIG. 18, just proximal of the marker band, is removed. The inner PVC tube 390 is cut just proximal of the pump tube 520, and is then threaded between the optical fibers. A short polyimide tube of about 0.016 inch inner diameter, with a 0.001-inch-thick wall is glued into the distal end of the cut inner tube and then glued/attached to the outer portion of the marker band. The distal edge of a small (e.g., 3–5 mm in length) auxiliary exhaust tube with diameters equal to the pump tube is then attached/glued to the proximal edge of the pump tube. The proximal edge of the exhaust tube extends between the fibers to provide a viable exhaust port free of the threat of clogging due to material catching between the fibers. If desired, the entire active distal end can be wrapped in shrink-wrap 726 or a flared PVC tube to form a unitary structure.

FIG. 26 discloses a "Gatling gun" type of embodiment, which includes a series of short outer tubes 718, typically of polyimide, attached (typically glued with cyanoacrylate) to the outer surface of a second inner tube 720. A first inner tube 722 is concentrically arranged within second inner tube 720, to provide concentric walls through which the optical fibers (and mandrel and thermocouple, if desired) are positioned. Each outer tube 718 has a small slit about midway on its length, through which its dedicated optical fiber 716 is inserted from between the walls of the inner tubes. Lumen 724 will accept a guidewire, and permits the device to travel over a guidewire to the treatment site, and over the guidewire during actual treatment, as previously described.

FIG. 27 shows a device 900 for disrupting occlusive material in a body lumen, as previously described, according to the most preferred embodiment of the present invention. Many aspects of this device are described in relation to other embodiments in this description of preferred embodiments, particularly in relation FIGS. 15 and 23, which aspects supplement the present description of this particularly preferred device 900 in relation to FIG. 27.

For illustration purposes, the device 900 is shown (FIG. 27A) with its most proximal end housed in, and in operable communication with, a conventional introducing device 1000. The device 900 is an annular structure which extends along a longitudinal axis A. Along the length of the device 900 are various sections 902, 904, 906, 908 and 910, composed of different materials, as described below. In each of these sections, the annular structure of the device 900 is composed of concentric annular layers, composed of different materials, as further described below. The varied composition of the device 900, both longitudinally and in annular cross-section, give the device its desirable properties of strength and flexibility, where needed, for its intended purpose.

As shown in FIG. 27A, the device 900 has a most proximal section 902, the outermost annular layer of which is preferably composed of a composite of polyimide/spiral stainless-steel tubing, such as the Phelps-Dodge High-Performance Conductor tubing previously described in relation to FIG. 15A. This most proximal section 902 (shown abbreviated, for convenience) is approximately 95 cm in length and about 0.040 inch in OD. Adjacent this proximal section 902 is a middle section 904, the outermost annular layer of which is preferably composed of high-density polyethylene (HDPE). This middle section is about 47 cm long and has an OD of about 0.037 inch. Adjacent this middle section is a first distal section 906, the outermost annular layer of which is preferably composed of low-density polyethylene (LDPE). Adjacent this first distal section is second distal section 908, the outermost annular layer of which is preferably composed of plasticized polyvinylchloride (PVC) of 60–65 Shore A hardness. The first distal section 906 and the second distal section 908 have lengths of 5 cm and 3 cm, respectively, with both of these sections having an OD of about 0.035 inch, although ODs of from about 0.035 inch to about 0.040 inch have been used. Appended to the second distal section 908 is the distal-most section 910, which has a length of about 0.039 inch, an ID of about 0.034 inch, and an OD of about 0.038 inch. The various sections are joined at the junctions between 902 and 904, 906 and 908, and 908 and 910 with glue, and at the junction between 904 and 906 by melting, in ways previously described.

Preferably, a thermocouple wire 914 in the interior of the annular structure of the device 900 extends along most of the length of the device, terminating within the distal-most section 910 before the distal end 912 of the device. Preferably, this wire 914 extends along a side of the device, as shown, substantially parallel to, and offset, from the central longitudinal axis A. Preferably, this wire 914 is positioned between the outermost annular layers of the device described above and the innermost annular layers described below. This thermocouple wire 914 is also shown in FIG. 27C.

A platinum ribbon or wire 916 also lies within the interior of the device 900. The proximal end of the platinum ribbon is located at the junction between the middle section 904 and the first distal section 906. The platinum ribbon 916 continues along the length of the device into the distal-most section 910 until it reaches a hole 918 in the distal-most section. One or more of the holes 918 can be seen more clearly in FIGS. 27B and 27C. At this point, the platinum ribbon 916 is threaded through the hole 918 and glued to itself at a point proximal in relation to the hole, as previously described in relation to FIG. 23. Preferably, the platinum ribbon 916 extends along a side of the device, as shown in FIG. 27A, substantially parallel to, and offset, from the central longitudinal axis A, and opposite the thermocouple wire 914 described above. This ribbon 916 is preferably positioned between the outermost annular layers, described above, and the innermost annular layers of the device.

The innermost annular layers of the device 900 are now described. In the most proximal section 902 of the device, the innermost annular layer 903 is preferably composed of polypropylene and has an ID/OD of about 0.023/0.026 inch. This innermost annular layer 903 continues along the length of the device into the middle section 904, terminating at dotted line 905. At this juncture, the polypropylene layer is joined (using joining methods, such as gluing, as previously described) to an innermost annular layer 907 which is preferably composed of PVC and has an ID/OD of about 0.022/0.026 inch. This innermost annular layer of PVC continues along the length of the device, through the remainder of the middle section 904, through the first distal section 906, through the second distal section 908, and into the distal-most section 910, terminating therein at dotted line 911, as can be seen through the window 920, which is further described below. Within the innermost annular layer 907 lies a tube of polyimide 909 (shown in FIG. 27C) of about 0.039 inch in length, the distal end of which terminates at dotted line 911 (FIG. 27B) along with layer 907.

The device 900 is a variation of the "windowed" device shown in FIG. 23. The distal-most section 910 of the device 900 is a marker band having four windows 920, evenly spaced about 90 degrees apart, as shown in FIGS. 27B and 27C. The windows are preferably about 0.008 inch wide and 0.02 inch long, although shorter windows of about 0.005 inch have produced satisfactory results. One fiber 922 is positioned at each window 920. Within the device 900, each fiber 922 extends along the length of the device from its most proximal end to a point marked by dotted line 924, that is, at about three-quarters of the length of the window 920. Each fiber is positioned between the outermost annular layers and innermost annular layers described above, although the innermost annular layer in the distal-most section 910 of the device terminates at a point marked by dotted line 911, that is, at about one-half of the length of the window.

Preferably, the marker band 910 is about 0.038 inch in OD diameter and about 0.039 inch in length, although dimensions of from about 0.028 inch to about 0.042 inch in OD and from about 0.020 inch to about 0.060 inch in length have proved satisfactory. Within the marker band 910, the innermost annular layer has an ID of about 0.018 inch, although IDs of from about 0.018 inch to about 0.022 inch have proved effective. At a point 1 mm back from the distal end of the innermost annular layer, the ID of this layer increases to about 0.022, although IDs from about 0.018 inch to about 0.022 have proved effective. The innermost annular layer maintains this ID from this point to a proximal point at dotted line 905, where the ID increases to about 0.023 inch. The innermost annular layer maintains this inch ID from this proximal point to the proximal end of the device 900.

Preferably, the marker band section 910 is beveled at its distal end, as shown in FIGS. 27A–C, to facilitate movement through a vessel. The bevel 926 may begin at about 0.003 inch (dimension x) from the distal end 912 of the marker band section and have a bevel angle a (measured from the side of the device) of about 51.3 degrees. Further, the opening at the distal end 912 of the marker band lying between the innermost portions of the bevel may have a ID of about 0.028 inch (dimension y). The marker band section 910 may have holes (not shown) on the beveled portion thereof, such as the holes 698 of FIG. 24. In such a case, the holes would be smaller than the holes 698, for example, having diameters similar to that of the fibers 922. The holes could be formed manually, using a drill bit for example, although machining the holes is preferable to provide better uniformity and reproducibility.

The bevel 926 on the marker band section 910 facilitates movement of the device through the vessel while reducing or preventing damage to the vessel. The bevel 926 may provide a further advantage. That is, as previously described in relation to FIG. 23, the device 900 may be delivered "over the wire". A wire or guidewire (typically, 0.014 inch in OD) provides greater maneuverability and safety, as one can push the device forward or pull it backward within a curved and branching vessel without undue concern about causing damage to the vessel wall. After delivery of the device 900 over the wire, a distal end of this wire or guidewire may be positioned beyond the distal end 912 of the device or fully housed within the device, when one or more of the optical fibers 922 are energized. Preferably, the distal end of the guidewire is positioned within the device, as described further below. However, when the guidewire 928 extends beyond the distal end 912 of the device, as schematically illustrated in FIG. 27E, it is relatively free to move about beyond the distal end 912. If completely unconstrained, the distal end of the guidewire 928 might move in front of the optical fiber and thereby be irradiated by the radiation 930 emitted from an optical fiber 922. Such a result is undesirable, as a heated guidewire may damage the vessel. The bevel 926 prevents this undesirable result by preventing the extended distal end of the guidewire 928 from moving in front of an optical fiber 922 where it might otherwise be irradiated. Positioning of the guidewire 928 and the device 900 is further described below in relation to the operation of the device.

The most preferred embodiment of the device is now described in relation to FIG. 27D, which shows section 906 of the device 900. In this embodiment, holes 928 extending through both the outermost and innermost annular layers are placed in the first distal section 906 of the device. Preferably, six such holes 928 are used, although anywhere from one to about 15 holes may be used. The holes 928 may be arranged in three sets along the length of the first distal section 906, each set having two holes positioned along an annular portion of section 906. For each set, the two holes may be spaced 180 degrees apart and offset 90 degrees from the location of the thermocouple wire 914 and the platinum ribbon 916. In FIG. 27D, only one hole of each set can be seen, the other hole being located on the other (non-visible) side of the device. While an arrangement of six holes has been described, other arrangements are possible, particularly if a different number of holes is used. For example, if 15 holes are used, they may be arranged in five sets along the length of the first distal section 906, each set having three holes, evenly spaced 120° apart along an annular portion of section 906.

Preferably, the holes are 0.011 inch in diameter, although diameters of about 0.005 inch to about 0.012 inch are possible, as are oval dimensions of from about 0.003 inch by about 0.005 inch, to about 0.003 by about 0.011 inch, or to about 0.011 inch by about 0.39 inch. The most proximal set of holes is placed about 5 cm proximal from the distal end 912 of the device, while the middle set of holes and the distal-most set of holes are placed about 4 cm and 3 cm, respectively, from the distal end 912 of the device.

It is believed that the holes used in this most preferred embodiment provide advantageous fluid flow when the device is employed as described in relation to FIG. 23. That is, a device such as device 900 is pushed through an occlusion 362 (FIG. 5) preferably with the aid of a guidewire 928, a bevel 926 on the distal end 912 of the device, and a conventional lubricious or hydrophilic coating on the outside of the device 900. Once the device is desirably placed with the active tip of the device distal of the occlusion, the optical fibers 922 are activated and the tip of the device is pulled back through the occlusion. This causes occlusive material to be sucked into the distal end 912 of the device and expelled through the windows 920. However, when the tip of the device is pulled through the occlusion, there may be loss of fluid or blood at the tip which inhibits the functioning of the device. It is believed that the blood flowing into the holes 928 at a relatively high pressure section of the device and exiting the relatively low pressure tip of the device remedies this problem.

When the device 900 of FIG. 27D is used with the guidewire located proximally of the distal end 912 (not shown) and the holes 928, the blood flow may be on the order of about 6 $cm^3$ in 60 seconds. When that same device is used with the guidewire extending beyond the holes 928, such as beyond the distal end 912 as shown in FIG. 27E, the blood flow through the 6 holes, arranged and sized as shown and described above, may be on the order of about 1 $cm^3$ in 60 seconds. Such flows provide sufficient fluid to the distal tip 912 of the device to maintain proper functioning of the device 900.

As described previously, the device 900 produces pressure waves which assist in the breaking up of clot material. The device also and primarily acts as a fluid dynamic device, utilizing the asymmetry of the structure to produce net fluid flow and clot-destructive forces, as described further below. The device produces macroscopic fluid motion which serves to move the clot material or occlusive material around to maximize the amount of material passing in the vicinity of the functional area of marker band section 910 of the device.

Preferably, the device 900 has four windows 920 and four optical fibers 922, as shown and described above. A device with fewer windows/fibers could be produced more easily, although with such a device there is a concern if one or more of the windows became somehow blocked, or positioned against the vessel wall, there would be an insufficient number of active windows for efficient functioning of the device. It is believed that with a device 900 having four windows/fibers, two of the windows should almost always be unobstructed to provide for proper functioning of the device. A device 900 having greater than four windows/fibers could also be used.

The preferred method of operating the device 900 is now described. The proximal ends of the optical fibers 922 are operably connected to an energy source (not shown), which is preferably a laser which produces radiation that is well absorbed in blood and poorly absorbed in the wall tissue of the vessel. A preferred wavelength is about 414 nm, although such wavelengths may be hard to produce and lasers producing such wavelengths may be difficult to obtain on a commercially practical basis. A suitable wavelength is about 532 nm, as this wavelength is well absorbed in blood, having an absorption coefficient ($\alpha$) of about 240 $cm^{-1}$ for this wavelength, while being poorly absorbed in the wall tissue of the vessel. One laser producing the desired wavelength is a doubled Nd:YAG laser.

Preferably, the laser is pulsed at about 5 kHz, using a pulse width of about 25 nanoseconds. The energy supplied by the laser may be up to about 500 $\mu J$. Typically, laser energy of about 200 $\mu J$ is delivered from a 50 $\mu m$ fiber, an amount sufficient to produce vapor bubbles in the vessel fluid. In order to manage the power (up to about 1W) of the laser, which would be too high for a 1–3 mm vessel, the laser is cycled through "on" and "off" phases. A duty cycle of about 30%, which produces an average laser power of about 300 mW, can be used to reduce the total power delivered to the vessel. For example, for a particular fiber 922, the laser power may be cycled through an "on" phase of 100 pulses and an "off" phase of 200 pulses (providing a duty cycle of about 33%), with the pulses being separated in time by 200 $\mu$seconds. The above-described parameters produce good results, although other parameters (such as fiber diameter and pulse repetition pattern) may be used to produce desired or optimal fluid mechanics and clot emulsification efficiency. Operational parameters may be chosen upon consideration of fluid viscosity and heat build-up within the fluid. For example, when the fluid is relatively viscous (for example, about 4 cP), a greater number of pulses in the "on" phase may be desired to get the fluid moving. However, any temptation to increase the number of "on" pulses, should be checked by a consideration of how much heat build-up in fluid is acceptable to avoid damage to the vessel wall. Preferably, a thermocouple 914 is used to measure the temperature of the fluid, and preferably, to control the applied laser power in a feedback control loop. Preferably, any such feedback control loop operates automatically, such as via a microprocessor or computer or other conventional means (not Shown).

When the device 900 is operated as just described, the desired motion of the fluid therethrough is obtained. This fluid motion is schematically illustrated in FIG. 28 over a period of from zero to 100 μseconds. For example, FIG. 28A shows the initial activation of the device 900, wherein energy is deposited at the tip of an optical fiber 922 located adjacent window 920. As the "on" cycle continues, this deposition of energy causes a vapor bubble 940 to form and expand, as shown in FIGS. 28B and 28C, until the bubble collapses at about 60 μseconds, as shown in FIG. 28D. As shown particularly in FIGS. 28B–D, the bubble is expanding and collapsing in an asymmetric environment, that is, in an environment confined by asymmetric structure of the marker band section 910.

The asymmetric structure of the marker band results from one or more of its structural components, such as the distal opening 912, the bevel 926 (if bevel option employed) or other corner structure, the marker band wall, and the window 920. Other asymmetric structures and structural components are possible, the choice often depending on a variety of functional, practical and/or safety concerns. For example, an asymmetric marker band structure which employs a corner structure other than the bevel 926 provides a good asymmetric environment for bubble expansion and collapse and resulting fluid movement, but is not considered the safest option.

The expansion and collapse of the bubble in proximity to the asymmetric marker band structure 910 of the device causes a net fluid displacement in the vicinity of the fiber tip, which in turn causes net fluid displacement 942 directed outwardly from the window 920, as shown in FIG. 28E. A rebound phenomenon 944 may also occur at the fiber tip, as shown in FIG. 28F. In this manner, fluid in the vessel is moved mainly from the vicinity of the distal opening 912 of the device, through that opening and outwardly from the window 920 for a desirable directional displacement of fluid from the device 900. As described above, a single fiber 922 may be energized for 100 "on" pulses, followed by a rest for 200 "off" pulses, before another fiber 922 is cycled in this manner.

When the device 900 has been operated for many pulses, vigorous fluid motion, as schematically shown in FIG. 29 over a period of from zero to 60 μseconds, is obtained. For example, after many of 100 "on" pulses have been delivered to an optical fiber 922, a train 946 of net fluid displacements 942 is produced, as shown in FIG. 29A. Once the 100 "on" pulses have been delivered, and the fiber is in its rest phase for 200 "off" pulses, the train 946 of fluid moves further outwardly from the window 920, as shown in FIG. 29B. On a macroscopic level, the net fluid displacement is observed as a jet 948 of fluid being expelled from the window of the device 900, as shown in FIG. 29C. Once one duty cycle has run its course, resulting in the jet of fluid just described, the cycle is reproduced at another fiber 922. The firing pattern or schedule (i.e., firing of adjacent fibers, opposite fibers, or any combination of fibers, sequentially) may be selected according to the application (for example, according to the nature or position of the occlusion, or according to the heat build-up occurring in a particular region in the vessel, etc.). The repeated asymmetric jetting of fluid proximal to the distal tip 912 of the device and outward at various windows 920, according to a selected firing pattern, causes considerable material agitation in the vicinity of the tip and significant motion of the tip. Thus, the firing of the optical fibers 922 arranged in the device 900 provides a very effective fluid emulsification process.

When using the device 900, it is preferable to extend a guidewire 928 through the occlusion at the outset and then push the device 900 along the guidewire until the distal end 912 is distal of the occlusion. The guidewire may be of a particularly desired shape, or may be shapable, to influence the position of the device and/or the motion of the device traveling over the guidewire. Preferably, the guidewire is then withdrawn into the device 900, proximal to any flow holes 928 (FIG. 27D) that may be employed, so as not to interfere with the flow of fluid therethrough. The device 900 is then activated by supplying energy to one or more of the optical fibers 922, as described above, during which the distal end 912 of the device is pulled back (proximally) into the occlusion. After the device has been pulled back through the occlusion ("one pass"), the process is repeated, with another extending of the guidewire 928 through the occlusion. This method of operation is the most effective in terms of emulsification and the best in terms of heat management, in view of the internal position of the guidewire during activation.

It will be appreciated that there may be times when the positioning and repositioning process just described is difficult or is not as safe as desired. For example, when a vessel has many branches, after the initial positioning of the guidewire, it may be difficult to reposition the wire as it was initially positioned, given the number of branches present. Further by way of example, when a vessel is tortuous or convoluted, repeatedly extending the guidewire through the occlusion may threaten the safety of that vessel. Thus, it is possible to extend the guidewire through the occlusion initially, to push the device 900 along the guidewire until the distal end 912 is distal of the occlusion, and to leave the guidewire extended distal of the distal end 912 of the device. The device 900 may then be activated and pulled back over the guidewire, while the guidewire remains in place. After one pass of the device, the device may be repositioned by extending it again over the guidewire and the process may be repeated for additional passes. This method of operation is acceptable, although less effective in terms of emulsification and less optimal in terms of heat management than the preferred method described above.

There is yet another method of operation that may be used, although this method is the least preferred, as having relatively lower emulsification efficiency and heat management capability. According to this method, the guidewire is extended distal of the occlusion and the device 900 is activated as it is pushed forward (distally) along the guidewire into the occlusion. Generally speaking, in order to protect the vessel wall when the device is being pushed distally, it should only be pushed along a guidewire, with the guidewire remaining distal of the distal end of the device.

For the treatment of particularly small vessels less than about 2 mm in inner diameter, devices approaching 1 French dimensions (or smaller) have been constructed. Such devices can be thought of as "active wires": "wires" in the sense that the device is small enough to be deliverable through a guide catheter rather than over a guide wire (the typical manner of delivery of larger catheter devices) and/or is roughly no larger in diameter than a typical guide wire;

and "active" in the sense that although these devices are only roughly wire-sized, each is capable of delivering optoacoustic energy to a treatment site. Many different constructions of an "active wire" are possible. Several embodiments within the scope of the present invention are shown in FIGS. 19 and 20.

FIG. 19A shows a device having a diameter (e.g., of about 0.018 inches) sized to enable delivery through a commercially-available guiding catheter—e.g., the Turbo-Tracker 18 (available from Target Therapeutics, Inc.) or the Rapid Transit 3F (available from Cordis Corporation). The device comprises a polyimide sheath 600, coated with a lubricious coating such as Teflon or another hydrophilic or lubricious coating. Such tubing is commercially available from Phelps Dodge of Trenton, Ga. While sheath 600 has a relatively simple construction, it may also have a more complicated structure as previously disclosed for other embodiments. For example, the body of the device may have variable flexibility/stiffness and strength along its length, for pushing the distal end of the device to a blockage in a body lumen, preferably a cerebral vessel, without causing kinks in the device or the optical fibers therein and without damaging the cerebral vessel walls. For example, Teflon heat-shrink tubing could form the distal portion of the sheath in lieu of the distal 5–20 cm or so of the polyimide tubing. Alternatively, a long coil of 20 cm or more could be coated in a urethane-type material, such as Tecoflex (urethane dissolved in dichloromethane, $CH_2Cl_2$), to create a long, flexible tube that could serve as part of the body of the device. In addition, a hydrophilic coating on the outside of the device may be used to facilitate delivery through body lumens and/or though a guide catheter, forexample.

Appropriate designs for the body of the device, as for the body of other devices disclosed herein, may result from the consideration of various factors, including the choice of materials used, the thickness of these materials, the use or omission of an inner lumen, the attachment or non-attachment of the optical fibers to the sheath structure at various points along the length of the device other than at the distal-most portion on the device (at or near the marker band), and similar factors. Layered constructions, as previously disclosed, may also be used to provide more strength and pushability at the proximal portion of the device with more layers, and more flexibility at the distal portion of the device with fewer layers, with the most flexible portion typically being the distal-most portion of the device. Layers may be constructed out of polyimide, polyethylene terephthalate (PET), high- and low-density polyethylenes, braided tubular structures, nitinol or stainless steel tubes, or reinforcing materials such as nitinol or stainless steel, coils, etc. Optional layers of heat-shrink material may also be used for added strength or resiliency on portions or all of such devices may also be used.

The distal end of the sheath 600 is attached with cyanoacrylate glue (such as Loctite 4011) to a radiopaque platinum coil 602 having a variable pitch and variable diameter. Attachment is improved by inserting several windings inside the distal portion of the polyimide sheath before gluing, rather than relying upon direct abutment of the proximal coil windings to the distal edge of the sheath. This coil, which may have a length of up to about 5 cm, with a 1- to 2-cm length proving satisfactory, provides increased flexibility at the distal end of the device so as better to track along tortuous pathways of the brain, for example. Variable spacings 618 between the distal adjacent windings of the spring enable flow generated at the distal tip of the device through port 613 and/or port(s) 614 to exit the device. Spacings 618 may be achieved, for example, by wrapping the primary wire of the coil (e.g., a coil having a diameter of 0.00125 or 0.0015 or 0.00175 inch) around a mandrel of diameter equal to the desired inner diameter of the coil. The wire is initially wrapped with minimal or no pitch, but with the final (distal) 3 to 7 windings having a pitch of between about 0.010 to 0.020 inch. To increase the amount of space within the distal end of the device, and so to decrease the chances of the device clogging with an agglomeration of disrupted material, e.g., the distal portion of the coil may also be flared slightly to increase the overall diameter of the distal portion of the coil, e.g., inner diameters of from about 0.014 inch (proximal) to about 0.016 inch (distal).

A marker band 612, comprising platinum, gold, or alloys of either such as platinum/iridium, is glued to the distal end of the coil. Typically, this marker band has an outside diameter of about 0.018 inch and a length of about 0.018 inch. If further security is desired to better ensure that the marker band will not be lost during a procedure, a mandrel 620, shown in FIG. 19B but not depicted in FIG. 19A, may be run down the length of the device, glued or welded to the coil, and attached—e.g., welded and/or glued—to the marker band. A tapered 310-stainless steel mandrel, tapering evenly from about 0.010 inch diameter to about 0.002 inch over the last 20 cm or so of length has been used effectively for this purpose. The mandrel may be positioned midway between adjacent optical fibers 616 so as to minimize any interference in the turbulence generated at the tip of the device during operation. The mandrel 620 can be physically connected to the marker band 612 in any number of ways. For example, the cylindrical distal portion (or a flattened portion of the distal portion) of the mandrel may be connected to a portion or all of the inner length of the marker band. Further by way of example, a small slot may be cut into the proximal edge of the marker band, such that the outer surface of the mandrel is flush with the outer surface of the marker band. A mandrel contributes to the pushability of the device and also provides slight "torqueability". Such a mandrel can also be used to shape the distal tip of the device. For attaching the stainless steel mandrel to a platinum, tubular marker band, it is believed to be most effective to extend the mandrel through and beyond the distal edge of the marker band by less than or equal to about 0.050 inch. When the mandrel is contacted with the ground electrode, the mandrel "melts back" to form an acceptable bond with the marker band. Other methods of welding were tried, with limited success and/or damage to the marker band.

If a thermocouple 622 is desired to provide information about the temperatures experienced at the distal tip of the device during treatment, one may be positioned in the marker band about midway along the marker band in a manner similar to how the mandrel is positioned. A 2-fiber, 44- or 50-gauge, T-type thermocouple (approximately 0.001 inch×0.003 inch), commercially available from Phelps Dodge, has proven satisfactory. Having a flexible thermocouple is important to maintain the flexibility of the overall device.

Before device assembly, the marker band 612 has the desired number of holes 614 (four shown in the preferred embodiment depicted in FIG. 19A, corresponding to the four fibers 616) drilled into it while positioned over a mandrel to avoid crushing. Each hole 614 in FIG. 19A corresponds to a fiber 616 glued to the inside of the marker band and positioned such that the fiber tip sits approximately in the center its corresponding hole. Such positioning has been found to facilitate the desirable sucking/chewing motion of these devices. Holes of 0.005 inch diameter, centered about 0.005 inch proximal from the distal edge of the marker band have been found to be satisfactory for this purpose. Alternative, illustrative designs for a marker band within the scope of the present invention are depicted in FIGS. 20–22. FIG. 20, for example, depicts a marker band having a rounded distal portion, to more closely resemble a typical guide wire used to navigate various tortuous vasculature. Such a profile is gentler on vessel walls during navigation and treatment, as it eliminates some of the more abrupt edges of a typical marker band. Front opening 640 and openings 642 created by the curved webbing permit flow through the front of the device as usual.

FIGS. 21A and 21B depict a marker band having the same arrangement of four optical fibers, thermocouple and mandrel as shown in FIG. 19B. However, marker band 646 is constructed so that each of the six longitudinal elements would insert into a dedicated cylindrical shaft pre-cut into the wall of the marker band. Shaft 626 is for optical fiber 616 and shaft 628 is for thermocouple 622. Because the various elements are to be inserted into the wall of the marker band, rather than simply attached to the inner wall of a simple cylindrical marker band, as in FIG. 199B, the proximal portion 648 of the marker band is preferably wider than the distal portion 650, to accommodate drilling or casting of the various dedicated shafts. Wider portion 648 preferably terminates proximal of the ports 614, however, to facilitate proper placement of the distal tips of fibers 616 within the center of each port 614, for example. Such marker band could be constructed by conventional micro- or laser-machining.

Returning to FIG. 19A, an active wire with the depicted and described construction can generate the sucking/chewing phenomena previously described herein and in the related grandparent and parent applications. To help the device to stay unclogged, however, during the treatment procedure of disrupting occlusive material in a body vessel, one or more fibers (a single fiber, 604, depicted in FIG. 19A) may be positioned within the coil 602 and in the vicinity of the open windings 618. This fiber 604 preferably will help to further disrupt any larger particles of blood clot that remain after initial disruption by fibers 616, before those particles can escape the device. Fiber 604 can be positioned by placing and gluing a spacer 605 over the fiber 604. Fibers 616 can then be glued to the outside surface of the spacer to maintain separation between the fibers in the distal portion of the device and so to prevent the potential clogging due to the fibers 616 forming a particle trip through proximity to one another.

Spacer 605 can be constructed out of a short tubular polyimide (or other suitable material) sheath 608, e.g., about 2–10 mm in length, placed over a mandrel, and a second polyimide tube 606 of larger diameter attached to the first, with the gap between the two, concentrically positioned tubes filled with glue. While this structure is satisfactory as a spacer, and permits the fluid and material to exhaust through the spaces between adjacent windings, the spacer also may have a shaped distal surface, such as a cone (depicted in FIG. 19A). This shaped distal portion, such as the cone 610, may be formed from a blob of glue, affixed to the end of the assembly while still on the assembly mandrel and shaped with a razor blade once sufficiently set. An angle of around 45 degrees has proven satisfactory, although other angles could be chosen. Such a shaped surface, in addition to potentially improving the flow characteristics within the platinum coil 602 proximal of the marker band, also may permit increased movement/gyration of the distal tip of the apparatus during treatment, which in theory permits better coverage of the occlusion and thus increased recanalization. This potential for increased movement is believed to be due to the force exerted on the sloped surface of the cone 610 as the fluid exhausts through the distal spacings 618 of the coil, which force (and direction) will be affected by the chosen angle of the sloped surface.

The spacer 605 should be placed and glued over fiber 604 proximal of the distal end of the fiber, such that after polishing, fiber 604 extends past the spacer by about 0.002 inch. Further, for this particular construction, the tip of fiber 604 should be about 0.009 inch from the proximal edge of the marker band 612 so as not to adversely affect the pumping/chewing characteristics of the device.

FIG. 22 depicts another structure for positioning a fiber substantially within the center of the device. Webs 654, at the proximal end of the marker band, join at central junction 656 to hold central fiber 604 in position, with the distal tip of the fiber 604 extending the appropriate distance past the junction. As depicted, fibers 616 are glued 652 into place on.the inner surface of the marker band such that the distal tip of each fiber is positioned the appropriate distance from the distal-most portion of the marker band, all as previously described. This marker band can be connected to a coil shown in FIG. 22C, as previously described. Flow generated through port 613 and/or ports 614 and 660 then can pass through the spaces 662 between adjacent webs, and then exhaust from the device through widely spaced coil windings 618. Additional security for this particular marker band could be achieved by hooking and gluing or soldering or welding a mandrel (not shown) onto one of the webs 654.

FIGS. 22A–C also depict both circular or oval ports 614 and quadrilateral ports 660. This combination of port shapes and sizes, in relation to how the fibers are positioned in those ports, can cause a combination of the various front- and side-chewing phenomena disclosed herein, which better disrupts occlusive material.

Another possible construction of an "active wire" (not depicted) includes the body of the device comprising a long, nitinol tube instead of the polyimide tube 600. The distal portion of the tube would be chamfered to fit snugly within a distal portion of a short coil to add more flexibility to the distal-most portion of the device. The nitinol hypo-tube could be skived in the same manner as described for the polymeric materials, to provide appropriate outlet ports for material flowing through the distal tip. The distal portion of the nitinol tube may be annealed using a tube furnace, thereby creating a tube with both proximal austenitic (super-elastic) and distal martensitic (super-malleable) properties. The elasticity/increased flexibility of the distal portion permits the distal end to better navigate tortuous pathways while remaining rigid enough to permit accurate navigation through the pathway.

While FIGS. 19, 20 and 22 depict the use of a coil proximal from the marker band, such coil is not necessary to practice the invention. One option would be to do away entirely with a coil or other distal sheath, and simply have the optical fibers revealed for 1 or 2 centimeters between the main body sheath of the device and the marker band. The gaps between the fibers would serve as the outlet port for any flow generated at the distal tip. It may be preferable to reinforce the exposed optical fibers in some manner, such as having a mandrel spanning the open portion of the device, or having each fiber or bundle of fibers encased in a small tube, such as a polyimide tube, to span the gap, to try to avoid breakage of one or more fibers.

If a coil is desired, but opening the coil to create the variable pitch distal windings is to be avoided, a marker band with a built-in outlet port can be constructed. FIG. 20, for example depicts such a marker band 638 having a slot 644 offset 90 degrees or so from the two fibers 616 and apertures 614 (only one set shown). Slot 644, having a width of about 0.007 inch, for example, and extending up to within about 250 microns of the distal-most edge of the cylindrical portion of the marker band, serves as an outlet port for flow generated by the optical fibers in the usual manner. Such a marker band could be about 0.025 inch long, longer than the marker band shown in FIG. 19A. This marker band could then be attached to a coil and flow would exit the device through the marker band slot 644 rather than through the variable pitch windings of the coil.

While the foregoing has described preferred illustrative embodiments of the invention, other embodiments of the invention are possible. Moreover, while the context in which the current invention has been explained concerns addressing a total or partial occlusion of a human vessel, the present invention, including its pumping/sucking aspects, would have application beyond the human body to any context in which it would be practical to move fluid from one location to another using radiation energy. Furthermore, while certain materials of construction have been identified herein, the inventions are not particularly dependent upon the types of materials used. While various structures are shown in this disclosure as being part of a marker band versus the body sheath of a device, or vice versa, it is possible to construct devices within the scope of the present invention so that the features of the marker band were present in the distal portion of the body sheath, and vice versa. Moreover, while various constructions of various embodiments disclosed herein have been described for devices of certain sizes, it is within the scope of the present invention to construct the various disclosed embodiments in larger or smaller sizes, as appropriate or as desired. Further, it may be possible to achieve some or all of the phenomena described in the present disclosure by using forms of radiation other than pulsed radiation, such as continuous wave radiation. The disclosure of pulsed radiation herein should not be understood as limiting the scope of the present invention. Finally, it should be understood that while certain beliefs concerning the present invention, its operation, and associated theories are expressed by way of explanation, the invention is not so limited. The invention is entitled to protection within the full scope of the appended claims.

It is claimed:

1. An apparatus for disrupting occlusive material in a body lumen, comprising:
   at least one optical fiber coupled to a source of energy and having a distal end for delivery of energy therefrom;
   a first annular structure having a wall, an open proximal end and an open distal end, the wall having at least one port, the distal end of said optical fiber positioned within said first annular structure in a vicinity of said port, such that energy delivered from the distal end of the optical fiber generates fluid motion in the vicinity of the port sufficient to disrupt occlusive material external to the port; and
   a second annular structure for enabling guidewire-free delivery of a distal end of the apparatus to the occlusive material to be disrupted, a length of said optical fiber positioned within said second annular structure, said annular structure being elongated, flexible and operably connected to said first annular structure.

2. An apparatus for disrupting occlusive material in a body lumen upon delivery of a distal end of the apparatus to the occlusive material, comprising:
   a first annular structure extending along a first length to a first distal end thereof;
   a second annular structure having an open proximal end and extending along a second length to a second distal end thereof, which second length is less than the first length, said second annular structure disposed external of said first annular structure with the second length adjacent the first length and the second distal end coplanar with the first distal end;
   at least one first optical fiber having a distal end, the distal end of said first optical fiber housed within said second annular structure;
   at least one second optical fiber having a distal end, the distal end of said second optical fiber disposed externally of said first and said second annular structures near the distal end of the apparatus; and
   third annular structure which houses said first and second annular structures and said first and second optical fibers near the distal end of the apparatus.

3. An apparatus for disrupting occlusive material in a body lumen, comprising:
   at least one optical fiber for receiving radiation energy from a source thereof, said at least one optical fiber having a distal end for delivering radiation energy; and
   an annular structure having at least one opening along a length thereof and an open distal end, the at least one opening having a distal-most portion, said at least one optical fiber disposed within said annular structure such that the distal end of the at least one optical fiber is a distance from the distal-most portion of the at least one opening and energy delivered from the distal end of the at least one optical fiber generates fluid motion in the vicinity of the at least one opening sufficient to disrupt occlusive material external to the at least one opening, said annular structure of construction sufficient for delivery of the open distal end thereof to occlusive material in the lumen.

4. The apparatus of claim 3, wherein said at least one optical fiber and the at least one opening are of a number more than one, each optical fiber corresponding to one opening, the openings being substantially evenly distributed relative to a circumference of said annular structure and each optical fiber being positioned such that the distal end thereof is a distance from the distal-most portion of the corresponding opening.

5. The apparatus of claim 4, herein the number is four.

6. The apparatus of claim 3, wherein the distance, is about one-half of a length of the at least one opening.

7. The apparatus of claim 3, wherein the distance is about one-quarter of a length of the at least one opening.

8. The apparatus of claim 4, wherein said annular structure has a diameter at the open distal end of up to about 1 French.

9. The apparatus of claim 3, wherein said annular structure has a diameter at the open distal end of about 0.028 inch to about 0.042 inch.

10. The apparatus of claim 3, wherein said annular structure is of a construction sufficient for moving over a guide wire.

11. The apparatus of claim 10, wherein said annular structure is of a construction sufficient for moving over a guide wire through the occlusive material such that the at least one opening is distal of the occlusive material.

12. The apparatus of claim 3, wherein the distal-most portion of the said at least one opening is angular.

13. The apparatus of claim 3, wherein at least a portion of the annular structure is asymmetric relative to the at least one optical fiber therein.

14. The apparatus of claim 13, wherein the at least a portion of the annular structure is selected from the open distal end of the annular structure, a bevel structure adjacent the open distal of the annular structure, a corner structure adjacent the open distal end of the annular structure, a wall of the annular structure, the at least one opening of the annular structure, the distal-most portion of the at least one opening of the annular structure, and any combination thereof.

15. The apparatus of claim 3, wherein the radiation energy comprises radiation energy that is well absorbed in blood.

16. The apparatus of claim 3, wherein the radiation energy comprises radiation energy that is poorly absorbed in wall tissue of the lumen.

17. The apparatus of claim 3, wherein the radiation energy comprises radiation energy having a wavelength of about 414 nm.

18. The apparatus of claim 3, Wherein the radiation energy comprises radiation energy having a wavelength of about 532 nm.

19. The apparatus of claim 3, wherein the radiation energy comprises radiation energy having a wavelength corresponding to an absorption coefficient in blood of about 240 $cm^{-1}$.

20. The apparatus of claim 3, wherein the source of radiation energy is a laser.

21. The apparatus of claim 3, wherein the source of radiation energy is a doubled Nd:YAG laser.

22. The apparatus of claim 3, wherein the radiation energy comprises radiation energy that is pulsed at about 5 kHz.

23. The apparatus of claim 3, wherein the radiation energy comprises pulsed radiation energy having a pulse width of about 25 nanoseconds.

24. The apparatus of claim 3, wherein the radiation energy comprises radiation energy of about 100 to 300 $\mu$J per pulse of energy.

25. The apparatus of claim 3, wherein said annular structure comprises a bevel portion adjacent the open distal end thereof.

26. The apparatus of claim 25, wherein the bevel portion is of a construction sufficient to extend into a radiation delivery pathway from the distal end of said at least one optical fiber.

27. The apparatus of claim 26, wherein the open distal end of said annular structure is of a construction sufficient to allow passage of a guidewire disposed within said annular structure through the open distal end, and the bevel portion is of a construction sufficient to prevent irradiation of the guidewire when the guidewire is passed through the open :distal end and the distal end of said at least one optical fiber delivers radiation energy.

28. The apparatus of claim 25, wherein the bevel portion has at least one opening therein.

29. The apparatus of claim 28, wherein the at least one opening in the bevel portion is aligned with said at least one optical fiber.

30. The apparatus of claim 28, wherein the at least one opening in the bevel portion and the at least one opening in said annular structure define an edge for disrupting occlusive material.

31. The apparatus of claim 28, wherein the at least one opening in the bevel portion allows fluid flow therethrough.

32. The apparatus of claim 3, wherein the open distal end of said annular structure is of a construction sufficient for passage of occlusive material from the lumen through the open distal end, into said annular structure.

33. The apparatus of claim 32, wherein the open distal end is of a construction sufficient to disrupt occlusive material passing therethrough.

34. The apparatus of claim 32, wherein the at least one opening of said annular structure is of a construction sufficient for passage of occlusive material from the annular structure through the at least one opening, out of said annular structure.

35. The apparatus of claim 34, wherein the at least one opening is of a construction sufficient to disrupt occlusive material passing therethrough.

36. The apparatus of claim 3, wherein the radiation energy is determined by at least one parameter selected from a diameter of the at least one optical fiber, a pattern of pulse repetition, a viscosity of fluid in the lumen, and heat build-up in the fluid, and any combination thereof.

37. The apparatus of claim 3, further comprising means for measuring the temperature of fluid in the lumen.

38. The apparatus of claim 3, further comprising means for controlling the radiation energy in a feedback control loop.

39. The apparatus of claim 38, wherein the means for controlling is automated.

40. The apparatus of claim 3, wherein the radiation energy comprises radiation energy characterized by at least one cycle of an "on" phase and an "off" phase.

41. The apparatus of claim 40, wherein the radiation energy comprises radiation energy having a duty cycle of about 30%.

42. The apparatus of claim 40, wherein the radiation energy comprises radiation energy having a duty cycle of about 33%.

43. The apparatus of claim 40, wherein the "on" phase comprises about 100 pulses of energy.

44. The apparatus of claim 40, wherein the "off" phase comprises about 200 pulses of energy.

45. The apparatus of claim 3, wherein said annular structure comprises a distal portion.

46. The apparatus of claim 45, wherein the distal: portion comprises a marker band.

47. The apparatus of claim 45, wherein the distal portion has a length of about 0.020 inch to about 0.060 inch.

48. The apparatus of claim 45, wherein said annular structure further comprises an elongated annular structure proximally abutting the distal portion;.

49. The apparatus of claim 48, further comprising a thermocouple wire disposed within the elongated annular structure, wherein a distal end of the thermocouple wire lies within the distal portion of said annular structure.

50. The apparatus of claim 48, further comprising a platinum ribbon disposed within the elongated annular structure, wherein a portion of the platinum ribbon which is most distal relative to the apparatus lies within the distal portion of said annular structure.

51. The apparatus of claim 48, wherein the elongated annular structure is of a construction sufficient for delivery of the open distal end of said annular structure to occlusive material in the lumen.

52. The apparatus of claim 48, wherein the elongated annular structure is of variable construction along a length thereof.

53. The apparatus of claim 48, wherein the elongated annular structure has a diameter that increases in a proximal direction along a length thereof.

54. The apparatus of claim 48, wherein the elongated annular structure comprises a distal-most annular section.

55. The apparatus of claim 54, wherein the distal-most annular section is composed of polyvinyl chloride.

56. The apparatus of claim 54, wherein the distal-most annular section has a length of about 3 cm.

57. The apparatus of claim 54, wherein the elongated annular structure comprises a first annular section proximally abutting the distal-most annular section.

58. The apparatus of claim 57, wherein the first annular section is composed of low-density polyethylene.

59. The apparatus of claim 57, wherein the first annular section has a length of about 5 cm.

60. The apparatus of claim 57, wherein the elongated annular structure comprises a second annular section proximally abutting the first annular section.

61. The apparatus of claim 60, wherein the second annular section is composed of high-density polyethylene.

62. The apparatus of claim 60, wherein the second annular section has a length of about 47 cm.

63. The apparatus of claim 60, wherein the elongated annular structure comprises a proximal annular section proximally abutting the second annular section.

64. The apparatus of claim 63, wherein the proximal annular section is composed of a composite of polyimide and stainless steel.

65. The apparatus of claim 63, wherein the proximal annular section has a length of about 95 cm.

66. The apparatus of claim 48, wherein said annular structure further comprises an interior annular structure within the elongated annular structure.

67. The apparatus of claim 66, wherein the interior annular structure is of variable construction along a length thereof.

68. The apparatus of claim 66, wherein the interior annular structure has a diameter that increases in a proximal direction along a length thereof.

69. The apparatus of claim 66, wherein along a length of the interior annular structure, said at least one optical fiber lies between the elongated annular structure and the interior annular structure.

70. The apparatus of claim 66, wherein along a length of the interior annular structure, a thermocouple wire lies between the elongated annular structure and the interior annular structure.

71. The apparatus of claim 66, wherein along a length of the interior annular structure, a platinum ribbon lies between the elongated annular structure and the interior annular structure.

72. The apparatus of claim 66, wherein the interior annular structure comprises a distal-most annular section.

73. The apparatus of claim 72, wherein the distal-most annular section is composed of polyvinyl chloride.

74. The apparatus of claim 72, wherein a distal end of the distal-most annular section lies within the distal portion of said annular structure.

75. The apparatus of claim 74, wherein the distal end of the distal-most annular section lies at about one-half of a length of the at least one opening.

76. The apparatus of claim 72, wherein the interior annular structure further comprises a tube within the distal-most annular section.

77. The apparatus of claim 76, wherein the tube has a length which is less than that of the distal-most annular section and a distal end of the distal-most annular section and a distal end of the tube are co-terminal.

78. The apparatus of claim 72, wherein the interior annular structure comprises a proximal annular section proximally abutting the distal-most annular section.

79. The apparatus of claim 78, wherein the proximal annular section is composed of polypropylene.

80. The apparatus of claim 78, wherein the proximal annular section has a length which is greater than that of the distal-most annular section.

81. The apparatus of claim 78, wherein a proximal end of the proximal annular section and a proximal end of said annular structure are co-terminal.

82. The apparatus of claim 66, wherein along a portion of the length of the elongated annular structure, at least one hole extends through the elongated annular structure and the interior annular structure.

83. The apparatus of claim 82, wherein the at least one hole has a diameter of from about 0.005 inch to about 0.012 inch.

84. The apparatus of claim 82, wherein the at least one hole is oval and has dimensions of from about 0.003 inch by about 0.005 inch to about 0.003 ich by about 0.011 inch.

85. The apparatus of claim 82, wherein the at least one hole is of a construction sufficient to provide a blood flow therethrough of from about 1 cm$^3$ to about 6 cm$^3$ in 60 seconds.

86. The apparatus of claim 82, wherein the at least one hole comprises at least one set of holes disposed along a length of the portion, the holes in each set disposed annularly around the portion.

87. The apparatus of claim 86, wherein the holes in each set are substantially evenly disposed annularly around the portion.

88. The apparatus of claim 86, wherein the at least one set of holes is disposed a predetermined distance from the open distal end of said annular structure, the predetermined distance selected from about 3 cm, about 4 cm, about 5 cm, and any combination thereof.

89. The apparatus of claim 3, wherein the distance is about 125 microns.

90. A method for disrupting occlusive material in a body lumen, comprising:
   providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
   delivering the annular structure to occlusive material in the lumen; and
   delivering radiation energy from the at least one optical fiber sufficient to generate fluid motion in the vicinity of the at least one opening and to disrupt occlusive material external to the at least one opening.

91. The method of claim 90, wherein said providing is such that the at least one optical fiber and the at least one opening are of a number more than one, each optical fiber corresponding to one opening, the openings being substantially evenly distributed relative to a circumference of the annular structure and each optical fiber being positioned such that the distal end thereof is a distance from the distal-most portion of the corresponding opening.

92. The method of claim 90, wherein said providing is such that the distance is about one-half of a length of the at least one opening.

93. The method of claim 90, wherein said providing is such that the distance is about one-quarter of a length of the at least one opening.

94. The method of claim 90, wherein said delivering the annular structure comprises moving the annular structure over a guide wire.

95. The method of claim 90, wherein said delivering the open distal end of the annular structure comprises moving the annular structure over a guide wire through the occlusive material such that the open distal end of the annular structure is distal of the occlusive material.

96. The method of claim 95, further comprising positioning the guide wire proximally relative to the open distal end of the annular structure.

97. The method of claim 95, wherein said delivering radiation energy follows said delivering the open distal end such that the open distal end of the annular structure is distal of the occlusive material.

98. The method of claim 97, further comprising positioning the guide wire proximally relative to the open distal end of the annular structure, wherein said positioning precedes said delivering radiation energy.

99. The method of claim 97, further comprising moving the open distal end of the annular structure proximally, said moving of the open distal end following initiation of said delivering radiation energy.

100. The method of claim 99, wherein at least upon said moving the open distal end of the annular structure proximally, the guide wire is distal of the open distal end of the annular structure.

101. The method of claim 100, further comprising providing a structure adjacent the open distal end of the annular structure to prevent irradiation of the guide wire upon said delivering radiation energy.

102. The method of claim 99, wherein said moving the open distal end of the annular structure comprises moving the open distal end proximally into the occlusive material.

103. The method of claim 99, wherein said moving the open distal end of the annular structure comprises moving the open distal end proximally through the occlusive material.

104. The method of claim 101, further comprising repeating at least once said moving the annular structure over a guide wire such that the open distal end of the annular structure is distal of the occlusive material and repeating at least once said moving the open distal end of the annular structure proximally through the occlusive material.

105. The method of claim 94, wherein said moving the annular structure over a guide wire comprises positioning the guide wire distal of the occlusive material and moving the annular structure distally into the occlusive material.

106. The method of claim 105, wherein said positioning the guide wire comprises positioning the guide wire distal of the open distal end of the annular structure and said delivering radiation energy comprises delivering radiation energy during said moving the annular structure distally.

107. The method of claim 106, wherein upon said positioning the guide wire, the guide wire remains distal of the open distal end of the annular structure.

108. The method of claim 90, wherein said delivering the annular structure comprises moving the annular structure over a guide wire.

109. The method of claim 90, wherein said delivering radiation energy comprises delivering radiation energy that is poorly absorbed in wall tissue of the lumen.

110. The method of claim 90, wherein said delivering radiation energy comprises delivering radiation energy having a wavelength of about 414 nm.

111. The method of claim 90, wherein said delivering radiation energy comprises delivering radiation energy having a wavelength of about 532 nm.

112. The method of claim 90, wherein said delivering radiation energy comprises delivering radiation energy having a wavelength corresponding to, an absorption coefficient in blood of about 240 $cm^{-1}$.

113. The method of claim 90, wherein the source of radiation energy is a laser.

114. The method of claim 113, wherein the source of radiation energy is a doubled Nd:YAG laser.

115. The method of claim 90, wherein said delivering radiation energy comprises delivering energy that is pulsed at about 5 kHz.

116. The method of claim 90, wherein said delivering radiation energy comprises delivering pulsed energy using a pulse width of about 25 nanoseconds.

117. The method of claim 90, wherein said delivering radiation energy comprises delivering energy of about 100 to 300 $\mu$J per pulse of energy.

118. The method of claim 90, wherein said delivering radiation energy comprises delivering energy in at least one cycle of an "on" phase and an "of" phase.

119. The method of claim 118, wherein the at least one cycle comprises a duty cycle of about 30%.

120. The method of claim 118, wherein the at least one cycle comprises a duty cycle of about 33%.

121. The method of claim 118, wherein the "on" phase comprises about 100 pulses of energy.

122. The method of claim 118, wherein the "off" phase comprises about 200 pulses of energy.

123. The method of claim 90, wherein said delivering radiation energy comprises delivering energy determined by at least one parameter selected from a diameter of the at least one optical fiber, a pattern of pulse repetition, a viscosity of fluid in the lumen, and heat build-up in the fluid, and any combination thereof.

124. The method of claim 90, further comprising measuring the temperature of fluid in the lumen.

125. The method of claim 90, wherein said delivering radiation energy comprises controlling the radiation energy in a feedback control loop.

126. The method of claim 125, wherein the controlling is automatic.

127. The method of claim 90, wherein said delivering radiation energy comprises formation of a bubble at the distal end of the at least one optical fiber.

128. The method of claim 127, wherein said delivering radiation energy comprises expansion of the bubble.

129. The method of claim 128, wherein the bubble is substantially spherical upon formation and wherein said delivering radiation energy comprises expansion of the bubble such that a shape of at least a portion of the bubble is altered in an environment defined by the annular structure.

130. The method of claim 129, wherein when the shape of at least a portion of the bubble is altered, the bubble becomes asymmetric.

131. The method of claim 129, wherein the at least a portion of the annular structure is asymmetric relative to the at least one optical fiber therein.

132. The method of claim 131, wherein the at least a portion of the annular structure is selected from the open distal end of the annular structure, a bevel structure adjacent the open distal end of the annular structure, a corner structure adjacent the open distal end of the annular structure, a wall of the annular structure, the at least one opening of the annular structure, the distal-most portion of the at least one opening of the annular structure, and any combination thereof.

133. The method of claim 128, wherein said delivering radiation energy comprises collapse of the bubble.

134. The method of claim 133, wherein said delivering radiation energy comprises displacement of fluid associated with the lumen in a vicinity of the distal end of the at least one optical fiber.

135. The method of claim 134, wherein said delivering radiation energy comprises movement of fluid associated with the lumen from the lumen into the open distal end of the annular structure.

136. The method of claim 135, wherein said delivering radiation energy comprises movement of fluid associated with the lumen from within the annular structure through the at least one opening of the annular structure.

137. The method of claim 133, wherein said delivering radiation energy comprises directional displacement of fluid associated with the lumen from a vicinity of the open distal end of the annular structure through the at least one opening of the annular structure.

138. The method of claim 137, wherein said delivering radiation energy comprising the directional displacement of fluid takes place in a period of up to 60 mseconds.

139. The method of claim 138, wherein said delivering radiation energy comprising the directional displacement of fluid takes place in a period of up to 100 µseconds.

140. The method of claim 133, wherein said delivering radiation energy comprises delivering energy in at least one cycle of formation, expansion and collapse of the bubble.

141. The method of claim 140, wherein said delivering radiation energy comprises delivering energy in more than one cycles.

142. The method of claim 141, wherein said delivering radiation energy comprises producing more than one displacements of fluid associated with the lumen through the at least one opening of the annular structure.

143. The method of claim 142, wherein said delivering radiation energy comprises moving one displacement of fluid further from the at least one opening of the annular structure over time.

144. The method of claim 142, wherein said delivering radiation energy comprises expelling the more than one fluid displacements from the at least one opening of the annular structure in a jet.

145. The method of claim 144, wherein said delivering radiation energy comprising expelling the more than one fluid displacements in the jet takes place over a period of up to 60 mseconds.

146. The method of claim 144, wherein said providing comprises providing more than one optical fibers within the annular structure, the at least one opening of the annular structure comprising more than one openings, and wherein said delivering radiation energy comprises delivering energy from one optical fiber and subsequently delivering energy from another optical fiber.

147. The method of claim 146, wherein said delivering radiation energy comprises an interval between delivering energy from one fiber optical and subsequently delivering energy from another optical fiber, the interval comprising an absence of delivering radiation energy from any of the more than one optical fibers.

148. The method of claim 146, wherein said delivering radiation energy comprises delivering energy from the more than one optical fibers in a schedule.

149. The method of claim 148, wherein the schedule is selected from a sequence of adjacent optical fibers, a sequence of opposite optical fibers, and a sequence of any combination of optical fibers.

150. The method of claim 148, wherein the schedule is determined by at least one parameter selected from a nature of the occlusive material, a position of the occlusive material, and a region of heat build-up in the lumen.

151. The method of claim 146, wherein said delivering radiation energy is sufficient to cause a jetting of fluid associated with the lumen from one or more of the openings.

152. The method of claim 151, wherein the jetting of fluid from any one of the openings is asymmetric relative to the annular structure.

153. The method of claim 151, wherein said delivering of radiation energy is sufficient to cause agitation of occlusive material in a vicinity of the open distal end of the annular structure.

154. The method of claim 151, wherein said delivering of radiation energy is sufficient to cause movement of the open distal end of the annular structure.

155. The method of claim 90, wherein said providing comprises providing an annular structure having at least one hole along a length thereof for blood flow therethrough.

156. The method of claim 155, wherein the blood flow is from the lumen through the at least one hole into the annular structure and in a distal direction within the annular structure.

157. The method of claim 90, wherein said providing is such that the distance is about 125 microns.

158. An apparatus for disrupting occlusive material in a body lumen, comprising:
   at least one optical fiber for receiving radiation energy from a source thereof, said at least one optical fiber having a distal end for delivering radiation energy; and
   an annular structure having at least one opening along a length thereof and an open distal end, the at least one opening having a distal-most portion, said at least one optical fiber disposed within said annular structure such that the distal end of the at least one optical fiber is a distance from the distal-most portion of the at least one opening, said annular structure of construction sufficient for delivery of the open distal end thereof to occlusive material in the lumen;
   wherein said at least one optical fiber and the at least one opening are of a number more than one, each optical fiber corresponding to one opening, the openings being substantially evenly distributed relative to a circumference of said annular structure and each optical fiber being positioned such that the distal end thereof is a distance from the distal-most portion of the corresponding opening.

159. The apparatus of claim 158, wherein the number is four.

160. An apparatus for disrupting occlusive material in a body lumen, comprising:
   at least one optical fiber for receiving radiation energy from a source thereof, said at least one optical fiber having a distal end for delivering radiation energy; and
   an annular structure having at least one opening along a length thereof and an open distal end, the at least one opening having a distal-most portion, said at least one optical fiber disposed within said annular structure such that the distal end of the at least one optical fiber is a distance from the distal-most portion of the at least one opening, said annular structure of construction sufficient for delivery of the open distal end thereof to occlusive material in the lumen, said annular structure comprising a bevel portion adjacent the open distal end thereof.

161. The apparatus of claim 160, wherein the bevel portion is of a construction sufficient to extend into a radiation delivery pathway from the distal end of said at least one optical fiber.

162. The apparatus of claim 161, wherein the open distal end of said annular structure is of a construction sufficient to allow passage of a guidewire disposed within said annular structure through the open distal end, and the bevel portion is of a construction sufficient to prevent irradiation of the guidewire when the guidewire is passed through the open distal end and the distal end of said at least one optical fiber delivers radiation energy.

163. The apparatus of claim 160, wherein the bevel portion has at least one opening therein.

164. The apparatus of claim 163, wherein the at least one opening in the bevel portion is aligned with said at least one optical fiber.

165. The apparatus of claim 163, wherein the at least one opening in the bevel portion and the at least one opening in said annular structure define an edge for disrupting occlusive material.

166. The apparatus of claim 163, wherein the at least one opening in the bevel portion allows fluid flow therethrough.

167. An apparatus for disrupting occlusive material in a body lumen, comprising:
at least one optical fiber for receiving radiation energy from a source thereof, said at least one optical fiber having a distal end for delivering radiation energy; and
an annular structure having at least one opening along a length thereof and an open distal end, the at least one opening having a distal-most portion, said at least one optical fiber disposed within said annular structure such that the distal end of the at least one optical fiber is a distance from the distal-most portion of the at least one opening, said annular structure of construction sufficient for delivery of the open distal end thereof to occlusive material in the lumen, said annular structure comprising a distal portion and an elongated annular structure proximally abutting the distal portion.

168. The apparatus of claim 167, wherein the elongated annular structure is of a construction sufficient for delivery of the open distal end of said annular structure to occlusive material in the lumen.

169. The apparatus of claim 167, wherein the elongated annular structure is of variable construction along a length thereof.

170. The apparatus of claim 167, wherein the elongated annular structure has a diameter that increases in a proximal direction along a length thereof.

171. The apparatus of claim 167, wherein the elongated annular structure comprises a distal-most annular section.

172. The apparatus of claim 171, wherein the distal-most annular section is composed of polyvinyl chloride.

173. The apparatus of claim 171, wherein the distal-most annular section has a length of about 3 cm.

174. The apparatus of claim 171, wherein the elongated annular structure comprises a first annular section proximally abutting the distal-most annular section.

175. The apparatus of claim 174, wherein the first annular section is composed of low-density polyethylene.

176. The apparatus of claim 174, wherein the first annular section has a length of about 5 cm.

177. The apparatus of claim 174, wherein the elongated annular structure comprises a second annular section proximally abutting the first annular section.

178. The apparatus of claim 177, wherein the second annular section is composed of high-density polyethylene.

179. The apparatus of claim 177, wherein the second annular section has a length of about 47 cm.

180. The apparatus of claim 177, wherein the elongated annular structure comprises a proximal annular section proximally abutting the second annular section.

181. The apparatus of claim 180, wherein the proximal annular section is composed of a composite of polyimide and stainless steel.

182. The apparatus of claim 180, wherein the proximal annular section has a length of about 95 cm.

183. The apparatus of claim 167, wherein said annular structure further comprises an interior annular structure within the elongated annular structure.

184. The apparatus of claim 183, wherein the interior annular structure is of variable construction along a length thereof.

185. The apparatus of claim 183, wherein the interior annular structure has a diameter that increases in a proximal direction along a length thereof.

186. The apparatus of claim 183, wherein the interior annular structure comprises a distal-most annular section.

187. The apparatus of claim 186, wherein the distal-most annular section is composed of polyvinyl chloride.

188. The apparatus of claim 186, wherein a distal end of the distal-most annular section lies within the distal portion of said annular structure.

189. The apparatus of claim 188, wherein the distal end of the distal-most annular section lies at about one-half of a length of the at least one opening.

190. The apparatus of claim 186, wherein the interior annular structure further comprises a tube within the distal-most annular section.

191. The apparatus of claim 190, wherein the tube has a length which is less than that of the distal-most annular section and a distal end of the distal-most annular section and a distal end of the tube are co-terminal.

192. The apparatus of claim 186, wherein the interior annular structure comprises a proximal annular section proximally abutting the distal-most annular section.

193. The apparatus of claim 192, wherein the proximal annular section is composed of polypropylene.

194. The apparatus of claim 192, wherein the proximal annular section has a length which is greater than that of the distal-most annular section.

195. The apparatus of claim 192, wherein a proximal end of the proximal annular section and a proximal end of said annular structure are co-terminal.

196. The apparatus of claim 183, wherein along a length of the interior annular structure, said at least one optical fiber lies between the elongated annular structure and the interior annular structure.

197. The apparatus of claim 183, wherein along a length of the interior annular structure, a thermocouple wire lies between the, elongated annular structure and the interior annular structure.

198. The apparatus of claim 183, wherein along a length of the interior annular structure, a platinum ribbon lies between the elongated annular structure and the interior annular structure.

199. The apparatus of claim 167, further comprising a thermocouple wire disposed within the elongated annular structure, wherein a distal end of the thermocouple wire lies within the distal portion of said annular structure.

200. The apparatus of claim 167, further comprising a platinum ribbon disposed within the elongated annular structure, wherein a portion of the platinum ribbon which is most distal relative to the apparatus lies within the distal portion of said annular structure.

201. The apparatus of claim 183, wherein along a portion of the length of the elongated annular structure, at least one hole extends through the elongated annular structure and the interior annular structure.

202. The apparatus of claim 201, wherein the at least one hole comprises at least one set of holes disposed along a length of the portion, the holes in each set disposed annularly around the portion.

203. The apparatus of claim 202, wherein the holes in each set are substantially evenly disposed annularly around the portion.

204. The apparatus of claim 202, wherein the at least one set of holes is disposed a predetermined distance from the open distal end of said annular structure, the predetermined distance selected from about 3 cm, about 4 cm, about 5 cm, and any combination thereof.

205. The apparatus of claim 201, wherein the at least one hole has a diameter of from about 0.005 inch to about 0.012 inch.

206. The apparatus of claim 201, wherein the at least one hole is oval and has dimensions of from about 0.003 inch by about 0.005 inch to about 0.003 inch by about 0.011 inch.

207. The apparatus of claim 201, wherein the at least one hole is of a construction sufficient to provide a blood flow therethrough of from about 1 cm$^3$ to about 6 cm$^{-1}$ in 60 seconds.

208. An apparatus for disrupting occlusive material in a body lumen, comprising:
at least one optical fiber for receiving radiation energy from a source thereof, said at least one optical fiber having a distal end for delivering radiation energy, the radiation energy characterized by at least one cycle of an "on" phase and an "off" phase, the at least one cycle comprising a duty cycle selected from a group consisting of about 30% and about 33%; and
an annular structure having at least one opening along a length thereof and an open distal end, the at least one opening having a distal-most portion, said at least one optical fiber disposed within said annular structure such that the distal end of the at least one optical fiber is a distance from the distal-most portion of the at least one opening, said annular structure of construction sufficient for delivery of the open distal end thereof to occlusive material in the lumen.

209. The apparatus of claim 208, wherein the "on" phase comprises about 100 pulses of energy.

210. The apparatus of claim 208, wherein the "off" phase comprises about 200 pulses of energy.

211. The method for disrupting occlusive material in a body lumen, comprising:
providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
delivering the annular structure to occlusive material in the lumen; and
delivering radiation energy from the at least one optical fiber;
wherein said providing is such that the at least one optical fiber and the at least one opening are of a number more than one, each optical fiber corresponding to one opening, the openings being substantially evenly distributed relative to a circumference of the annular structure and each optical fiber being positioned such that the distal end thereof is a distance from the distal-most portion of the corresponding opening.

212. The method of claim 211, wherein said delivering the open distal end of the annular structure comprises moving the annular structure over a guide wire through the occlusive material such that the open distal end of the annular structure is distal of the occlusive material, further comprising providing a structure adjacent the open distal end of the annular structure to prevent irradiation of the guide wire upon said delivering radiation energy.

213. The method of claim 211, further comprising repeating at least once said moving the annular structure over a guide wire such that the open distal end of the annular structure is distal of the occlusive material and repeating at least once said moving the open distal end of the annular structure proximally through the occlusive material.

214. The method of claim 211, wherein the source of radiation energy is a doubled Nd:YAG laser.

215. A method for disrupting occlusive material in a body lumen, comprising:
providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
delivering the annular structure to occlusive material in the lumen; and
delivering radiation energy from the at least one optical fiber, said delivering radiation energy comprising delivering energy in at least one cycle of an "on" phase and an "off" phase, the at least one cycle comprising a duty cycle selected from a group consisting of about 30% and about 33%.

216. A method for disrupting occlusive material in a body lumen, comprising:
providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
delivering the annular structure to occlusive material in the lumen; and
delivering radiation energy from the at least one optical fiber, said delivering radiation energy comprising delivering energy in at least one cycle of an "on" phase comprising about 100 pulses of energy.

217. A method for disrupting occlusive material in a body lumen, comprising:
providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
delivering the annular structure to occlusive material in the lumen; and delivering radiation energy from the at least one optical fiber, said delivering radiation energy comprising delivering energy in at least one cycle of an "off" phase comprising about 200 pulses of energy.

218. A method for disrupting occlusive material in a body lumen, comprising:
providing at least one optical fiber for receiving radiation energy from a source thereof, the at least one optical fiber having a distal end for delivering radiation energy, the at least one fiber disposed within an annular structure, the annular structure having at least one opening along a length thereof and having an open distal end, the at least one opening having a distal-most portion, the distal end of the at least one optical fiber disposed a distance from the distal-most portion of the at least one opening;
delivering the annular structure to occlusive material in the lumen; and
delivering radiation energy from the at least one optical fiber, said delivering radiation energy comprising formation and expansion of a bubble at the distal end of the at least one optical fiber.

219. The method of claim 218, wherein the bubble is substantially spherical upon formation and wherein said delivering radiation energy comprises expansion of the bubble such that a shape of at least a portion of the bubble is altered in an environment defined by the annular structure.

220. The method of claim 218, wherein when the shape of at least a portion of the bubble is altered, the bubble becomes asymmetric.

221. The method of claim 218, wherein the at least a portion of the annular structure is asymmetric relative to the at least one optical fiber therein.

222. The method of claim 221, wherein the at least a portion of the annular structure is selected from the open distal end of the annular structure, a bevel structure adjacent the open distal end of the annular structure, a comer structure adjacent the open distal end of the annular structure, a wall of the annular structure, the at least one opening of the annular structure, the distal-most portion of the at$_1$! least one opening of the annular structure, and any combination thereof.

223. The method of claim 218, wherein said delivering radiation energy comprises collapse of the bubble.

224. The method of claim 223, wherein said delivering radiation energy comprises displacement of fluid associated with the lumen in a vicinity of the distal end of the at least one optical fiber.

225. The method of claim 224, wherein said delivering radiation energy comprises movement of fluid associated with the lumen from the lumen into the open distal end of the annular structure.

226. The method of claim 225, wherein said delivering radiation energy comprises movement of fluid associated with the lumen from within the annular structure through the at least one opening of the annular structure.

227. The method of claim 223, wherein said delivering radiation energy comprises directional displacement of fluid associated with the lumen from a vicinity of the open distal end of the annular structure through the at least one opening of the annular structure.

228. The method of claim 227, wherein said delivering radiation energy comprising the directional displacement of fluid takes place in a period of up to 60 mseconds.

229. The method of claim 228, wherein said delivering radiation energy comprising the directional displacement of fluid takes place in a period of up to 100 $\mu$seconds.

230. The method of claim 223, wherein said delivering radiation energy comprises delivering energy in at least one cycle of formation, expansion and collapse of the bubble.

231. The method of claim 230, wherein said delivering radiation energy comprises delivering energy in more than one cycles.

232. The method of claim 231, wherein said delivering radiation energy comprises producing more than one displacements of fluid associated with the lumen through the at least one opening of the annular structure.

233. The method of claim 232, wherein said delivering radiation energy comprises moving one displacement of fluid further from the at least one opening of the annular structure over time.

234. The method of claim 232, wherein said delivering radiation energy comprises expelling the more than one fluid displacements from the at least one opening of the annular structure in a jet.

235. The method of claim 234, wherein said delivering radiation energy comprising expelling the more than one fluid displacements in the jet takes place over a period of up to 60 mseconds.

236. The method of claim 234, wherein said providing comprises providing more than one optical fibers within the annular structure, the at least one opening of the annular structure comprising more than one openings, and wherein said delivering radiation energy comprises delivering energy from one optical fiber and subsequently delivering energy from another optical fiber.

237. The method of claim 236, wherein said delivering radiation energy comprises an interval between delivering energy from one fiber optical and subsequently delivering energy from another optical fiber, the interval comprising an absence of delivering radiation energy from any of the more than one optical fibers.

238. The method of claim 236, wherein said delivering radiation energy comprises delivering energy from the more than one optical fibers in a schedule.

239. The method of claim 236, wherein the schedule is selected from a sequence of adjacent optical fibers, a sequence of opposite optical fibers, and a sequence of any combination of optical fibers.

240. The method of claim 238, wherein the schedule is determined by at least one parameter selected from a nature of the occlusive material, a position of the occlusive material, and a region of heat build-up in the lumen.

241. The method of claim 236, wherein said delivering radiation energy is sufficient to cause a jetting of fluid associated with the lumen from one or more of the openings.

242. The method of claim 241, wherein the jetting of fluid from any one of the openings is asymmetric relative to the annular structure.

243. The method of claim 241, wherein,said delivering of radiation energy is sufficient to cause agitation of occlusive material in a vicinity of the open distal end of the annular structure.

244. The method of claim 241, wherein said delivering of radiation energy is sufficient to cause movement of the open distal end of the annular structure.

* * * * *